US007026119B2

(12) United States Patent
Nicolaides et al.

(10) Patent No.: US 7,026,119 B2
(45) Date of Patent: Apr. 11, 2006

(54) METHODS FOR GENERATING HYPERMUTABLE MICROBES

(75) Inventors: Nicholas C. Nicolaides, Boothwyn, PA (US); Philip M. Sass, Audubon, PA (US); Luigi Grasso, Philadelphia, PA (US); Bert Vogelstein, Baltimore, MD (US); Kenneth W. Kinzler, Bel Air, MD (US)

(73) Assignees: Morphotek, Inc., Philadelphia, PA (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/780,675

(22) Filed: Feb. 12, 2001

(65) Prior Publication Data

US 2002/0068284 A1 Jun. 6, 2002

Related U.S. Application Data

(60) Provisional application No. 60/181,929, filed on Feb. 11, 2000.

(51) Int. Cl.
*C12Q 1/68* (2006.01)
*C12N 15/74* (2006.01)
*C12N 1/20* (2006.01)

(52) U.S. Cl. .................. 435/6; 435/471; 435/252.1
(58) Field of Classification Search ............ 435/252.3, 435/471, 440, 243
See application file for complete search history.

(56) References Cited

U.S. PATENT DOCUMENTS

| 5,907,079 A | 5/1999 | Mak et al. |
| 6,146,894 A * | 11/2000 | Nicolaides et al. |
| 6,191,268 B1 | 2/2001 | Liskay et al. |
| 6,287,862 B1 | 9/2001 | delCardayre et al. |

FOREIGN PATENT DOCUMENTS

| CA | 2240609 | 8/1998 |
| WO | WO 97/08312 | 3/1997 |
| WO | WO 99/19492 | 4/1999 |

OTHER PUBLICATIONS

Aronshtam et al (1996) Nucleic Acids Research 24:2498-2504.*
pET-15b Vector (Novagen) May 1999, [online], [retrieved on Jul. 8, 2002] Retrieved using Internet URL:http://www.novagen.com/SharedImages/TechnicalLiterature/7_TB045.pdf.*
Wu et al (1994) Journal of Bacteriology 176:5393-5400.*
Winnacker, "From Genes to Clones, Introduction to Gene Technology", Translation by Horst Ibelgaufts, Weinheim, New York, VCH, 1987, pp. 241-242.*
Bell et al (1994) Genomics 19:137-144.*
Bjornson et al (2000) Biochemistry 39 :3176-3183.*
Kong et al (1999) Molecular Immunology 36 :83-91.*
Schrader et al (1999) J. Exp. Med. 190 :323-330.*
Harfe et al (2000) Annual Review of Genetics 34:359-399.*
Fishel et al (1993) Cell 75:1027-1038.*
Prudhomme et al (1991) J. Bacteriology 173:7196-7203.*
Nicolaides et al (1995) Genomics 30:195-206.*
Kondo et al. J. Biochem. 1999; 125: 818-825.*
Allen, D., et al., "MutS mediates heteroduplex loop formation by a translocation mechanism" *EMBO J.*, 1997, 16(14), 4467-4476.
Baker, S.M., et al., "Male mice defective in the DNA mismatch repair gene PMS2 exhibit abnormal chromosome synapsis in meiosis" *Cell*, 1995, 82, 309-319.
Bronner C.E., et al., "Mutation in the DNA mismatch repair gene homologue hMLH1 is associated with hereditary nonpolyposis colon cancer" *Nature*, 1994, 368, 258-261.
de Wind, N., et al., "Inactivation of the mouse Msh2 gene results in mismatch repair deficiency, methylation tolerance, hyperrecombination, and predisposition to cancer" *Cell*, 1995, 82, 321-330.
Drummond, J.T., et al., "Isolation of an hMSH2-p160 heterodimer that restores DNA mismatch repair to tumor cells" *Science*, 1995, 268, 1909-1912.
Drummond, J.T., et al., "Cisplatin and adriamycin resistance are associated with mutla and mismatch repair deficiency in an ovarian tumor cell line" *J. Biological Chemistry*, 1996, 271(33), 19645-19648.

(Continued)

*Primary Examiner*—David Guzo
*Assistant Examiner*—Ramin (Ray) Akhavan
(74) *Attorney, Agent, or Firm*—Banner & Witcoff, Ltd.

(57) ABSTRACT

Bacteria are manipulated to create desirable output traits using dominant negative alleles of mismatch repair proteins. Enhanced hypermutation is achieved by combination of mismatch repair deficiency and exogenously applied mutagens. Stable bacteria containing desirable output traits are obtained by restoring mismatch repair activity to the bacteria.

15 Claims, 6 Drawing Sheets

OTHER PUBLICATIONS

Edelmann, W., et al., "Meiotic pachytene arrest in MLH1-deficient mice" *Cell*, 1996, 85, 1125-1134.

Eshleman, J.R., et al., "Mismatch repair defects in human carcinogenesis" *Human Molecular Genetics*, 1996, 5, 1489-1494.

Galio, L., et al., "ATP hydrolysis-dependent formation of a dynamic ternary nucleoprotein complex with MutS and MutL" *Nucleic Acids Research*, 1999, 27(11), 2325-2331.

Hamilton, S.R. et al. "The molecular basis of Turcot's syndrome." *N. Eng. J. Med*. 1995, 332:839-847.

Harfe, B.D. et al., "DNA mismatch repair and genetic instability" *Annu. Rev. Genet.*, 2000, 34, 359-399.

Hoang J., et al., "BAT-26, an Indicator of the Replication Error Phenotype in Colorectal Cancers and Cell Lines" *Cancer Res.*, 1997, 57, 300-303.

Holmes, J., S. Clark, and P. Modrich. "Strand-specific mismatch correction in nuclear extracts of human and *Drosophila melanogaster* cell lines" *Proc. Natl. Acad. Sci. USA* 1990 87:5837-5841.

Honma, M. et al., "Cytotoxic and Mutagenic Responses to X-rays and Chemical Mutagens in Normal and p53-mutated Human Lymphoblastoid Cells" *Mut. Res.*, 1997, 374, 89-98.

Jiricny, J., et al., "Mismatch repair defects in cancer" *Curr. Opin. Genet. Dev.*, 2000, 10, 157-161.

Karran, P., et al., "Genomic instability and tolerance to alkylating agents" *Cancer Surveys*, 1996, 28, 69-71.

Leach, F.S., et al., "Mutations of a mutS homolog in hereditary nonpolyposis colorectal cancer" *Cell*, 1993, 75, 1215-1225.

Li, G.-M. and P. Modrich. "Restoration of mismatch repair to nuclear extracts of H6 colorectal tumor cells by a heterodimer of human MutL homologs" *Proc. Natl. Acad. Sci. USA* 1995 92:1950-1954.

Liu, T, et al., "Microsatellite instability as a predictor of a mutation in a DNA mismatch repair gene in familial colorectal cancer" *Genes, Chromosomes & Cancer*, 2000, 27, 17-25.

Liu et al., "Analysis of Mismatch Repair Genes in Hereditary Non-polyposis Colorectal Cancer Patients" *Nature Medicine*, Feb. 1996, 2(2), 169-174.

Ma et al., "Dominant Negative Expression of hPMS2 Creates Isogenic Mismatch Repair Deficient Human Colon Cancer Cell Lines" *Proc. Am. Assoc. Cancer Res.*, Mar. 1998, 39, p. 460 (Abstract #3130).

McCallum, C.M., "Targeted screening for induced mutations" *Nature Biotechnology*, 2000, 18, 455-457.

Modrich, P., "Mismatch repair, genetic stability, and cancer" *Science*, 1994, 266, 1959-1960.

Nicolaides, N.C., et al., "The Jun family members, c-Jun and JunD, transactivate the human c-myb, promotor via an Ap1-like element" *J. Biological Chemistry*, 1992, 267(27), 19655-19672.

Nicolaides, N.C., et al., "Genomic organization of the human *PMS*2 gene family" *Genomics*, 1995, 30, 195-206.

Nicolaides, N.C. et al. "Molecular cloning of the N-terminus of GTBP." *Genomics* 1996, 31:395-397.

Nicolaides, N.C., et al., "Positive autoregulation of c-myb, expression via Myb binding sites in the 5'flanking region of the human c-myb gene" *Molecular and Cellular Biology*, 1991, 11(12), 6166-6176.

Nicolaides, N.C., "A naturally occurring hPMS 2 mutation can confer a dominant negative nutator phenotype" *Mol. Cell. Biol.*, 1998, 18(3), 1635-1641.

Nicolaides, N.C., et al., "Analysis of the 5'region of PMS 2 reveals heterogeneous transcripts and a novel overlapping gene" *Genomics*, 1995, 29, 329-334.

Nicolaides, N.C., et al., "Mutations of two PMS homologues in hereditary nonpolyposis colon cancer" *Nature*, 1994, 371, 75-80.

Palombo, F., et al., "Mismatch repair and cancer" *Nature*, 1994, 367,417.

Pang, Q., T.A. Prolla and R.M. Liskay, "Functional domains of the *Saccharomyces cerevisiae* Mlh1p and Pms1p DNA mismatch repair proteins and their relevance to human hereditary nonpolyposis colorectal cancer-associated mutations" *Mol. Cell. Biol.* 1997 17(8):4465-4473.

Papadopoulos, N., et al., "Mutation of a mutL homolog in hereditary colon cancer" *Science*, 1994, 263, 1625-1629.

Papadopoulos, N., et al., "Mutations of GTBP in genetically unstable cells" *Science*, 1995, 268, 1915-1917.

Parsons, R. et al. "Mismatch repair deficiency in phenotypically normal human cells." *Science* 1995 268:738-740.

Parsons, R., et al., "Hypermutability and mismatch repair deficiency in RER+tumor cells" *Cell*, 1993, 75, 1227-1236.

Peinado, M.A., et al., "Isolation and characterization of allelic losses and gains in colorectal tumors by arbitrarily primed polymerase chain reaction" *Proc. Natl. Acad. Sci. USA*, 1992, 89, 10065-10069.

Perucho, M., "Cancer of the microsatellite mutator phenotype" *Biol. Chem.*, 1996, 377, 675-684.

Prolla, T.A., et al., "MLH1, PMS1, and MSH2 interactions during the initiation of DNA mismatch repair in yeast" *Science*, 1994, 265, 1091-1093.

Quian, Y. et al., "Molecular events after antisense inhibition of hMSH2 in a HeLa cell line" *Mutation Research*, Oct. 12, 1998, vol. 418, pp. 61-71.

Spampinato, C., et al., "The MutL ATPase is required for mismatch repair" *J. Biological Chemistry*, 2000, 275(13), 9863-9869.

Strand, M., et al., "Destabilization of tracts of simple repetitive DNA in yeast by mutations affecting DNA mismatch repair" *Nature*, 1993, 365, 274-276.

Su, S., et al., "Mispair specificity of methyl-directed DNA mismatch correction in vitro" *J. Biological Chemistry*, 1988, 263(14), 6829-6835.

Vora, K.A. et al., "Severe Attenuation of the B Cell Immune Response in Msh2- deficient Mice" *Journal of Experimental Medicine*, Feb. 1999, 189(3), 471-481.

Wheeler, J.M.D., et al., "The role of hypermethylation of the hmlh 1 promoter region in HNPCC verus MSI+sporadic colorectal cancers" *J. Med. Genet.*, 2000, 588-592.

Winter, D.B. et al., "Altered spectra of hypermutation in antibodies from mice deficient for the DNA mismatch repair protein PMS2" *Proc. Natl. Acad. Sci., USA*, Jun. 1998, 95, 6953-6958.

Fishel, R. et al., "The Human Mutator Gene Homolog MSH2 and its Association with Hereditary Nonpolyposis Colon Cancer", *Cell*, vol. 75, pp. 1027-1038 (1993).

Prudhomme, M. et al., "Mismatch Repair Genes of *Streptococcus pneumoniae*: HexA Confers a Mutator Phenotype in *Escherichia coli* by Negative Complementation", *Journal of Bacteriology*, vol. 173, No. 22, pp. 7196-7203, (1991).

Aronshtam, Al. et al., "Dominant Negative Mutator Mutations in the mutL Gene of *Escherichia coli*", *Nucleic Acids Research*, vol. 24, No. 13, pp. 2498-2504 (1996).

Bornscheuer, U. et al., "Directed Evaluation of an Esterase for the Stereoselective Resolution of a Key Intermediate in the Synthesis of Epothilones", *Biotechnology and Bioengineering*, vol. 58, No. 5, pp. 554-559 (1998).

Loh, T. et al., "Mutational Analysis of the MutH Protein from *Escherichia coli*", *The Journal of Biological Chemistry*, vol. 275, No. 15, pp. 12113-12119 (2001).

Horst, J.P. et al., "*Escherichia coli* Mutator Genes", *Trends in Microbiology*, vol. 7, No. 1, pp. 29-36 (1999).

Fijalkowska, I. et al., "Mutants in the Exo I Motif of *Escherichia coli*DNAQ: Defective Proofreading and Inviability due to Error Catastrophe", *Proc. Natl. Acad. Sci.*, vol. 93, pp. 2856-2861 (1996).

Drotschmann, K. et al., "The *Escherichia coli* MutL Protein Stimulates Binding of Vsr and MutS to Heteroduplex DNA", Nucleic Acids Research, (1998), pp. 948-953, vol. 26, No. 4.

Upkin, Steven M., et al., "MLH3: A DNA Mismatch Repair Gene Associated with Mammalian Microsatellite Instability", Nature Genetics, (2000), pp. 27-35, vol. 24.

Lothe, Ragnhild A., PhD., "Microsatellite Instability in Human Solid Tumors, Molecular Medicine Today", (1997), pp. 61-68, (Elsevier Science Ltd.).

\* cited by examiner

PMS134 AND PMSR3 EXPRESSING BACTERIA PRODUCE KAN$^r$ PHENOTYPE

*In situ β-gal staining*

SEQUENCE LISTING

```
<160> NUMBER OF SEQ ID NOS: 26

<210> SEQ ID NO 1
<211> LENGTH: 30
<212> TYPE: DNA
<213> ORGANISM: Artificial Sequence
<220> FEATURE:
<223> OTHER INFORMATION: PCR PRIMER

<400> SEQUENCE: 1
acgcatatgg agcgagctga gagctcgagt                                          30

<210> SEQ ID NO 2
<211> LENGTH: 75
<212> TYPE: DNA
<213> ORGANISM: Artificial Sequence
<220> FEATURE:
<223> OTHER INFORMATION: PCR PRIMER

<400> SEQUENCE: 2
gaattcttat cacgtagaat cgagaccgag gagagggtta gggataggct taccagttcc        60
aaccttcgcc gatgc                                                         75

<210> SEQ ID NO 3
<211> LENGTH: 27
<212> TYPE: DNA
<213> ORGANISM: Artificial Sequence
<220> FEATURE:
<223> OTHER INFORMATION: PCR PRIMER

<400> SEQUENCE: 3
acgcatatgt gtccttggcg gcctaga                                            27
```

<210> SEQ ID NO 4
<211> LENGTH: 75
<212> TYPE: DNA
<213> ORGANISM: Artificial Sequence
<220> FEATURE:
<223> OTHER INFORMATION: PCR PRIMER

<400> SEQUENCE: 4

| | | | | | |
|---|---|---|---|---|---|
| gaattcttat | tacgtagaat | cgagaccgag | gagagggtta | gggataggct | tacccatgtg | 60 |
| tgatgtttca | gagct | | | | | 75 |

<210> SEQ ID NO 5
<211> LENGTH: 3218
<212> TYPE: DNA
<213> ORGANISM: Saccharamyces cerevisiae

<400> SEQUENCE: 5

| | | | | | |
|---|---|---|---|---|---|
| aaataggaat | gtgataccttt | ctattgcatg | caaagatagt | gtaggaggcg | ctgctattgc | 60 |
| caaagacttt | tgagaccgct | tgctgtttca | ttatagttga | ggagttctcg | aagacgagaa | 120 |
| attagcagtt | ttcggtgttt | agtaatcgcg | ctagcatgct | aggacaattt | aactgcaaaa | 180 |
| ttttgatacg | atagtgatag | taaatggaag | gtaaaaataa | catagaccta | tcaataagca | 240 |
| atgtctctca | gaataaaagc | acttgatgca | tcagtggtta | acaaaattgc | tgcaggtgag | 300 |
| atcataatat | cccccgtaaa | tgctctcaaa | gaaatgatgg | agaattccat | cgatgcgaat | 360 |
| gctacaatga | ttgatattct | agtcaaggaa | ggaggaatta | aggtacttca | aataacagat | 420 |
| aacggatctg | gaattaataa | agcagacctg | ccaatcttat | gtgagcgatt | cacgacgtcc | 480 |
| aaattacaaa | aattcgaaga | tttgagtcag | attcaaacgt | atggattccg | aggagaagct | 540 |
| ttagccagta | tctcacatgt | ggcaagagtc | acagtaacga | caaaagttaa | agaagacaga | 600 |
| tgtgcatgga | gagtttcata | tgcagaaggt | aagatgttgg | aaagccccaa | acctgttgct | 660 |
| ggaaaagacg | gtaccacgat | cctagttgaa | gaccttttttt | tcaatattcc | ttctagatta | 720 |
| agggccttga | ggtcccataa | tgatgaatac | tctaaaatat | tagatgttgt | cgggcgatac | 780 |
| gccattcatt | ccaaggacat | tggcttttct | tgtaaaaagt | tcggagactc | taattattct | 840 |
| ttatcagtta | aaccttcata | tacagtccag | gataggatta | ggactgtgtt | caataaatct | 900 |
| gtggcttcga | atttaattac | ttttcatatc | agcaaagtag | aagatttaaa | cctggaaagc | 960 |
| gttgatggaa | aggtgtgtaa | tttgaatttc | atatccaaaa | agtccatttc | attaattttt | 1020 |
| ttcattaata | atagactagt | gacatgtgat | cttctaagaa | gagctttgaa | cagcgtttac | 1080 |
| tccaattatc | tgccaaaggg | cttcagacct | tttatttatt | tgggaattgt | tatagatccg | 1140 |
| gcggctgttg | atgttaacgt | tcacccgaca | agagagagg | ttcgtttcct | gagccaagat | 1200 |
| gagatcatag | agaaaatcgc | caatcaattg | cacgccgaat | tatctgccat | tgatacttca | 1260 |
| cgtactttca | aggcttcttc | aatttcaaca | acaagccag | agtcattgat | accatttaat | 1320 |
| gacaccatag | aaagtgatag | gaataggaag | agtctccgac | aagcccaagt | ggtagagaat | 1380 |
| tcatatacga | cagccaatag | tcaactaagg | aaagcgaaaa | gacaagagaa | taaactagtc | 1440 |
| agaatagatg | cttcacaagc | taaaattacg | tcatttttat | cctcaagtca | acagttcaac | 1500 |
| tttgaaggat | cgtctacaaa | gcgacaactg | agtgaaccca | aggtaacaaa | tgtaagccac | 1560 |
| tcccaagagg | cagaaaagct | gacactaaat | gaaagcgaac | aaccgcgtga | tgccaataca | 1620 |
| atcaatgata | atgacttgaa | ggatcaacct | aagaagaaac | aaaagttggg | ggattataaa | 1680 |
| gttccaagca | ttgccgatga | cgaaaagaat | gcactcccga | tttcaaaaga | cgggtatatt | 1740 |

-continued

```
agagtaccta aggagcgagt taatgttaat cttacgagta tcaagaaatt gcgtgaaaaa    1800
gtagatgatt cgatacatcg agaactaaca gacattttg caaatttgaa ttacgttggg     1860
gttgtagatg aggaaagaag attagccgct attcagcatg acttaaagct tttttttaata   1920 gattacggat ctgtgtgcta tgagctattc tatcagattg gtttgacaga cttcgcaaac    1980
tttggtaaga taaacctaca gagtacaaat gtgtcagatg atatagtttt gtataatctc    2040
ctatcagaat ttgacgagtt aaatgacgat gcttccaaag aaaaaataat tagtaaaata    2100
tgggacatga gcagtatgct aaatgagtac tattccatag aattggtgaa tgatggtcta    2160
gataatgact taaagtctgt gaagctaaaa tctctaccac tacttttaaa aggctacatt    2220
ccatctctgg tcaagttacc attttttata tatcgcctgg gtaaagaagt tgattgggag    2280
gatgaacaag agtgtctaga tggtatttta agagagattg cattactcta tatacctgat    2340
atggttccga agtcgatac actcgatgca tcgttgtcag aagacgaaaa agcccagttt     2400
ataaatagaa aggaacacat atcctcatta ctagaacacg ttctcttccc ttgtatcaaa    2460
cgaaggttcc tggcccctag acacattctc aaggatgtcg tggaaatagc caaccttcca    2520
gatctataca aagttttttga gaggtgttaa ctttaaaacg ttttggctgt aataccaaag    2580
tttttgttta tttcctgagt gtgattgtgt ttcatttgaa agtgtatgcc ctttcctta    2640 acgattcatc cgcgagattt caaaggatat gaaatatggt tgcagttagg aaagtatgtc    2700
agaaatgtat attcggattg aaactcttct aatagttctg aagtcacttg gttccgtatt    2760
gttttcgtcc tcttcctcaa gcaacgattc ttgtctaagc ttattcaacg gtaccaaga    2820 cccgagtcct tttatgagag aaaacatttc atcatttttc aactcaatta tcttaatatc    2880
attttgtagt attttgaaaa caggatggta aaacgaatca cctgaatcta gaagctgtac    2940
cttgtcccat aaaagtttta atttactgag cctttcggtc aagtaaacta gtttatctag    3000
ttttgaaccg aatattgtgg gcagatttgc agtaagttca gttagatcta ctaaaagttg    3060
tttgacagca gccgattcca caaaaatttg gtaaaaggag atgaaagaga cctcgcgcgt    3120
aatggtttgc atcaccatcg gatgtctgtt gaaaaactca ctttttgcat ggaagttatt    3180
aacaataaga ctaatgatta ccttagaata atgtataa                            3218
```

<210> SEQ ID NO 6
<211> LENGTH: 3056
<212> TYPE: DNA
<213> ORGANISM: Mus musculus

<400> SEQUENCE: 6

```
gaattccggt gaaggtcctg aagaatttcc agattcctga gtatcattgg aggagacaga     60
taacctgtcg tcaggtaacg atggtgtata tgcaacagaa atgggtgttc ctggagacgc    120 gtctttccc gagagcggca ccgcaactct cccgcggtga ctgtgactgg aggagtcctg     180
catccatgga gcaaaccgaa ggcgtgagta cagaatgtgc taaggccatc aagcctattg    240
atgggaagtc agtccatcaa atttgttctg ggcaggtgat actcagttta agcaccgctg    300
tgaaggagtt gatagaaaat agtgtagatg ctggtgctac tactattgat ctaaggctta    360
aagactatgg ggtggacctc attgaagttt cagacaatgg atgtggggta gaagaagaaa    420
actttgaagg tctagctctg aaacatcaca catctaagat tcaagagttt gccgacctca    480
cgcaggttga aactttcggc tttcgggggg aagctctgag ctctctgtgt gcactaagtg    540
atgtcactat atctacctgc cacgggtctg caagcgttgg gactcgactg gtgtttgacc    600
```

-continued

```
ataatgggaa aatcacccag aaaactccct accccgacc taaaggaacc acagtcagtg    660
tgcagcactt attttataca ctacccgtgc gttacaaaga gtttcagagg aacattaaaa    720
aggagtattc caaaatggtg caggtcttac aggcgtactg tatcatctca gcaggcgtcc    780
gtgtaagctg cactaatcag ctcggacagg ggaagcggca cgctgtggtg tgcacaagcg    840
gcacgtctgg catgaaggaa aatatcgggt ctgtgtttgg ccagaagcag ttgcaaagcc    900
tcattccttt tgttcagctg ccccctagtg acgctgtgtg tgaagagtac ggcctgagca    960
cttcaggacg ccacaaaacc ttttctacgt ttcgggcttc atttcacagt gcacgcacgg   1020
cgccgggagg agtgcaacag acaggcagtt tttcttcatc aatcagaggc cctgtgaccc   1080
agcaaaggtc tctaagcttg tcaatgaggt tttatcacat gtataaccgg catcagtacc   1140
catttgtcgt ccttaacgtt tccgttgact cagaatgtgt ggatattaat gtaactccag   1200
ataaaaggca aattctacta caagaagaga agctattgct ggccgttta aagacctcct    1260 tgataggaat gtttgacagt gatgcaaaca agcttaatgt caaccagcag ccactgctag   1320
atgttgaagg taacttagta aagctgcata ctgcagaact agaaaagcct gtgccaggaa   1380
agcaagataa ctctccttca ctgaagagca cagcagacga gaaagggta gcatccatct    1440 ccaggctgag agaggccttt tctcttcatc ctactaaaga gatcaagtct aggggtccag   1500
agactgctga actgacacgg agttttccaa gtgagaaaag gggcgtgtta tcctcttatc   1560
cttcagacgt catctcttac agaggcctcc gtggctcgca ggacaaattg gtgagtccca   1620
cggacagccc tggtgactgt atggacagag agaaaataga aaaagactca gggctcagca   1680
gcacctcagc tggctctgag aagagttca gcaccccaga agtggccagt agctttagca    1740
gtgactataa cgtgagctcc ctagaagaca gaccttctca ggaaaccata aactgtggtg   1800
acctggactg ccgtcctcca ggtacaggac agtccttgaa gccagaagac catggatatc   1860
aatgcaaagc tctacctcta gctcgtctgt cacccacaaa tgccaagcgc ttcaagacag   1920
aggaaagacc ctcaaatgtc aacatttctc aaagattgcc tggtcctcag agcacctcag   1980
cagctgaggt cgatgtagcc ataaaaatga ataagagaat cgtgctcctc gagttctctc   2040
tgagttctct agctaagcga atgaagcagt tacagcacct aaaggcgcag aacaaacatg   2100
aactgagtta cagaaaattt agggccaaga tttgccctgg agaaaaccaa gcagcagaag   2160
atgaactcag aaaagagatt agtaaatcga tgtttgcaga gatggagatc ttgggtcagt   2220
ttaacctggg atttatagta accaaactga agaggacct cttcctggtg gaccagcatg    2280
ctgcggatga gaagtacaac tttgagatgc tgcagcagca cacggtgctc caggcgcaga   2340
ggctcatcac acccccagact ctgaacttaa ctgctgtcaa tgaagctgta ctgatagaaa   2400
atctggaaat attcagaaag aatggcttg actttgtcat tgatgaggat gctccagtca    2460
ctgaaagggc taaattgatt tccttaccaa ctagtaaaaa ctggaccttt ggaccccaag   2520
atatagatga actgatcttt atgttaagtg acagccctgg ggtcatgtgc cggccctcac   2580
gagtcagaca gatgtttgct tccagagcct gtcggaagtc agtgatgatt ggaacggcgc   2640
tcaatgcgag cgagatgaag aagctcatca cccacatggg tgagatggac cacccctgga   2700
actgccccca cggcaggcca accatgaggc acgttgccaa tctggatgtc atctctcaga   2760
actgacacac cccttgtagc atagagttta ttacagattg ttcggtttgc aaagagaagg   2820
ttttaagtaa tctgattatc gttgtacaaa aattagcatg ctgctttaat gtactggatc   2880
catttaaaag cagtgttaag gcaggcatga tggagtgttc ctctagctca gctacttggg   2940
tgatccggtg ggagctcatg tgagcccagg actttgagac cactccgagc cacattcatg   3000
```

-continued

```
agactcaatt caaggacaaa aaaaaaaaga tatttttgaa gccttttaaa aaaaaa        3056
```

<210> SEQ ID NO 7
<211> LENGTH: 2771
<212> TYPE: DNA
<213> ORGANISM: Homo sapiens

<400> SEQUENCE: 7

```
cgaggcggat cgggtgttgc atccatggag cgagctgaga gctcgagtac agaacctgct     60
aaggccatca aacctattga tcggaagtca gtccatcaga tttgctctgg gcaggtggta    120
ctgagtctaa gcactgcggt aaaggagtta gtagaaaaca gtctggatgc tggtgccact    180
aatattgatc taaagcttaa ggactatgga gtggatctta ttgaagtttc agacaatgga    240
tgtggggtag aagaagaaaa cttcgaaggc ttaactctga acatcacac atctaagatt     300
caagagtttg ccgacctaac tcaggttgaa acttttggct ttcgggggga agctctgagc    360
tcactttgtg cactgagcga tgtcaccatt tctacctgcc acgcatcggc gaaggttgga    420
actcgactga tgtttgatca aatgggaaa attatccaga aaacccccta ccccgcccc     480
agagggacca cagtcagcgt gcagcagtta ttttccacac tacctgtgcg ccataaggaa    540
tttcaaagga atattaagaa ggagtatgcc aaaatggtcc aggtcttaca tgcatactgt    600
atcatttcag caggcatccg tgtaagttgc accaatcagc ttggacaagg aaaacgacag    660
cctgtggtat gcacaggtgg aagccccagc ataaaggaaa atatcggctc tgtgtttggg    720
cagaagcagt tgcaaagcct cattccttt ggtcagctgc cccctagtga ctccgtgtgt     780
gaagagtacg gtttgagctg ttcggatgct ctgcataatc ttttttacat ctcaggtttc    840
atttcacaat gcacgcatgg agttggaagg agttcaacag acagacagtt tttctttatc    900
aaccggcggc cttgtgaccc agcaaggtc tgcagactcg tgaatgaggt ctaccacatg     960
tataatcgac accagtatcc atttgttgtt cttaacattt ctgttgattc agaatgcgtt   1020
gatatcaatg ttactccaga taaaaggcaa attttgctac aagaggaaaa gcttttgttg   1080
gcagttttaa agacctcttt gataggaatg tttgatagtg atgtcaacaa gctaaatgtc   1140
agtcagcagc cactgctgga tgttgaaggt aacttaataa aaatgcatgc agcggatttg   1200
gaaaagccca tggtagaaaa gcaggatcaa tccccttcat taaggactgg agaagaaaaa   1260
aaagacgtgt ccatttccag actgcgagag gccttttctc ttcgtcacac aacagagaac   1320
aagcctcaca gcccaaagac tccagaacca agaaggagcc ctctaggaca gaaaaggggt   1380
atgctgtctt ctagcacttc aggtgccatc tctgacaaag gcgtcctgag acctcagaaa   1440
gaggcagtga gttccagtca cggacccagt gaccctacgg acagagcgga ggtggagaag   1500
gactcggggc acggcagcac ttccgtggat tctgaggggt tcagcatccc agacacgggc   1560
agtcactgca gcagcgagta tgcggccagc tccccagggg acaggggctc gcaggaacat   1620
gtggactctc aggagaaagc gcctgaaact gacgactctt tttcagatgt ggactgccat   1680
tcaaaccagg aagataccgg atgtaaattt cgagttttgc ctcagccaac taatctcgca   1740
accccaaaca caaagcgttt taaaaagaa gaaattcttt ccagttctga catttgtcaa   1800
aagttagtaa atactcagga catgtcagcc tctcaggttg atgtagctgt gaaaattaat   1860
aagaaagttg tgcccctgga cttttctatg agttctttag ctaaacgaat aaagcagtta   1920
catcatgaag cacagcaaag tgaaggggaa cagaattaca ggaagtttag ggcaaagatt   1980
tgtcctggag aaaatcaagc agccgaagat gaactaagaa aagagataag taaaacgatg   2040
```

-continued

| | |
|---|---|
| tttgcagaaa tggaaatcat tggtcagttt aacctgggat ttataataac caaactgaat | 2100 |
| gaggatatct tcatagtgga ccagcatgcc acggacgaga agtataactt cgagatgctg | 2160 |
| cagcagcaca ccgtgctcca ggggcagagg ctcatagcac ctcagactct caacttaact | 2220 |
| gctgttaatg aagctgttct gatagaaaat ctggaaatat ttagaaagaa tggctttgat | 2280 |
| tttgttatcg atgaaaatgc tccagtcact gaaagggcta aactgatttc cttgccaact | 2340 |
| agtaaaaact ggaccttcgg accccaggac gtcgatgaac tgatcttcat gctgagcgac | 2400 |
| agccctgggg tcatgtgccg gccttcccga gtcaagcaga tgtttgcctc cagagcctgc | 2460 |
| cggaagtcgg tgatgattgg gactgctctt aacacaagcg agatgaagaa actgatcacc | 2520 |
| cacatggggg agatggacca cccctggaac tgtccccatg aaggccaac catgagacac | 2580 |
| atcgccaacc tgggtgtcat ttctcagaac tgaccgtagt cactgtatgg aataattggt | 2640 |
| tttatcgcag atttttatgt tttgaaagac agagtcttca ctaaccttt ttgttttaaa | 2700 |
| atgaaacctg ctacttaaaa aaaatacaca tcacacccat ttaaaagtga tcttgagaac | 2760 |
| cttttcaaac c | 2771 |

<210> SEQ ID NO 8
<211> LENGTH: 3063
<212> TYPE: DNA
<213> ORGANISM: Homo sapiens

<400> SEQUENCE: 8

| | |
|---|---|
| ggcacgagtg gctgcttgcg gctagtggat ggtaattgcc tgcctcgcgc tagcagcaag | 60 |
| ctgctctgtt aaaagcgaaa atgaaacaat tgcctgcggc aacagttcga ctcctttcaa | 120 |
| gttctcagat catcacttcg gtggtcagtg ttgtaaaaga gcttattgaa aactccttgg | 180 |
| atgctggtgc cacaagcgta gatgttaaac tggagaacta tggatttgat aaaattgagg | 240 |
| tgcgagataa cggggagggt atcaaggctg ttgatgcacc tgtaatggca atgaagtact | 300 |
| acacctcaaa aataaatagt catgaagatc ttgaaaattt gacaacttac ggttttcgtg | 360 |
| gagaagcctt ggggtcaatt tgttgtatag ctgaggtttt aattacaaca agaacgctg | 420 |
| ctgataattt tagcacccag tatgttttag atggcagtgg ccacatactt tctcagaaac | 480 |
| cttcacatct tggtcaaggt acaactgtaa ctgctttaag attatttaag aatctacctg | 540 |
| taagaaagca gttttactca actgcaaaaa aatgtaaaga tgaaataaaa aagatccaag | 600 |
| atctcctcat gagctttggt atccttaaac ctgacttaag gattgtcttt gtacataaca | 660 |
| aggcagttat ttggcagaaa agcagagtat cagatcacaa gatggctctc atgtcagttc | 720 |
| tggggactgc tgttatgaac aatatggaat cctttcagta ccactctgaa gaatctcaga | 780 |
| tttatctcag tggatttctt ccaaagtgtg atgcagacca ctctttcact agtctttcaa | 840 |
| caccagaaag aagtttcatc ttcataaaca gtcgaccagt acatcaaaaa gatatcttaa | 900 |
| agttaatccg acatcattac aatctgaaat gcctaaagga atctactcgt ttgtatcctg | 960 |
| ttttcttttct gaaatcgat gttcctacag ctgatgttga tgtaaattta acaccagata | 1020 |
| aaagccaagt attattacaa ataaggaat ctgtttttaat tgctcttgaa atctgatga | 1080 |
| cgacttgtta tggaccatta cctagtacaa attcttatga aataataaa acagatgttt | 1140 |
| ccgcagctga catcgttctt agtaaaacag cagaaacaga tgtgcttttt aataaagtgg | 1200 |
| aatcatctgg aaagaattat tcaaatgttg atacttcagt cattccattc caaaatgata | 1260 |
| tgcataatga tgaatctgga aaaaacactg atgattgttt aaatcaccag ataagtattg | 1320 |
| gtgactttgg ttatggtcat tgtagtagtg aaatttctaa cattgataaa aacactaaga | 1380 |

-continued

| | |
|---|---|
| atgcatttca ggacatttca atgagtaatg tatcatggga gaactctcag acggaatata | 1440 |
| gtaaaacttg ttttataagt tccgttaagc acacccagtc agaaaatggc aataaagacc | 1500 |
| atatagatga gagtggggaa aatgaggaag aagcaggtct tgaaaactct tcggaaattt | 1560 |
| ctgcagatga gtggagcagg ggaaatatac ttaaaaattc agtgggagag aatattgaac | 1620 |
| ctgtgaaaat tttagtgcct gaaaaaagtt taccatgtaa agtaagtaat aataattatc | 1680 |
| caatccctga acaaatgaat cttaatgaag attcatgtaa caaaaaatca aatgtaatag | 1740 |
| ataataaatc tggaaaagtt acagcttatg atttacttag caatcgagta atcaagaaac | 1800 |
| ccatgtcagc aagtgctctt tttgttcaag atcatcgtcc tcagtttctc atagaaaatc | 1860 |
| ctaagactag tttagaggat gcaacactac aaattgaaga actgtggaag acattgagtg | 1920 |
| aagaggaaaa actgaaatat aagagaagg ctactaaaga cttggaacga tacaatagtc | 1980 |
| aaatgaagag agccattgaa caggagtcac aaatgtcact aaaagatggc agaaaaaaga | 2040 |
| taaacccac cagcgcatgg aatttggccc agaagcacaa gttaaaaacc tcattatcta | 2100 |
| atcaaccaaa acttgatgaa ctccttcagt cccaaattga aaaagaagg agtcaaaata | 2160 |
| ttaaaatggt acagatcccc ttttctatga aaaacttaaa aataaattt aagaaacaaa | 2220 |
| acaaagttga cttagaagag aaggatgaac cttgcttgat ccacaatctc aggtttcctg | 2280 |
| atgcatggct aatgacatcc aaaacagagg taatgttatt aaatccatat agagtagaag | 2340 |
| aagccctgct atttaaaaga cttcttgaga atcataaact tcctgcagag ccactggaaa | 2400 |
| agccaattat gttaacagag agtctttta atggatctca ttatttagac gttttatata | 2460 |
| aaatgacagc agatgaccaa agatacagtg gatcaactta cctgtctgat cctcgtctta | 2520 |
| cagcgaatgg tttcaagata aaattgatac caggagtttc aattactgaa aattacttgg | 2580 |
| aaatagaagg aatggctaat tgtctcccat tctatggagt agcagattta aaagaaattc | 2640 |
| ttaatgctat attaaacaga aatgcaaagg aagtttatga atgtagacct cgcaaagtga | 2700 |
| taagttattt agagggagaa gcagtgcgtc tatccagaca attacccatg tacttatcaa | 2760 |
| aagaggacat ccaagacatt atctacagaa tgaagcacca gtttggaaat gaaattaaag | 2820 |
| agtgtgttca tggtcgccca ttttttcatc atttaaccta tcttccagaa actacatgat | 2880 |
| taaatatgtt taagaagatt agttaccatt gaaattggtt ctgtcataaa acagcatgag | 2940 |
| tctggtttta aattatcttt gtattatgtg tcacatggtt attttttaaa tgaggattca | 3000 |
| ctgacttgtt tttatattga aaaaagttcc acgtattgta gaaaacgtaa ataaactaat | 3060 |
| aac | 3063 |

<210> SEQ ID NO 9
<211> LENGTH: 3145
<212> TYPE: DNA
<213> ORGANISM: Homo sapiens

<400> SEQUENCE: 9

| | |
|---|---|
| ggcgggaaac agcttagtgg gtgtggggtc gcgcattttc ttcaaccagg aggtgaggag | 60 |
| gtttcgacat ggcggtgcag ccgaaggaga cgctgcagtt ggagagcgcg gccgaggtcg | 120 |
| gcttcgtgcg cttctttcag ggcatgccgg agaagccgac caccacagtg cgccttttcg | 180 |
| accggggcga cttctatacg gcgcacgcg aggacgcgct gctggccgcc gggaggtgt | 240 |
| tcaagaccca gggggtgatc aagtacatgg ggcggcagg agcaaagaat ctgcagagtg | 300 |
| ttgtgcttag taaaatgaat tttgaatctt ttgtaaaaga tcttcttctg gttcgtcagt | 360 |

-continued

```
atagagttga agtttataag aatagagctg gaaataaggc atccaaggag aatgattggt    420
atttggcata taaggcttct cctggcaatc tctctcagtt tgaagacatt ctctttggta    480
acaatgatat gtcagcttcc attggtgttg tgggtgttaa aatgtccgca gttgatggcc    540
agagacaggt tggagttggg tatgtggatt ccatacagag gaaactagga ctgtgtgaat    600
tccctgataa tgatcagttc tccaatcttg aggctctcct catccagatt ggaccaaagg    660
aatgtgtttt acccggagga gagactgctg gagacatggg gaaactgaga cagataattc    720
aaagaggagg aattctgatc acagaaagaa aaaagctga cttttccaca aaagacattt    780
atcaggacct caaccggttg ttgaaaggca aaaagggaga gcagatgaat agtgctgtat    840
tgccagaaat ggagaatcag gttgcagttt catcactgtc tgcggtaatc aagttttag    900 aactcttatc agatgattcc aactttggac agtttgaact gactactttt gacttcagcc    960
agtatatgaa attggatatt gcagcagtca gagcccttaa cctttttcag ggttctgttg    1020
aagataccac tggctctcag tctctggctg ccttgctgaa taagtgtaaa acccctcaag    1080
gacaaagact tgttaaccag tggattaagc agcctctcat ggataagaac agaatagagg    1140
agagattgaa tttagtggaa gcttttgtag aagatgcaga attgaggcag actttacaag    1200
aagatttact tcgtcgattc ccagatctta accgacttgc caagaagttt caaagacaag    1260
cagcaaactt acaagattgt taccgactct atcagggtat aaatcaacta cctaatgtta    1320
tacaggctct ggaaaaacat gaaggaaaac accagaaatt attgttggca gtttttgtga    1380
ctcctcttac tgatcttcgt tctgacttct ccaagtttca ggaaatgata gaaacaactt    1440
tagatatgga tcaggtggaa aaccatgaat tccttgtaaa accttcattt gatcctaatc    1500
tcagtgaatt aagagaaata atgaatgact tggaaaagaa gatgcagtca acattaataa    1560
gtgcagccag agatcttggc ttggaccctg gcaaacagat taaactggat tccagtgcac    1620
agtttggata ttactttcgt gtaacctgta aggaagaaaa agtccttcgt aacaataaaa    1680
actttagtac tgtagatatc cagaagaatg gtgttaaatt taccaacagc aaattgactt    1740
ctttaaatga gagtatacc aaaaataaaa cagaatatga agaagcccag gatgccattg    1800
ttaaagaaat tgtcaatatt tcttcaggct atgtagaacc aatgcagaca ctcaatgatg    1860
tgttagctca gctagatgct gttgtcagct ttgctcacgt gtcaaatgga gcacctgttc    1920
catatgtacg accagccatt ttggagaaag gacaaggaag aattatatta aaagcatcca    1980
ggcatgcttg tgttgaagtt caagatgaaa ttgcatttat tcctaatgac gtatactttg    2040
aaaaagataa acagatgttc cacatcatta ctggccccaa tatgggaggt aaatcaacat    2100
atattcgaca aactggggtg atagtactca tggcccaaat tgggtgtttt gtgccatgtg    2160
agtcagcaga agtgtccatt gtggactgca tcttagcccg agtaggggct ggtgacagtc    2220
aattgaaagg agtctccacg ttcatggctg aaatgttgga aactgcttct atcctcaggt    2280
ctgcaaccaa agattcatta ataatcatag atgaattggg aagaggaact tctacctacg    2340
atggatttgg gttagcatgg gctatatcag aatacattgc aacaaagatt ggtgcttttt    2400
gcatgtttgc aacccatttt catgaactta ctgccttggc caatcagata ccaactgtta    2460
ataatctaca tgtcacagca ctcaccactg aagagacctt aactatgctt tatcaggtga    2520
agaaaggtgt ctgtgatcaa agttttggga ttcatgttgc agagcttgct aatttccta    2580 agcatgtaat agagtgtgct aaacagaaag ccctggaact tgaggagttt cagtatattg    2640
gagaatcgca aggatatgat atcatggaac cagcagcaaa gaagtgctat ctggaaagag    2700
agcaaggtga aaaaattatt caggagttcc tgtccaaggt gaaacaaatg ccctttactg    2760
```

-continued

```
aaatgtcaga agaaaacatc acaataaagt taaaacagct aaaagctgaa gtaatagcaa    2820
agaataatag ctttgtaaat gaaatcattt cacgaataaa agttactacg tgaaaaatcc    2880
cagtaatgga atgaaggtaa tattgataag ctattgtctg taatagtttt atattgtttt    2940
atattaaccc ttttccata gtgttaactg tcagtgccca tgggctatca acttaataag     3000
atatttagta atattttact ttgaggacat tttcaaagat ttttattttg aaaaatgaga    3060
gctgtaactg aggactgttt gcaattgaca taggcaataa taagtgatgt gctgaatttt    3120
ataaataaaa tcatgtagtt tgtgg                                         3145
```

<210> SEQ ID NO 10
<211> LENGTH: 2484
<212> TYPE: DNA
<213> ORGANISM: Homo sapiens

<400> SEQUENCE: 10

```
cttggctctt ctggcgccaa aatgtcgttc gtggcagggg ttattcggcg gctggacgag    60
acagtggtga accgcatcgc ggcgggggaa gttatccagc ggccagctaa tgctatcaaa    120
gagatgattg agaactgttt agatgcaaaa tccacaagta ttcaagtgat tgttaaagag    180
ggaggcctga gttgattca gatccaagac aatggcaccg ggatcaggaa agaagatctg    240
gatattgtat gtgaaaggtt cactactagt aaactgcagt cctttgagga tttagccagt    300
atttctacct atggctttcg aggtgaggct ttggccagca taagccatgt ggctcatgtt    360
actattacaa cgaaaacagc tgatggaaag tgtgcataca gagcaagtta ctcagatgga    420
aaactgaaag cccctcctaa accatgtgct ggcaatcaag ggacccagat cacggtggag    480 gaccttttt acaacatagc cacgaggaga aaagctttaa aaaatccaag tgaagaatat    540
gggaaatttt tggaagttgt tggcaggtat tcagtacaca atgcaggcat tagtttctca    600
gttaaaaaac aaggagagac agtagctgat gttaggacac tacccaatgc ctcaaccgtg    660
gacaatattc gctccatctt tggaaatgct gttagtcgag aactgataga aattggatgt    720
gaggataaaa ccctagcctt caaaatgaat ggttacatat ccaatgcaaa ctactcagtg    780
aagaagtgca tcttcttact cttcatcaac catcgtctgg tagaatcaac ttccttgaga    840
aaagccatag aaacagtgta tgcagcctat ttgcccaaaa acacacaccc attcctgtac    900
ctcagtttag aaatcagtcc ccagaatgtg atgttaatg tgcaccccac aaagcatgaa    960
gttcacttcc tgcacgagga gagcatcctg agcgggtgc agcagcacat cgagagcaag    1020
ctcctgggct ccaattcctc caggatgtac ttcacccaga ctttgctacc aggacttgct    1080
ggcccctctg gggagatggt taaatccaca acaagtctga cctcgtcttc tacttctgga    1140
agtagtgata aggtctatgc ccaccagatg gttcgtacag attcccggga acagaagctt    1200
gatgcatttc tgcagcctct gagcaaaccc ctgtccagtc agcccaggc cattgtcaca    1260 gaggataaga cagatatttc tagtggcagg gctaggcagc aagatgagga gatgcttgaa    1320
ctcccagccc ctgctgaagt ggctgccaaa aatcagagct ggagggga tacaacaaag    1380 gggacttcag aaatgtcaga agagagga cctacttcca gcaaccccag aaagagacat    1440
cgggaagatt ctgatgtgga aatggtggaa gatgattccc gaaaggaaat gactgcagct    1500 tgtaccccc ggagaaggat cattaacctc actagtgttt tgagtctcca ggaagaaatt    1560
aatgagcagg gacatgaggt tctccgggag atgttgcata accactcctt cgtgggctgt    1620
gtgaatcctc agtgggcctt ggcacagcat caaaccaagt tataccttct caacaccacc    1680
```

| | |
|---|---:|
| aagcttagtg aagaactgtt ctaccagata ctcatttatg attttgccaa ttttggtgtt | 1740 |
| ctcaggttat cggagccagc accgctcttt gaccttgcca tgcttgcctt agatagtcca | 1800 |
| gagagtggct ggacagagga agatggtccc aaagaaggac ttgctgaata cattgttgag | 1860 |
| tttctgaaga agaaggctga gatgcttgca gactatttct ctttggaaat tgatgaggaa | 1920 |
| gggaacctga ttggattacc ccttctgatt gacaactatg tgcccccttt ggagggactg | 1980 |
| cctatcttca ttcttcgact agccactgag gtgaattggg acgaagaaaa ggaatgtttt | 2040 |
| gaaagcctca gtaaagaatg cgctatgttc tattccatcc ggaagcagta catatctgag | 2100 |
| gagtcgaccc tctcaggcca gcagagtgaa gtgcctggct ccattccaaa ctcctggaag | 2160 |
| tggactgtgg aacacattgt ctataaagcc ttgcgctcac acattctgcc tcctaaacat | 2220 |
| ttcacagaag atggaaatat cctgcagctt gctaacctgc ctgatctata caaagtcttt | 2280 |
| gagaggtgtt aaatatggtt atttatgcac tgtgggatgt gttcttcttt ctctgtattc | 2340 |
| cgatacaaag tgttgtatca aagtgtgata tacaaagtgt accaacataa gtgttggtag | 2400 |
| cacttaagac ttatacttgc cttctgatag tattcctttta tacacagtgg attgattata | 2460 |
| aataaataga tgtgtcttaa cata | 2484 |

<210> SEQ ID NO 11
<211> LENGTH: 426
<212> TYPE: DNA
<213> ORGANISM: Homo sapiens

<400> SEQUENCE: 11

| | |
|---|---:|
| cgaggcggat cgggtgttgc atccatggag cgagctgaga gctcgagtac agaacctgct | 60 |
| aaggccatca aacctattga tcggaagtca gtccatcaga tttgctctgg gcaggtggta | 120 |
| ctgagtctaa gcactgcggt aaaggagtta gtagaaaaca gtctggatgc tggtgccact | 180 |
| aatattgatc taaagcttaa ggactatgga gtggatctta ttgaagtttc agacaatgga | 240 |
| tgtgggtag aagaagaaaa cttcgaaggc ttaactctga acatcacac atctaagatt | 300 |
| caagagtttg ccgacctaac tcaggttgaa acttttggct tcggggggga agctctgagc | 360 |
| tcactttgtg cactgagcga tgtcaccatt tctacctgcc acgcatcggc gaaggttgga | 420 |
| acttga | 426 |

<210> SEQ ID NO 12
<211> LENGTH: 1408
<212> TYPE: DNA
<213> ORGANISM: Homo sapiens

<400> SEQUENCE: 12

| | |
|---|---:|
| ggcgctccta cctgcaagtg gctagtgcca agtgctgggc cgccgctcct gccgtgcatg | 60 |
| ttggggagcc agtacatgca ggtgggctcc acacggagag gggcgcagac ccggtgacag | 120 |
| ggctttacct ggtacatcgg catggcgcaa ccaaagcaag agagggtggc gcgtgccaga | 180 |
| caccaacggt cggaaaccgc cagacaccaa cggtcggaaa ccgccaagac accaacgctc | 240 |
| ggaaaccgcc agacaccaac gctcggaaac cgccagacac caaggctcgg aatccacgcc | 300 |
| aggccacgac ggagggcgac tacctcccttt ctgaccctgc tgctggcgtt cggaaaaaac | 360 |
| gcagtccggt gtgctctgat tggtccaggc tctttgacgt cacggactcg acctttgaca | 420 |
| gagccactag gcgaaaagga gagacgggaa gtatttttc cgccccgccc ggaaagggtg | 480 |
| gagcacaacg tcgaaagcag ccgttgggag cccaggaggc gggcgcctg tgggagccgt | 540 |
| ggagggaact ttcccagtcc ccgaggcgga tccggtgttg catccttgga gcgagctgag | 600 |

-continued

| | | |
|---|---|---|
| aactcgagta cagaacctgc taaggccatc aaacctattg atcggaagtc agtccatcag | 660 | |
| atttgctctg ggccggtggt accgagtcta aggccgaatg cggtgaagga gttagtagaa | 720 | |
| aacagtctgg atgctggtgc cactaatgtt gatctaaagc ttaaggacta tggagtggat | 780 | |
| ctcattgaag tttcaggcaa tggatgtggg gtagaagaag aaaacttcga aggctttact | 840 | |
| ctgaaacatc acacatgtaa gattcaagag tttgccgacc taactcaggt ggaaactttt | 900 | |
| ggctttcggg gggaagctct gagctcactt tgtgcactga gtgatgtcac catttctacc | 960 | |
| tgccgtgtat cagcgaaggt tgggactcga ctggtgtttg atcactatgg gaaaatcatc | 1020 | |
| cagaaaaccc cctaccccg ccccagaggg atgacagtca gcgtgaagca gttatttttct | 1080 | |
| acgctacctg tgcaccataa agaatttcaa aggaatatta agaagaaacg tgcctgcttc | 1140 | |
| cccttcgcct tctgccgtga ttgtcagttt cctgaggcct ccccagccat gcttcctgta | 1200 | |
| cagcctgtag aactgactcc tagaagtacc ccaccccacc cctgctcctt ggaggacaac | 1260 | |
| gtgatcactg tattcagctc tgtcaagaat ggtccaggtt cttctagatg atctgcacaa | 1320 | |
| atggttcctc tcctccttcc tgatgtctgc cattagcatt ggaataaagt tcctgctgaa | 1380 | |
| aatccaaaaa aaaaaaaaaa aaaaaaaa | 1408 | |

<210> SEQ ID NO 13
<211> LENGTH: 1785
<212> TYPE: DNA
<213> ORGANISM: Homo sapiens

<400> SEQUENCE: 13

| | | |
|---|---|---|
| tttttagaaa ctgatgttta ttttccatca accatttttc catgctgctt aagagaatat | 60 | |
| gcaagaacag cttaagacca gtcagtggtt gctcctaccc attcagtggc ctgagcagtg | 120 | |
| gggagctgca gaccagtctt ccgtggcagg ctgagcgctc cagtcttcag tagggaattg | 180 | |
| ctgaataggc acagagggca cctgtacacc ttcagaccag tctgcaacct caggctgagt | 240 | |
| agcagtgaac tcaggagcgg gagcagtcca ttcaccctga aattcctcct tggtcactgc | 300 | |
| cttctcagca gcgcctgct cttctttttc aatctcttca ggatctctgt agaagtacag | 360 | |
| atcaggcatg acctcccatg ggtgttcacg ggaaatggtg ccacgcatgc gcagaacttc | 420 | |
| ccgagccagc atccaccaca ttaaacccac tgagtgagct cccttgttgt tgcatgggat | 480 | |
| ggcaatgtcc acatagcgca gaggagaatc tgtgttacac agcgcaatgg taggtaggtt | 540 | |
| aacataagat gcctccgtga gaggcgaagg ggcggcggga cccgggcctg gcccgtatgt | 600 | |
| gtccttggcg gcctagacta ggccgtcgct gtatggtgag ccccagggag gcggatctgg | 660 | |
| gcccccagaa ggacacccgc ctggatttgc cccgtagccc ggcccgggcc cctcgggagc | 720 | |
| agaacagcct tggtgaggtg gacaggaggg gacctcgcga gcagacgcgc gcgccagcga | 780 | |
| cagcagcccc gccccggcct ctcgggagcc gggggcaga ggctgcggag ccccaggagg | 840 | |
| gtctatcagc cacagtctct gcatgtttcc aagagcaaca ggaaatgaac acattgcagg | 900 | |
| ggccagtgtc attcaaagat gtggctgtgg atttcaccca ggaggagtgg cggcaactgg | 960 | |
| accctgatga gaagatagca tacgggatg tgatgttgga gaactacagc catctagttt | 1020 | |
| ctgtggggta tgattatcac caagccaaac atcatcatgg agtggaggtg aaggaagtgg | 1080 | |
| agcagggaga ggagccgtgg ataatggaag gtgaatttcc atgtcaacat agtccagaac | 1140 | |
| ctgctaaggc catcaaacct attgatcgga agtcagtcca tcagatttgc tctgggccag | 1200 | |
| tggtactgag tctaagcact gcagtgaagg agttagtaga aaacagtctg gatgctggtg | 1260 | |

-continued

```
ccactaatat tgatctaaag cttaaggact atggagtgga tctcattgaa gtttcagaca   1320
atggatgtgg ggtagaagaa gaaaactttg aaggcttaat ctctttcagc tctgaaacat   1380
cacacatgta agattcaaga gtttgccgac ctaactgaag ttgaaacttt cggttttcag   1440
ggggaagctc tgagctcact gtgtgcactg agcgatgtca ccatttctac ctgccacgcg   1500
ttggtgaagg ttgggactcg actggtgttt gatcacgatg ggaaaatcat ccaggaaacc   1560 ccctacccccc accccagagg gaccacagtc agcgtgaagc agttattttc tacgctacct   1620
gtgcgccata aggaatttca aggaatatt aagaagacgt gcctgcttcc ccttcgcctt   1680
ctgccgtgat tgtcagtttc ctgaggcctc cccagccatg cttcctgtac agcctgcaga   1740
actgtgagtc aattaaacct cttttcttca taaattaaaa aaaaa             1785
```

<210> SEQ ID NO 14
<211> LENGTH: 795
<212> TYPE: DNA
<213> ORGANISM: Homo sapiens

<400> SEQUENCE: 14

```
atgtgtcctt gcggcctag actaggccgt cgctgtatgg tgagccccag ggaggcggat     60
ctgggccccc agaaggacac ccgcctggat ttgccccgta gcccggcccg ggcccctcgg    120
gagcagaaca gccttggtga ggtggacagg aggggacctc gcgagcagac gcgcgcgcca    180
gcgacagcag ccccgccccg gcctctcggg agccgggggg cagaggctgc ggagccccag    240
gagggtctat cagccacagt ctctgcatgt ttccaagagc aacaggaaat gaacacattg    300
caggggccag tgtcattcaa agatgtggct gtggatttca cccaggagga gtggcggcaa    360
ctggaccctg atgagaagat agcatacggg gatgtgatgt tggagaacta cagccatcta    420
gtttctgtgg ggtatgatta tcaccaagcc aaacatcatc atggagtgga ggtgaaggaa    480
gtggagcagg gagaggagcc gtggataatg aaggtgaatt tccatgtcca acatagtcca    540
gaacctgcta aggccatcaa acctattgat cggaagtcag tccatcagat ttgctctggg    600
ccagtggtac tgagtctaag cactgcagtg aaggagttag tagaaaacag tctggatgct    660
ggtgccacta atattgatct aaagcttaag gactatggag tggatctcat tgaagtttca    720
gacaatggat gtggggtaga agaagaaaac tttgaaggct taatctcttt cagctctgaa    780
acatcacaca tgtaa                                                    795
```

<210> SEQ ID NO 15
<211> LENGTH: 769
<212> TYPE: PRT
<213> ORGANISM: Saccharamyces cerevisiae

<400> SEQUENCE: 15

```
Met Ser Leu Arg Ile Lys Ala Leu Asp Ala Ser Val Val Asn Lys Ile
 1               5                  10                  15

Ala Ala Gly Glu Ile Ile Ser Pro Val Asn Ala Leu Lys Glu Met
                20                  25                  30

Met Glu Asn Ser Ile Asp Ala Asn Ala Thr Met Ile Asp Ile Leu Val
            35                  40                  45

Lys Glu Gly Gly Ile Lys Val Leu Gln Ile Thr Asp Asn Gly Ser Gly
        50                  55                  60

Ile Asn Lys Ala Asp Leu Pro Ile Leu Cys Glu Arg Phe Thr Thr Ser
65                  70                  75                  80

Lys Leu Gln Lys Phe Glu Asp Leu Ser Gln Ile Gln Thr Tyr Gly Phe
                85                  90                  95
```

-continued

Arg Gly Glu Ala Leu Ala Ser Ile Ser His Val Ala Arg Val Thr Val
            100                 105                 110
Thr Thr Lys Val Lys Glu Asp Arg Cys Ala Trp Arg Val Ser Tyr Ala
        115                 120                 125
Glu Gly Lys Met Leu Glu Ser Pro Lys Pro Val Ala Gly Lys Asp Gly
        130                 135                 140
Thr Thr Ile Leu Val Glu Asp Leu Phe Asn Ile Pro Ser Arg Leu
145                 150                 155                 160
Arg Ala Leu Arg Ser His Asn Asp Glu Tyr Ser Lys Ile Leu Asp Val
                165                 170                 175
Val Gly Arg Tyr Ala Ile His Ser Lys Asp Ile Gly Phe Ser Cys Lys
            180                 185                 190
Lys Phe Gly Asp Ser Asn Tyr Ser Leu Ser Val Lys Pro Ser Tyr Thr
        195                 200                 205
Val Gln Asp Arg Ile Arg Thr Val Phe Asn Lys Ser Val Ala Ser Asn
        210                 215                 220
Leu Ile Thr Phe His Ile Ser Lys Val Glu Asp Leu Asn Leu Glu Ser
225                 230                 235                 240
Val Asp Gly Lys Val Cys Asn Leu Asn Phe Ile Ser Lys Lys Ser Ile
                245                 250                 255
Ser Leu Ile Phe Phe Ile Asn Asn Arg Leu Val Thr Cys Asp Leu Leu
            260                 265                 270
Arg Arg Ala Leu Asn Ser Val Tyr Ser Asn Tyr Leu Pro Lys Gly Phe
        275                 280                 285
Arg Pro Phe Ile Tyr Leu Gly Ile Val Ile Asp Pro Ala Ala Val Asp
        290                 295                 300
Val Asn Val His Pro Thr Lys Arg Glu Val Arg Phe Leu Ser Gln Asp
305                 310                 315                 320
Glu Ile Ile Glu Lys Ile Ala Asn Gln Leu His Ala Glu Leu Ser Ala
                325                 330                 335
Ile Asp Thr Ser Arg Thr Phe Lys Ala Ser Ser Ile Ser Thr Asn Lys
            340                 345                 350
Pro Glu Ser Leu Ile Pro Phe Asn Asp Thr Ile Glu Ser Asp Arg Asn
        355                 360                 365
Arg Lys Ser Leu Arg Gln Ala Gln Val Val Glu Asn Ser Tyr Thr Thr
        370                 375                 380
Ala Asn Ser Gln Leu Arg Lys Ala Lys Arg Gln Glu Asn Lys Leu Val
385                 390                 395                 400
Arg Ile Asp Ala Ser Gln Ala Lys Ile Thr Ser Phe Leu Ser Ser Ser
                405                 410                 415
Gln Gln Phe Asn Phe Glu Gly Ser Ser Thr Lys Arg Gln Leu Ser Glu
            420                 425                 430
Pro Lys Val Thr Asn Val Ser His Ser Gln Glu Ala Glu Lys Leu Thr
        435                 440                 445
Leu Asn Glu Ser Glu Gln Pro Arg Asp Ala Asn Thr Ile Asn Asp Asn
450                 455                 460
Asp Leu Lys Asp Gln Pro Lys Lys Gln Lys Leu Gly Asp Tyr Lys
465                 470                 475                 480
Val Pro Ser Ile Ala Asp Asp Glu Lys Asn Ala Leu Pro Ile Ser Lys
                485                 490                 495
Asp Gly Tyr Ile Arg Val Pro Lys Glu Arg Val Asn Val Asn Leu Thr
            500                 505                 510

Ser Ile Lys Lys Leu Arg Glu Lys Val Asp Asp Ser Ile His Arg Glu
        515                 520                 525

Leu Thr Asp Ile Phe Ala Asn Leu Asn Tyr Val Gly Val Val Asp Glu
        530                 535                 540

Glu Arg Arg Leu Ala Ala Ile Gln His Asp Leu Lys Leu Phe Leu Ile
545                 550                 555                 560

Asp Tyr Gly Ser Val Cys Tyr Glu Leu Phe Tyr Gln Ile Gly Leu Thr
                565                 570                 575

Asp Phe Ala Asn Phe Gly Lys Ile Asn Leu Gln Ser Thr Asn Val Ser
                580                 585                 590

Asp Asp Ile Val Leu Tyr Asn Leu Ser Glu Phe Asp Glu Leu Asn
        595                 600                 605

Asp Asp Ala Ser Lys Glu Lys Ile Ile Ser Lys Ile Trp Asp Met Ser
        610                 615                 620

Ser Met Leu Asn Glu Tyr Tyr Ser Ile Glu Leu Val Asn Asp Gly Leu
625                 630                 635                 640

Asp Asn Asp Leu Lys Ser Val Lys Leu Lys Ser Leu Pro Leu Leu Leu
                645                 650                 655

Lys Gly Tyr Ile Pro Ser Leu Val Lys Leu Pro Phe Phe Ile Tyr Arg
                660                 665                 670

Leu Gly Lys Glu Val Asp Trp Glu Asp Glu Gln Glu Cys Leu Asp Gly
        675                 680                 685

Ile Leu Arg Glu Ile Ala Leu Leu Tyr Ile Pro Asp Met Val Pro Lys
        690                 695                 700

Val Asp Thr Leu Asp Ala Ser Leu Ser Glu Asp Gly Lys Ala Gln Phe
705                 710                 715                 720

Ile Asn Arg Lys Glu His Ile Ser Ser Leu Leu Glu His Val Leu Phe
                725                 730                 735

Pro Cys Ile Lys Arg Arg Phe Leu Ala Pro Arg His Ile Leu Lys Asp
                740                 745                 750

Val Val Glu Ile Ala Asn Leu Pro Asp Leu Tyr Lys Val Phe Glu Arg
        755                 760                 765

Cys

<210> SEQ ID NO 16
<211> LENGTH: 859
<212> TYPE: PRT
<213> ORGANISM: Mus musculus

<400> SEQUENCE: 16

Met Glu Gln Thr Glu Gly Val Ser Thr Glu Cys Ala Lys Ala Ile Lys
1               5                   10                  15

Pro Ile Asp Gly Lys Ser Val His Gln Ile Cys Ser Gly Gln Val Ile
                20                  25                  30

Leu Ser Leu Ser Thr Ala Val Lys Glu Leu Ile Glu Asn Ser Val Asp
        35                  40                  45

Ala Gly Ala Thr Thr Ile Asp Leu Arg Leu Lys Asp Tyr Gly Val Asp
    50                  55                  60

Leu Ile Glu Val Ser Asp Asn Gly Cys Gly Val Glu Glu Asn Phe
65                  70                  75                  80

Glu Gly Leu Ala Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
                100                 105                 110

```
Ser Leu Cys Ala Leu Ser Asp Val Thr Ile Ser Thr Cys His Gly Ser
            115                 120                 125

Ala Ser Val Gly Thr Arg Leu Val Phe Asp His Asn Gly Lys Ile Thr
130                 135                 140

Gln Lys Thr Pro Tyr Pro Arg Pro Lys Gly Thr Thr Val Ser Val Gln
145                 150                 155                 160

His Leu Phe Tyr Thr Leu Pro Val Arg Tyr Lys Glu Phe Gln Arg Asn
                165                 170                 175

Ile Lys Lys Glu Tyr Ser Lys Met Val Gln Val Leu Gln Ala Tyr Cys
                180                 185                 190

Ile Ile Ser Ala Gly Val Arg Val Ser Cys Thr Asn Gln Leu Gly Gln
            195                 200                 205

Gly Lys Arg His Ala Val Val Cys Thr Ser Gly Thr Ser Gly Met Lys
210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ala Val Cys Glu Glu Tyr Gly
                245                 250                 255

Leu Ser Thr Ser Gly Arg His Lys Thr Phe Ser Thr Phe Arg Ala Ser
                260                 265                 270

Phe His Ser Ala Arg Thr Ala Pro Gly Gly Val Gln Gln Thr Gly Ser
            275                 280                 285

Phe Ser Ser Ile Arg Gly Pro Val Thr Gln Gln Arg Ser Leu Ser
            290                 295                 300

Leu Ser Met Arg Phe Tyr His Met Tyr Asn Arg His Gln Tyr Pro Phe
305                 310                 315                 320

Val Val Leu Asn Val Ser Val Asp Ser Glu Cys Val Asp Ile Asn Val
                325                 330                 335

Thr Pro Asp Lys Arg Gln Ile Leu Leu Gln Glu Lys Leu Leu Leu
                340                 345                 350

Ala Val Leu Lys Thr Ser Leu Ile Gly Met Phe Asp Ser Asp Ala Asn
            355                 360                 365

Lys Leu Asn Val Asn Gln Gln Pro Leu Leu Asp Val Glu Gly Asn Leu
370                 375                 380

Val Lys Leu His Thr Ala Glu Leu Glu Lys Pro Val Pro Gly Lys Gln
385                 390                 395                 400

Asp Asn Ser Pro Ser Leu Lys Ser Thr Ala Asp Glu Lys Arg Val Ala
                405                 410                 415

Ser Ile Ser Arg Leu Arg Glu Ala Phe Ser Leu His Pro Thr Lys Glu
                420                 425                 430

Ile Lys Ser Arg Gly Pro Glu Thr Ala Glu Leu Thr Arg Ser Phe Pro
            435                 440                 445

Ser Glu Lys Arg Gly Val Leu Ser Ser Tyr Pro Ser Asp Val Ile Ser
450                 455                 460

Tyr Arg Gly Leu Arg Gly Ser Gln Asp Lys Leu Val Ser Pro Thr Asp
465                 470                 475                 480

Ser Pro Gly Asp Cys Met Asp Arg Glu Lys Ile Glu Lys Asp Ser Gly
                485                 490                 495

Leu Ser Ser Thr Ser Ala Gly Ser Glu Glu Phe Ser Thr Pro Glu
                500                 505                 510

Val Ala Ser Ser Phe Ser Ser Asp Tyr Asn Val Ser Ser Leu Glu Asp
                515                 520                 525

Arg Pro Ser Gln Glu Thr Ile Asn Cys Gly Asp Leu Asp Cys Arg Pro
```

```
                530                 535                 540
Pro Gly Thr Gly Gln Ser Leu Lys Pro Glu Asp His Gly Tyr Gln Cys
545                 550                 555                 560

Lys Ala Leu Pro Leu Ala Arg Leu Ser Pro Thr Asn Ala Lys Arg Phe
                565                 570                 575

Lys Thr Glu Glu Arg Pro Ser Asn Val Asn Ile Ser Gln Arg Leu Pro
            580                 585                 590

Gly Pro Gln Ser Thr Ser Ala Ala Glu Val Asp Val Ala Ile Lys Met
            595                 600                 605

Asn Lys Arg Ile Val Leu Leu Glu Phe Ser Leu Ser Ser Leu Ala Lys
610                 615                 620

Arg Met Lys Gln Leu Gln His Leu Lys Ala Gln Asn Lys His Glu Leu
625                 630                 635                 640

Ser Tyr Arg Lys Phe Arg Ala Lys Ile Cys Pro Gly Glu Asn Gln Ala
                645                 650                 655

Ala Glu Asp Glu Leu Arg Lys Glu Ile Ser Lys Ser Met Phe Ala Glu
            660                 665                 670

Met Glu Ile Leu Gly Gln Phe Asn Leu Gly Phe Ile Val Thr Lys Leu
            675                 680                 685

Lys Glu Asp Leu Phe Leu Val Asp Gln His Ala Ala Asp Glu Lys Tyr
690                 695                 700

Asn Phe Glu Met Leu Gln Gln His Thr Val Leu Gln Ala Gln Arg Leu
705                 710                 715                 720

Ile Thr Pro Gln Thr Leu Asn Leu Thr Ala Val Asn Glu Ala Val Leu
                725                 730                 735

Ile Glu Asn Leu Glu Ile Phe Arg Lys Asn Gly Phe Asp Phe Val Ile
            740                 745                 750

Asp Glu Asp Ala Pro Val Thr Glu Arg Ala Lys Leu Ile Ser Leu Pro
            755                 760                 765

Thr Ser Lys Asn Trp Thr Phe Gly Pro Gln Asp Ile Asp Glu Leu Ile
770                 775                 780

Phe Met Leu Ser Asp Ser Pro Gly Val Met Cys Arg Pro Ser Arg Val
785                 790                 795                 800

Arg Gln Met Phe Ala Ser Arg Ala Cys Arg Lys Ser Val Met Ile Gly
                805                 810                 815

Thr Ala Leu Asn Ala Ser Glu Met Lys Lys Leu Ile Thr His Met Gly
            820                 825                 830

Glu Met Asp His Pro Trp Asn Cys Pro His Gly Arg Pro Thr Met Arg
            835                 840                 845

His Val Ala Asn Leu Asp Val Ile Ser Gln Asn
   850                 855

<210> SEQ ID NO 17
<211> LENGTH: 932
<212> TYPE: PRT
<213> ORGANISM: Homo sapiens

<400> SEQUENCE: 17

Met Lys Gln Leu Pro Ala Ala Thr Val Arg Leu Leu Ser Ser Ser Gln
 1               5                  10                  15

Ile Ile Thr Ser Val Val Ser Val Val Lys Glu Leu Ile Glu Asn Ser
                20                  25                  30

Leu Asp Ala Gly Ala Thr Ser Val Asp Val Lys Leu Glu Asn Tyr Gly
            35                  40                  45
```

-continued

```
Phe Asp Lys Ile Glu Val Arg Asp Asn Gly Glu Gly Ile Lys Ala Val
 50                  55                  60

Asp Ala Pro Val Met Ala Met Lys Tyr Tyr Thr Ser Lys Ile Asn Ser
 65                  70                  75                  80

His Glu Asp Leu Glu Asn Leu Thr Thr Tyr Gly Phe Arg Gly Glu Ala
                 85                  90                  95

Leu Gly Ser Ile Cys Cys Ile Ala Glu Val Leu Ile Thr Thr Arg Thr
                100                 105                 110

Ala Ala Asp Asn Phe Ser Thr Gln Tyr Val Leu Asp Gly Ser Gly His
                115                 120                 125

Ile Leu Ser Gln Lys Pro Ser His Leu Gly Gln Gly Thr Thr Val Thr
130                 135                 140

Ala Leu Arg Leu Phe Lys Asn Leu Pro Val Arg Lys Gln Phe Tyr Ser
145                 150                 155                 160

Thr Ala Lys Lys Cys Lys Asp Glu Ile Lys Lys Ile Gln Asp Leu Leu
                165                 170                 175

Met Ser Phe Gly Ile Leu Lys Pro Asp Leu Arg Ile Val Phe Val His
                180                 185                 190

Asn Lys Ala Val Ile Trp Gln Lys Ser Arg Val Ser Asp His Lys Met
                195                 200                 205

Ala Leu Met Ser Val Leu Gly Thr Ala Val Met Asn Asn Met Glu Ser
210                 215                 220

Phe Gln Tyr His Ser Glu Ser Gln Ile Tyr Leu Ser Gly Phe Leu
225                 230                 235                 240

Pro Lys Cys Asp Ala Asp His Ser Phe Thr Ser Leu Ser Thr Pro Glu
                245                 250                 255

Arg Ser Phe Ile Phe Ile Asn Ser Arg Pro Val His Gln Lys Asp Ile
                260                 265                 270

Leu Lys Leu Ile Arg His His Tyr Asn Leu Lys Cys Leu Lys Glu Ser
                275                 280                 285

Thr Arg Leu Tyr Pro Val Phe Phe Leu Lys Ile Asp Val Pro Thr Ala
290                 295                 300

Asp Val Asp Val Asn Leu Thr Pro Asp Lys Ser Gln Val Leu Leu Gln
305                 310                 315                 320

Asn Lys Glu Ser Val Leu Ile Ala Leu Glu Asn Leu Met Thr Thr Cys
                325                 330                 335

Tyr Gly Pro Leu Pro Ser Thr Asn Ser Tyr Glu Asn Asn Lys Thr Asp
                340                 345                 350

Val Ser Ala Ala Asp Ile Val Leu Ser Lys Thr Ala Glu Thr Asp Val
                355                 360                 365

Leu Phe Asn Lys Val Glu Ser Ser Gly Lys Asn Tyr Ser Asn Val Asp
                370                 375                 380

Thr Ser Val Ile Pro Phe Gln Asn Asp Met His Asn Asp Glu Ser Gly
385                 390                 395                 400

Lys Asn Thr Asp Asp Cys Leu Asn His Gln Ile Ser Ile Gly Asp Phe
                405                 410                 415

Gly Tyr Gly His Cys Ser Ser Glu Ile Ser Asn Ile Asp Lys Asn Thr
                420                 425                 430

Lys Asn Ala Phe Gln Asp Ile Ser Met Ser Asn Val Ser Trp Glu Asn
                435                 440                 445

Ser Gln Thr Glu Tyr Ser Lys Thr Cys Phe Ile Ser Ser Val Lys His
450                 455                 460

Thr Gln Ser Glu Asn Gly Asn Lys Asp His Ile Asp Glu Ser Gly Glu
```

```
                465                 470                 475                 480
Asn Glu Glu Glu Ala Gly Leu Glu Asn Ser Ser Glu Ile Ser Ala Asp
                    485                 490                 495
Glu Trp Ser Arg Gly Asn Ile Leu Lys Asn Ser Val Gly Glu Asn Ile
                500                 505                 510
Glu Pro Val Lys Ile Leu Val Pro Glu Lys Ser Leu Pro Cys Lys Val
                515                 520                 525
Ser Asn Asn Asn Tyr Pro Ile Pro Glu Gln Met Asn Leu Asn Glu Asp
            530                 535                 540
Ser Cys Asn Lys Lys Ser Asn Val Ile Asp Asn Lys Ser Gly Lys Val
545                 550                 555                 560
Thr Ala Tyr Asp Leu Leu Ser Asn Arg Val Ile Lys Lys Pro Met Ser
                            565                 570                 575
Ala Ser Ala Leu Phe Val Gln Asp His Arg Pro Gln Phe Leu Ile Glu
                    580                 585                 590
Asn Pro Lys Thr Ser Leu Glu Asp Ala Thr Leu Gln Ile Glu Glu Leu
                595                 600                 605
Trp Lys Thr Leu Ser Glu Glu Lys Leu Lys Tyr Glu Glu Lys Ala
            610                 615                 620
Thr Lys Asp Leu Glu Arg Tyr Asn Ser Gln Met Lys Arg Ala Ile Glu
625                 630                 635                 640
Gln Glu Ser Gln Met Ser Leu Lys Asp Gly Arg Lys Ile Lys Pro
                        645                 650                 655
Thr Ser Ala Trp Asn Leu Ala Gln Lys His Lys Leu Lys Thr Ser Leu
                660                 665                 670
Ser Asn Gln Pro Lys Leu Asp Glu Leu Leu Gln Ser Gln Ile Glu Lys
                    675                 680                 685
Arg Arg Ser Gln Asn Ile Lys Met Val Gln Ile Pro Phe Ser Met Lys
            690                 695                 700
Asn Leu Lys Ile Asn Phe Lys Lys Gln Asn Lys Val Asp Leu Glu Glu
705                 710                 715                 720
Lys Asp Glu Pro Cys Leu Ile His Asn Leu Arg Phe Pro Asp Ala Trp
                    725                 730                 735
Leu Met Thr Ser Lys Thr Glu Val Met Leu Leu Asn Pro Tyr Arg Val
                740                 745                 750
Glu Glu Ala Leu Leu Phe Lys Arg Leu Leu Glu Asn His Lys Leu Pro
            755                 760                 765
Ala Glu Pro Leu Glu Lys Pro Ile Met Leu Thr Glu Ser Leu Phe Asn
            770                 775                 780
Gly Ser His Tyr Leu Asp Val Leu Tyr Lys Met Thr Ala Asp Asp Gln
785                 790                 795                 800
Arg Tyr Ser Gly Ser Thr Tyr Leu Ser Asp Pro Arg Leu Thr Ala Asn
                    805                 810                 815
Gly Phe Lys Ile Lys Leu Ile Pro Gly Val Ser Ile Thr Glu Asn Tyr
                820                 825                 830
Leu Glu Ile Glu Gly Met Ala Asn Cys Leu Pro Phe Tyr Gly Val Ala
                    835                 840                 845
Asp Leu Lys Glu Ile Leu Asn Ala Ile Leu Asn Arg Asn Ala Lys Glu
                850                 855                 860
Val Tyr Glu Cys Arg Pro Arg Lys Val Ile Ser Tyr Leu Glu Gly Glu
865                 870                 875                 880
Ala Val Arg Leu Ser Arg Gln Leu Pro Met Tyr Leu Ser Lys Glu Asp
                    885                 890                 895
```

-continued

```
Ile Gln Asp Ile Ile Tyr Arg Met Lys His Gln Phe Gly Asn Glu Ile
                900                 905                 910
Lys Glu Cys Val His Gly Arg Pro Phe Phe His His Leu Thr Tyr Leu
        915                 920                 925
Pro Glu Thr Thr
    930

<210> SEQ ID NO 18
<211> LENGTH: 932
<212> TYPE: PRT
<213> ORGANISM: Homo sapiens

<400> SEQUENCE: 18

Met Lys Gln Leu Pro Ala Ala Thr Val Arg Leu Leu Ser Ser Ser Gln
 1               5                  10                  15
Ile Ile Thr Ser Val Ser Val Val Lys Glu Leu Ile Glu Asn Ser
             20                  25                  30
Leu Asp Ala Gly Ala Thr Ser Val Asp Val Lys Leu Glu Asn Tyr Gly
         35                  40                  45
Phe Asp Lys Ile Glu Val Arg Asp Asn Gly Glu Gly Ile Lys Ala Val
     50                  55                  60
Asp Ala Pro Val Met Ala Met Lys Tyr Tyr Thr Ser Lys Ile Asn Ser
 65                  70                  75                  80
His Glu Asp Leu Glu Asn Leu Thr Thr Tyr Gly Phe Arg Gly Glu Ala
                 85                  90                  95
Leu Gly Ser Ile Cys Cys Ile Ala Glu Val Leu Ile Thr Thr Arg Thr
            100                 105                 110
Ala Ala Asp Asn Phe Ser Thr Gln Tyr Val Leu Asp Gly Ser Gly His
        115                 120                 125
Ile Leu Ser Gln Lys Pro Ser His Leu Gly Gln Gly Thr Thr Val Thr
    130                 135                 140
Ala Leu Arg Leu Phe Lys Asn Leu Pro Val Arg Lys Gln Phe Tyr Ser
145                 150                 155                 160
Thr Ala Lys Lys Cys Lys Asp Glu Ile Lys Lys Ile Gln Asp Leu Leu
                165                 170                 175
Met Ser Phe Gly Ile Leu Lys Pro Asp Leu Arg Ile Val Phe Val His
            180                 185                 190
Asn Lys Ala Val Ile Trp Gln Lys Ser Arg Val Ser Asp His Lys Met
        195                 200                 205
Ala Leu Met Ser Val Leu Gly Thr Ala Val Met Asn Asn Met Glu Ser
    210                 215                 220
Phe Gln Tyr His Ser Glu Glu Ser Gln Ile Tyr Leu Ser Gly Phe Leu
225                 230                 235                 240
Pro Lys Cys Asp Ala Asp His Ser Phe Thr Ser Leu Ser Thr Pro Glu
                245                 250                 255
Arg Ser Phe Ile Phe Ile Asn Ser Arg Pro Val His Gln Lys Asp Ile
            260                 265                 270
Leu Lys Leu Ile Arg His His Tyr Asn Leu Lys Cys Leu Lys Glu Ser
        275                 280                 285
Thr Arg Leu Tyr Pro Val Phe Phe Leu Lys Ile Asp Val Pro Thr Ala
    290                 295                 300
Asp Val Asp Val Asn Leu Thr Pro Asp Lys Ser Gln Val Leu Leu Gln
305                 310                 315                 320
Asn Lys Glu Ser Val Leu Ile Ala Leu Glu Asn Leu Met Thr Thr Cys
```

-continued

```
              325                 330                 335
Tyr Gly Pro Leu Pro Ser Thr Asn Ser Tyr Glu Asn Asn Lys Thr Asp
                340                 345                 350

Val Ser Ala Ala Asp Ile Val Leu Ser Lys Thr Ala Glu Thr Asp Val
                355                 360                 365

Leu Phe Asn Lys Val Glu Ser Ser Gly Lys Asn Tyr Ser Asn Val Asp
            370                 375                 380

Thr Ser Val Ile Pro Phe Gln Asn Asp Met His Asn Asp Glu Ser Gly
385                 390                 395                 400

Lys Asn Thr Asp Asp Cys Leu Asn His Gln Ile Ser Ile Gly Asp Phe
                405                 410                 415

Gly Tyr Gly His Cys Ser Ser Glu Ile Ser Asn Ile Asp Lys Asn Thr
                420                 425                 430

Lys Asn Ala Phe Gln Asp Ile Ser Met Ser Asn Val Ser Trp Glu Asn
            435                 440                 445

Ser Gln Thr Glu Tyr Ser Lys Thr Cys Phe Ile Ser Ser Val Lys His
            450                 455                 460

Thr Gln Ser Glu Asn Gly Asn Lys Asp His Ile Asp Glu Ser Gly Glu
465                 470                 475                 480

Asn Glu Glu Glu Ala Gly Leu Glu Asn Ser Ser Glu Ile Ser Ala Asp
                485                 490                 495

Glu Trp Ser Arg Gly Asn Ile Leu Lys Asn Ser Val Gly Glu Asn Ile
                500                 505                 510

Glu Pro Val Lys Ile Leu Val Pro Glu Lys Ser Leu Pro Cys Lys Val
            515                 520                 525

Ser Asn Asn Asn Tyr Pro Ile Pro Glu Gln Met Asn Leu Asn Glu Asp
530                 535                 540

Ser Cys Asn Lys Lys Ser Asn Val Ile Asp Asn Lys Ser Gly Lys Val
545                 550                 555                 560

Thr Ala Tyr Asp Leu Leu Ser Asn Arg Val Ile Lys Lys Pro Met Ser
                565                 570                 575

Ala Ser Ala Leu Phe Val Gln Asp His Arg Pro Gln Phe Leu Ile Glu
            580                 585                 590

Asn Pro Lys Thr Ser Leu Glu Asp Ala Thr Leu Gln Ile Glu Glu Leu
            595                 600                 605

Trp Lys Thr Leu Ser Glu Glu Lys Leu Lys Tyr Glu Glu Lys Ala
            610                 615                 620

Thr Lys Asp Leu Glu Arg Tyr Asn Ser Gln Met Lys Arg Ala Ile Glu
625                 630                 635                 640

Gln Glu Ser Gln Met Ser Leu Lys Asp Gly Arg Lys Lys Ile Lys Pro
                645                 650                 655

Thr Ser Ala Trp Asn Leu Ala Gln Lys His Lys Leu Lys Thr Ser Leu
                660                 665                 670

Ser Asn Gln Pro Lys Leu Asp Glu Leu Leu Gln Ser Gln Ile Glu Lys
            675                 680                 685

Arg Arg Ser Gln Asn Ile Lys Met Val Gln Ile Pro Phe Ser Met Lys
            690                 695                 700

Asn Leu Lys Ile Asn Phe Lys Lys Gln Asn Lys Val Asp Leu Glu Glu
705                 710                 715                 720

Lys Asp Glu Pro Cys Leu Ile His Asn Leu Arg Phe Pro Asp Ala Trp
                725                 730                 735

Leu Met Thr Ser Lys Thr Glu Val Met Leu Leu Asn Pro Tyr Arg Val
                740                 745                 750
```

-continued

```
Glu Glu Ala Leu Leu Phe Lys Arg Leu Leu Glu Asn His Lys Leu Pro
            755                 760                 765

Ala Glu Pro Leu Glu Lys Pro Ile Met Leu Thr Glu Ser Leu Phe Asn
    770                 775                 780

Gly Ser His Tyr Leu Asp Val Leu Tyr Lys Met Thr Ala Asp Asp Gln
785                 790                 795                 800

Arg Tyr Ser Gly Ser Thr Tyr Leu Ser Asp Pro Arg Leu Thr Ala Asn
                805                 810                 815

Gly Phe Lys Ile Lys Leu Ile Pro Gly Val Ser Ile Thr Glu Asn Tyr
                820                 825                 830

Leu Glu Ile Glu Gly Met Ala Asn Cys Leu Pro Phe Tyr Gly Val Ala
            835                 840                 845

Asp Leu Lys Glu Ile Leu Asn Ala Ile Leu Asn Arg Asn Ala Lys Glu
        850                 855                 860

Val Tyr Glu Cys Arg Pro Arg Lys Val Ile Ser Tyr Leu Glu Gly Glu
865                 870                 875                 880

Ala Val Arg Leu Ser Arg Gln Leu Pro Met Tyr Leu Ser Lys Glu Asp
                885                 890                 895

Ile Gln Asp Ile Ile Tyr Arg Met Lys His Gln Phe Gly Asn Glu Ile
                900                 905                 910

Lys Glu Cys Val His Gly Arg Pro Phe Phe His Leu Thr Tyr Leu
            915                 920                 925

Pro Glu Thr Thr
    930

<210> SEQ ID NO 19
<211> LENGTH: 934
<212> TYPE: PRT
<213> ORGANISM: Homo sapiens

<400> SEQUENCE: 19

Met Ala Val Gln Pro Lys Glu Thr Leu Gln Leu Glu Ser Ala Ala Glu
1               5                   10                  15

Val Gly Phe Val Arg Phe Phe Gln Gly Met Pro Glu Lys Pro Thr Thr
            20                  25                  30

Thr Val Arg Leu Phe Asp Arg Gly Asp Phe Tyr Thr Ala His Gly Glu
        35                  40                  45

Asp Ala Leu Leu Ala Ala Arg Glu Val Phe Lys Thr Gln Gly Val Ile
    50                  55                  60

Lys Tyr Met Gly Pro Ala Gly Ala Lys Asn Leu Gln Ser Val Val Leu
65                  70                  75                  80

Ser Lys Met Asn Phe Glu Ser Phe Val Lys Asp Leu Leu Leu Val Arg
                85                  90                  95

Gln Tyr Arg Val Glu Val Tyr Lys Asn Arg Ala Gly Asn Lys Ala Ser
            100                 105                 110

Lys Glu Asn Asp Trp Tyr Leu Ala Tyr Lys Ala Ser Pro Gly Asn Leu
        115                 120                 125

Ser Gln Phe Glu Asp Ile Leu Phe Gly Asn Asn Asp Met Ser Ala Ser
    130                 135                 140

Ile Gly Val Val Gly Val Lys Met Ser Ala Val Asp Gly Gln Arg Gln
145                 150                 155                 160

Val Gly Val Gly Tyr Val Asp Ser Ile Gln Arg Lys Leu Gly Leu Cys
                165                 170                 175

Glu Phe Pro Asp Asn Asp Gln Phe Ser Asn Leu Glu Ala Leu Leu Ile
```

```
                180             185             190
Gln Ile Gly Pro Lys Glu Cys Val Leu Pro Gly Gly Glu Thr Ala Gly
            195                 200             205

Asp Met Gly Lys Leu Arg Gln Ile Ile Gln Arg Gly Ile Leu Ile
    210                 215             220

Thr Glu Arg Lys Lys Ala Asp Phe Ser Thr Lys Asp Ile Tyr Gln Asp
225                 230                 235                 240

Leu Asn Arg Leu Leu Lys Gly Lys Lys Gly Glu Gln Met Asn Ser Ala
                245                 250                 255

Val Leu Pro Glu Met Glu Asn Gln Val Ala Val Ser Ser Leu Ser Ala
            260                 265                 270

Val Ile Lys Phe Leu Glu Leu Leu Ser Asp Asp Ser Asn Phe Gly Gln
            275                 280                 285

Phe Glu Leu Thr Thr Phe Asp Phe Ser Gln Tyr Met Lys Leu Asp Ile
            290                 295                 300

Ala Ala Val Arg Ala Leu Asn Leu Phe Gln Gly Ser Val Glu Asp Thr
305                 310                 315                 320

Thr Gly Ser Gln Ser Leu Ala Ala Leu Leu Asn Lys Cys Lys Thr Pro
                325                 330                 335

Gln Gly Gln Arg Leu Val Asn Gln Trp Ile Lys Gln Pro Leu Met Asp
            340                 345                 350

Lys Asn Arg Ile Glu Glu Arg Leu Asn Leu Val Glu Ala Phe Val Glu
                355                 360                 365

Asp Ala Glu Leu Arg Gln Thr Leu Gln Glu Asp Leu Leu Arg Arg Phe
            370                 375                 380

Pro Asp Leu Asn Arg Leu Ala Lys Lys Phe Gln Arg Gln Ala Ala Asn
385                 390                 395                 400

Leu Gln Asp Cys Tyr Arg Leu Tyr Gln Gly Ile Asn Gln Leu Pro Asn
                405                 410                 415

Val Ile Gln Ala Leu Glu Lys His Glu Gly Lys His Gln Lys Leu Leu
            420                 425                 430

Leu Ala Val Phe Val Thr Pro Leu Thr Asp Leu Arg Ser Asp Phe Ser
            435                 440                 445

Lys Phe Gln Glu Met Ile Glu Thr Thr Leu Asp Met Asp Gln Val Glu
            450                 455                 460

Asn His Glu Phe Leu Val Lys Pro Ser Phe Asp Pro Asn Leu Ser Glu
465                 470                 475                 480

Leu Arg Glu Ile Met Asn Asp Leu Glu Lys Lys Met Gln Ser Thr Leu
                485                 490                 495

Ile Ser Ala Ala Arg Asp Leu Gly Leu Asp Pro Gly Lys Gln Ile Lys
            500                 505                 510

Leu Asp Ser Ser Ala Gln Phe Gly Tyr Tyr Phe Arg Val Thr Cys Lys
            515                 520                 525

Glu Glu Lys Val Leu Arg Asn Asn Lys Asn Phe Ser Thr Val Asp Ile
            530                 535                 540

Gln Lys Asn Gly Val Lys Phe Thr Asn Ser Lys Leu Thr Ser Leu Asn
545                 550                 555                 560

Glu Glu Tyr Thr Lys Asn Lys Thr Glu Tyr Glu Glu Ala Gln Asp Ala
                565                 570                 575

Ile Val Lys Glu Ile Val Asn Ile Ser Ser Gly Tyr Val Glu Pro Met
            580                 585                 590

Gln Thr Leu Asn Asp Val Leu Ala Gln Leu Asp Ala Val Val Ser Phe
            595                 600                 605
```

```
Ala His Val Ser Asn Gly Ala Pro Val Pro Tyr Val Arg Pro Ala Ile
    610                 615                 620

Leu Glu Lys Gly Gln Gly Arg Ile Ile Leu Lys Ala Ser Arg His Ala
625                 630                 635                 640

Cys Val Glu Val Gln Asp Glu Ile Ala Phe Ile Pro Asn Asp Val Tyr
                645                 650                 655

Phe Glu Lys Asp Lys Gln Met Phe His Ile Ile Thr Gly Pro Asn Met
            660                 665                 670

Gly Gly Lys Ser Thr Tyr Ile Arg Gln Thr Gly Val Ile Val Leu Met
        675                 680                 685

Ala Gln Ile Gly Cys Phe Val Pro Cys Glu Ser Ala Glu Val Ser Ile
    690                 695                 700

Val Asp Cys Ile Leu Ala Arg Val Gly Ala Gly Asp Ser Gln Leu Lys
705                 710                 715                 720

Gly Val Ser Thr Phe Met Ala Glu Met Leu Glu Thr Ala Ser Ile Leu
                725                 730                 735

Arg Ser Ala Thr Lys Asp Ser Leu Ile Ile Ile Asp Glu Leu Gly Arg
            740                 745                 750

Gly Thr Ser Thr Tyr Asp Gly Phe Gly Leu Ala Trp Ala Ile Ser Glu
        755                 760                 765

Tyr Ile Ala Thr Lys Ile Gly Ala Phe Cys Met Phe Ala Thr His Phe
    770                 775                 780

His Glu Leu Thr Ala Leu Ala Asn Gln Ile Pro Thr Val Asn Asn Leu
785                 790                 795                 800

His Val Thr Ala Leu Thr Thr Glu Glu Thr Leu Thr Met Leu Tyr Gln
                805                 810                 815

Val Lys Lys Gly Val Cys Asp Gln Ser Phe Gly Ile His Val Ala Glu
            820                 825                 830

Leu Ala Asn Phe Pro Lys His Val Ile Glu Cys Ala Lys Gln Lys Ala
        835                 840                 845

Leu Glu Leu Glu Glu Phe Gln Tyr Ile Gly Glu Ser Gln Gly Tyr Asp
    850                 855                 860

Ile Met Glu Pro Ala Ala Lys Lys Cys Tyr Leu Glu Arg Glu Gln Gly
865                 870                 875                 880

Glu Lys Ile Ile Gln Glu Phe Leu Ser Lys Val Lys Gln Met Pro Phe
                885                 890                 895

Thr Glu Met Ser Glu Glu Asn Ile Thr Ile Lys Leu Lys Gln Leu Lys
            900                 905                 910

Ala Glu Val Ile Ala Lys Asn Asn Ser Phe Val Asn Glu Ile Ile Ser
        915                 920                 925

Arg Ile Lys Val Thr Thr
    930

<210> SEQ ID NO 20
<211> LENGTH: 756
<212> TYPE: PRT
<213> ORGANISM: Homo sapiens

<400> SEQUENCE: 20

Met Ser Phe Val Ala Gly Val Ile Arg Arg Leu Asp Glu Thr Val Val
1               5                   10                  15

Asn Arg Ile Ala Ala Gly Glu Val Ile Gln Arg Pro Ala Asn Ala Ile
            20                  25                  30

Lys Glu Met Ile Glu Asn Cys Leu Asp Ala Lys Ser Thr Ser Ile Gln
```

-continued

```
                35                  40                  45
Val Ile Val Lys Glu Gly Leu Lys Leu Ile Gln Ile Gln Asp Asn
 50                  55                  60
Gly Thr Gly Ile Arg Lys Glu Asp Leu Asp Ile Val Cys Glu Arg Phe
 65                  70                  75                  80
Thr Thr Ser Lys Leu Gln Ser Phe Glu Asp Leu Ala Ser Ile Ser Thr
                 85                  90                  95
Tyr Gly Phe Arg Gly Glu Ala Leu Ala Ser Ile Ser His Val Ala His
                100                 105                 110
Val Thr Ile Thr Thr Lys Thr Ala Asp Gly Lys Cys Ala Tyr Arg Ala
                115                 120                 125
Ser Tyr Ser Asp Gly Lys Leu Lys Ala Pro Pro Lys Pro Cys Ala Gly
                130                 135                 140
Asn Gln Gly Thr Gln Ile Thr Val Glu Asp Leu Phe Tyr Asn Ile Ala
145                 150                 155                 160
Thr Arg Arg Lys Ala Leu Lys Asn Pro Ser Glu Glu Tyr Gly Lys Ile
                165                 170                 175
Leu Glu Val Val Gly Arg Tyr Ser Val His Asn Ala Gly Ile Ser Phe
                180                 185                 190
Ser Val Lys Lys Gln Gly Glu Thr Val Ala Asp Val Arg Thr Leu Pro
                195                 200                 205
Asn Ala Ser Thr Val Asp Asn Ile Arg Ser Ile Phe Gly Asn Ala Val
                210                 215                 220
Ser Arg Glu Leu Ile Glu Ile Gly Cys Glu Asp Lys Thr Leu Ala Phe
225                 230                 235                 240
Lys Met Asn Gly Tyr Ile Ser Asn Ala Asn Tyr Ser Val Lys Lys Cys
                245                 250                 255
Ile Phe Leu Leu Phe Ile Asn His Arg Leu Val Glu Ser Thr Ser Leu
                260                 265                 270
Arg Lys Ala Ile Glu Thr Val Tyr Ala Ala Tyr Leu Pro Lys Asn Thr
                275                 280                 285
His Pro Phe Leu Tyr Leu Ser Leu Glu Ile Ser Pro Gln Asn Val Asp
                290                 295                 300
Val Asn Val His Pro Thr Lys His Glu Val His Phe Leu His Glu Glu
305                 310                 315                 320
Ser Ile Leu Glu Arg Val Gln Gln His Ile Glu Ser Lys Leu Leu Gly
                325                 330                 335
Ser Asn Ser Ser Arg Met Tyr Phe Thr Gln Thr Leu Leu Pro Gly Leu
                340                 345                 350
Ala Gly Pro Ser Gly Glu Met Val Lys Ser Thr Thr Ser Leu Thr Ser
                355                 360                 365
Ser Ser Thr Ser Gly Ser Ser Asp Lys Val Tyr Ala His Gln Met Val
370                 375                 380
Arg Thr Asp Ser Arg Glu Gln Lys Leu Asp Ala Phe Leu Gln Pro Leu
385                 390                 395                 400
Ser Lys Pro Leu Ser Ser Gln Pro Gln Ala Ile Val Thr Glu Asp Lys
                405                 410                 415
Thr Asp Ile Ser Ser Gly Arg Ala Arg Gln Gln Asp Glu Glu Met Leu
                420                 425                 430
Glu Leu Pro Ala Pro Ala Glu Val Ala Ala Lys Asn Gln Ser Leu Glu
                435                 440                 445
Gly Asp Thr Thr Lys Gly Thr Ser Glu Met Ser Glu Lys Arg Gly Pro
450                 455                 460
```

```
Thr Ser Ser Asn Pro Arg Lys Arg His Arg Glu Asp Ser Asp Val Glu
465                 470                 475                 480

Met Val Glu Asp Asp Ser Arg Lys Glu Met Thr Ala Ala Cys Thr Pro
                485                 490                 495

Arg Arg Arg Ile Ile Asn Leu Thr Ser Val Leu Ser Leu Gln Glu Glu
            500                 505                 510

Ile Asn Glu Gln Gly His Glu Val Leu Arg Glu Met Leu His Asn His
        515                 520                 525

Ser Phe Val Gly Cys Val Asn Pro Gln Trp Ala Leu Ala Gln His Gln
    530                 535                 540

Thr Lys Leu Tyr Leu Leu Asn Thr Thr Lys Leu Ser Glu Glu Leu Phe
545                 550                 555                 560

Tyr Gln Ile Leu Ile Tyr Asp Phe Ala Asn Phe Gly Val Leu Arg Leu
                565                 570                 575

Ser Glu Pro Ala Pro Leu Phe Asp Leu Ala Met Leu Ala Leu Asp Ser
            580                 585                 590

Pro Glu Ser Gly Trp Thr Glu Glu Asp Gly Pro Lys Glu Gly Leu Ala
        595                 600                 605

Glu Tyr Ile Val Glu Phe Leu Lys Lys Ala Glu Met Leu Ala Asp
    610                 615                 620

Tyr Phe Ser Leu Glu Ile Asp Glu Glu Gly Asn Leu Ile Gly Leu Pro
625                 630                 635                 640

Leu Leu Ile Asp Asn Tyr Val Pro Pro Leu Glu Gly Leu Pro Ile Phe
                645                 650                 655

Ile Leu Arg Leu Ala Thr Glu Val Asn Trp Asp Glu Glu Lys Glu Cys
            660                 665                 670

Phe Glu Ser Leu Ser Lys Glu Cys Ala Met Phe Tyr Ser Ile Arg Lys
        675                 680                 685

Gln Tyr Ile Ser Glu Glu Ser Thr Leu Ser Gly Gln Gln Ser Glu Val
    690                 695                 700

Pro Gly Ser Ile Pro Asn Ser Trp Lys Trp Thr Val Glu His Ile Val
705                 710                 715                 720

Tyr Lys Ala Leu Arg Ser His Ile Leu Pro Pro Lys His Phe Thr Glu
                725                 730                 735

Asp Gly Asn Ile Leu Gln Leu Ala Asn Leu Pro Asp Leu Tyr Lys Val
            740                 745                 750

Phe Glu Arg Cys
        755

<210> SEQ ID NO 21
<211> LENGTH: 133
<212> TYPE: PRT
<213> ORGANISM: Homo sapiens

<400> SEQUENCE: 21

Met Lys Gln Leu Pro Ala Ala Thr Val Arg Leu Leu Ser Ser Ser Gln
1               5                   10                  15

Ile Ile Thr Ser Val Val Ser Val Val Lys Glu Leu Ile Glu Asn Ser
                20                  25                  30

Leu Asp Ala Gly Ala Thr Ser Val Asp Val Lys Leu Glu Asn Tyr Gly
            35                  40                  45

Phe Asp Lys Ile Glu Val Arg Asp Asn Gly Glu Gly Ile Lys Ala Val
        50                  55                  60

Asp Ala Pro Val Met Ala Met Lys Tyr Tyr Thr Ser Lys Ile Asn Ser
```

```
         65                  70                  75                  80
His Glu Asp Leu Glu Asn Leu Thr Thr Tyr Gly Phe Arg Gly Glu Ala
                85                  90                  95

Leu Gly Ser Ile Cys Cys Ile Ala Glu Val Leu Ile Thr Thr Arg Thr
            100                 105                 110

Ala Ala Asp Asn Phe Ser Thr Gln Tyr Val Leu Asp Gly Ser Gly His
        115                 120                 125

Ile Leu Ser Gln Lys
    130

<210> SEQ ID NO 22
<211> LENGTH: 1360
<212> TYPE: PRT
<213> ORGANISM: Homo sapiens

<400> SEQUENCE: 22

Met Ser Arg Gln Ser Thr Leu Tyr Ser Phe Phe Pro Lys Ser Pro Ala
1               5                   10                  15

Leu Ser Asp Ala Asn Lys Ala Ser Ala Arg Ala Ser Arg Glu Gly Gly
            20                  25                  30

Arg Ala Ala Ala Pro Gly Ala Ser Pro Ser Pro Gly Gly Asp Ala
        35                  40                  45

Ala Trp Ser Glu Ala Gly Pro Gly Pro Arg Pro Leu Ala Arg Ser Ala
    50                  55                  60

Ser Pro Pro Lys Ala Lys Asn Leu Asn Gly Gly Leu Arg Arg Ser Val
65                  70                  75                  80

Ala Pro Ala Ala Pro Thr Ser Cys Asp Phe Ser Pro Gly Asp Leu Val
                85                  90                  95

Trp Ala Lys Met Glu Gly Tyr Pro Trp Trp Pro Cys Leu Val Tyr Asn
            100                 105                 110

His Pro Phe Asp Gly Thr Phe Ile Arg Glu Lys Gly Lys Ser Val Arg
        115                 120                 125

Val His Val Gln Phe Phe Asp Asp Ser Pro Thr Arg Gly Trp Val Ser
    130                 135                 140

Lys Arg Leu Leu Lys Pro Tyr Thr Gly Ser Lys Ser Lys Glu Ala Gln
145                 150                 155                 160

Lys Gly Gly His Phe Tyr Ser Ala Lys Pro Glu Ile Leu Arg Ala Met
                165                 170                 175

Gln Arg Ala Asp Glu Ala Leu Asn Lys Asp Lys Ile Lys Arg Leu Glu
            180                 185                 190

Leu Ala Val Cys Asp Glu Pro Ser Glu Pro Glu Glu Glu Glu Glu Met
        195                 200                 205

Glu Val Gly Thr Thr Tyr Val Thr Asp Lys Ser Glu Glu Asp Asn Glu
    210                 215                 220

Ile Glu Ser Glu Glu Glu Val Gln Pro Lys Thr Gln Gly Ser Arg Arg
225                 230                 235                 240

Ser Ser Arg Gln Ile Lys Lys Arg Arg Val Ile Ser Asp Ser Glu Ser
                245                 250                 255

Asp Ile Gly Gly Ser Asp Val Glu Phe Lys Pro Asp Thr Lys Glu Glu
            260                 265                 270

Gly Ser Ser Asp Glu Ile Ser Ser Gly Val Gly Asp Ser Glu Ser Glu
        275                 280                 285

Gly Leu Asn Ser Pro Val Lys Val Ala Arg Lys Arg Lys Arg Met Val
    290                 295                 300
```

```
Thr Gly Asn Gly Ser Leu Lys Arg Lys Ser Arg Lys Glu Thr Pro
305                 310                 315                 320

Ser Ala Thr Lys Gln Ala Thr Ser Ile Ser Ser Glu Thr Lys Asn Thr
            325                 330                 335

Leu Arg Ala Phe Ser Ala Pro Gln Asn Ser Glu Ser Gln Ala His Val
            340                 345                 350

Ser Gly Gly Gly Asp Asp Ser Ser Arg Pro Thr Val Trp Tyr His Glu
            355                 360                 365

Thr Leu Glu Trp Leu Lys Glu Lys Arg Arg Asp Glu His Arg Arg
370                 375                 380

Arg Pro Asp His Pro Asp Phe Asp Ala Ser Thr Leu Tyr Val Pro Glu
385                 390                 395                 400

Asp Phe Leu Asn Ser Cys Thr Pro Gly Met Arg Lys Trp Trp Gln Ile
            405                 410                 415

Lys Ser Gln Asn Phe Asp Leu Val Ile Cys Tyr Lys Val Gly Lys Phe
            420                 425                 430

Tyr Glu Leu Tyr His Met Asp Ala Leu Ile Gly Val Ser Glu Leu Gly
            435                 440                 445

Leu Val Phe Met Lys Gly Asn Trp Ala His Ser Gly Phe Pro Glu Ile
450                 455                 460

Ala Phe Gly Arg Tyr Ser Asp Ser Leu Val Gln Lys Gly Tyr Lys Val
465                 470                 475                 480

Ala Arg Val Glu Gln Thr Glu Thr Pro Glu Met Met Glu Ala Arg Cys
            485                 490                 495

Arg Lys Met Ala His Ile Ser Lys Tyr Asp Arg Val Val Arg Arg Glu
            500                 505                 510

Ile Cys Arg Ile Ile Thr Lys Gly Thr Gln Thr Tyr Ser Val Leu Glu
            515                 520                 525

Gly Asp Pro Ser Glu Asn Tyr Ser Lys Tyr Leu Leu Ser Leu Lys Glu
530                 535                 540

Lys Glu Glu Asp Ser Ser Gly His Thr Arg Ala Tyr Gly Val Cys Phe
545                 550                 555                 560

Val Asp Thr Ser Leu Gly Lys Phe Phe Ile Gly Gln Phe Ser Asp Asp
            565                 570                 575

Arg His Cys Ser Arg Phe Arg Thr Leu Val Ala His Tyr Pro Pro Val
            580                 585                 590

Gln Val Leu Phe Glu Lys Gly Asn Leu Ser Lys Glu Thr Lys Thr Ile
            595                 600                 605

Leu Lys Ser Ser Leu Ser Cys Ser Leu Gln Glu Gly Leu Ile Pro Gly
610                 615                 620

Ser Gln Phe Trp Asp Ala Ser Lys Thr Leu Arg Thr Leu Leu Glu Glu
625                 630                 635                 640

Glu Tyr Phe Arg Glu Lys Leu Ser Asp Gly Ile Gly Val Met Leu Pro
            645                 650                 655

Gln Val Leu Lys Gly Met Thr Ser Glu Ser Asp Ser Ile Gly Leu Thr
            660                 665                 670

Pro Gly Glu Lys Ser Glu Leu Ala Leu Ser Ala Leu Gly Gly Cys Val
            675                 680                 685

Phe Tyr Leu Lys Lys Cys Leu Ile Asp Gln Glu Leu Leu Ser Met Ala
            690                 695                 700

Asn Phe Glu Glu Tyr Ile Pro Leu Asp Ser Asp Thr Val Ser Thr Thr
705                 710                 715                 720

Arg Ser Gly Ala Ile Phe Thr Lys Ala Tyr Gln Arg Met Val Leu Asp
```

-continued

```
              725                 730                 735
Ala Val Thr Leu Asn Asn Leu Glu Ile Phe Leu Asn Gly Thr Asn Gly
              740                 745                 750

Ser Thr Glu Gly Thr Leu Leu Glu Arg Val Asp Thr Cys His Thr Pro
              755                 760                 765

Phe Gly Lys Arg Leu Leu Lys Gln Trp Leu Cys Ala Pro Leu Cys Asn
              770                 775                 780

His Tyr Ala Ile Asn Asp Arg Leu Asp Ala Ile Glu Asp Leu Met Val
785                 790                 795                 800

Val Pro Asp Lys Ile Ser Glu Val Val Glu Leu Leu Lys Lys Leu Pro
                  805                 810                 815

Asp Leu Glu Arg Leu Leu Ser Lys Ile His Asn Val Gly Ser Pro Leu
              820                 825                 830

Lys Ser Gln Asn His Pro Asp Ser Arg Ala Ile Met Tyr Glu Glu Thr
              835                 840                 845

Thr Tyr Ser Lys Lys Lys Ile Ile Asp Phe Leu Ser Ala Leu Glu Gly
              850                 855                 860

Phe Lys Val Met Cys Lys Ile Ile Gly Ile Met Glu Glu Val Ala Asp
865                 870                 875                 880

Gly Phe Lys Ser Lys Ile Leu Lys Gln Val Ile Ser Leu Gln Thr Lys
                  885                 890                 895

Asn Pro Glu Gly Arg Phe Pro Asp Leu Thr Val Glu Leu Asn Arg Trp
              900                 905                 910

Asp Thr Ala Phe Asp His Glu Lys Ala Arg Lys Thr Gly Leu Ile Thr
              915                 920                 925

Pro Lys Ala Gly Phe Asp Ser Asp Tyr Asp Gln Ala Leu Ala Asp Ile
              930                 935                 940

Arg Glu Asn Glu Gln Ser Leu Leu Glu Tyr Leu Glu Lys Gln Arg Asn
945                 950                 955                 960

Arg Ile Gly Cys Arg Thr Ile Val Tyr Trp Gly Ile Gly Arg Asn Arg
                  965                 970                 975

Tyr Gln Leu Glu Ile Pro Glu Asn Phe Thr Thr Arg Asn Leu Pro Glu
              980                 985                 990

Glu Tyr Glu Leu Lys Ser Thr Lys Lys Gly Cys Lys Arg Tyr Trp Thr
              995                1000                1005

Lys Thr Ile Glu Lys Lys Leu Ala Asn Leu Ile Asn Ala Glu Glu Arg
             1010                1015                1020

Arg Asp Val Ser Leu Lys Asp Cys Met Arg Arg Leu Phe Tyr Asn Phe
1025                1030                1035                1040

Asp Lys Asn Tyr Lys Asp Trp Gln Ser Ala Val Glu Cys Ile Ala Val
                 1045                1050                1055

Leu Asp Val Leu Leu Cys Leu Ala Asn Tyr Ser Arg Gly Gly Asp Gly
             1060                1065                1070

Pro Met Cys Arg Pro Val Ile Leu Leu Pro Glu Asp Thr Pro Pro Phe
             1075                1080                1085

Leu Glu Leu Lys Gly Ser Arg His Pro Cys Ile Thr Lys Thr Phe Phe
             1090                1095                1100

Gly Asp Asp Phe Ile Pro Asn Asp Ile Leu Ile Gly Cys Glu Glu Glu
1105                1110                1115                1120

Glu Gln Glu Asn Gly Lys Ala Tyr Cys Val Leu Val Thr Gly Pro Asn
                 1125                1130                1135

Met Gly Gly Lys Ser Thr Leu Met Arg Gln Ala Gly Leu Leu Ala Val
             1140                1145                1150
```

```
Met Ala Gln Met Gly Cys Tyr Val Pro Ala Glu Val Cys Arg Leu Thr
        1155                1160                1165

Pro Ile Asp Arg Val Phe Thr Arg Leu Gly Ala Ser Asp Arg Ile Met
    1170                1175                1180

Ser Gly Glu Ser Thr Phe Phe Val Glu Leu Ser Glu Thr Ala Ser Ile
1185                1190                1195                1200

Leu Met His Ala Thr Ala His Ser Leu Val Leu Val Asp Glu Leu Gly
                1205                1210                1215

Arg Gly Thr Ala Thr Phe Asp Gly Thr Ala Ile Ala Asn Ala Val Val
            1220                1225                1230

Lys Glu Leu Ala Glu Thr Ile Lys Cys Arg Thr Leu Phe Ser Thr His
        1235                1240                1245

Tyr His Ser Leu Val Glu Asp Tyr Ser Gln Asn Val Ala Val Arg Leu
    1250                1255                1260

Gly His Met Ala Cys Met Val Glu Asn Glu Cys Glu Asp Pro Ser Gln
1265                1270                1275                1280

Glu Thr Ile Thr Phe Leu Tyr Lys Phe Ile Lys Gly Ala Cys Pro Lys
                1285                1290                1295

Ser Tyr Gly Phe Asn Ala Ala Arg Leu Ala Asn Leu Pro Glu Glu Val
            1300                1305                1310

Ile Gln Lys Gly His Arg Lys Ala Arg Glu Phe Glu Lys Met Asn Gln
        1315                1320                1325

Ser Leu Arg Leu Phe Arg Glu Val Cys Leu Ala Ser Glu Arg Ser Thr
    1330                1335                1340

Val Asp Ala Glu Ala Val His Lys Leu Leu Thr Leu Ile Lys Glu Leu
1345                1350                1355                1360

<210> SEQ ID NO 23
<211> LENGTH: 389
<212> TYPE: PRT
<213> ORGANISM: Homo sapiens

<400> SEQUENCE: 23

Met Ala Gln Pro Lys Gln Glu Arg Val Ala Arg Ala Arg His Gln Arg
1               5                   10                  15

Ser Glu Thr Ala Arg His Gln Arg Ser Glu Thr Ala Lys Thr Pro Thr
            20                  25                  30

Leu Gly Asn Arg Gln Thr Pro Thr Leu Gly Asn Arg Gln Thr Pro Arg
        35                  40                  45

Leu Gly Ile His Ala Arg Pro Arg Arg Ala Thr Thr Ser Leu Leu
    50                  55                  60

Thr Leu Leu Leu Ala Phe Gly Lys Asn Ala Val Arg Cys Ala Leu Ile
65                  70                  75                  80

Gly Pro Gly Ser Leu Thr Ser Arg Thr Arg Pro Leu Thr Glu Pro Leu
                85                  90                  95

Gly Glu Lys Glu Arg Arg Glu Val Phe Phe Pro Pro Arg Pro Glu Arg
            100                 105                 110

Val Glu His Asn Val Glu Ser Ser Arg Trp Glu Pro Arg Arg Arg Gly
        115                 120                 125

Ala Cys Gly Ser Arg Gly Gly Asn Phe Pro Ser Pro Arg Gly Gly Ser
    130                 135                 140

Gly Val Ala Ser Leu Glu Arg Ala Glu Asn Ser Ser Thr Glu Pro Ala
145                 150                 155                 160

Lys Ala Ile Lys Pro Ile Asp Arg Lys Ser Val His Gln Ile Cys Ser
```

```
                          165                 170                 175
Gly Pro Val Val Pro Ser Leu Arg Pro Asn Ala Val Lys Glu Leu Val
                180                 185                 190
Glu Asn Ser Leu Asp Ala Gly Ala Thr Asn Val Asp Leu Lys Leu Lys
            195                 200                 205
Asp Tyr Gly Val Asp Leu Ile Glu Val Ser Gly Asn Cys Gly Val
        210                 215                 220
Glu Glu Glu Asn Phe Glu Gly Phe Thr Leu Lys His His Thr Cys Lys
225                 230                 235                 240
Ile Gln Glu Phe Ala Asp Leu Thr Gln Val Glu Thr Phe Gly Phe Arg
                245                 250                 255
Gly Glu Ala Leu Ser Ser Leu Cys Ala Leu Ser Asp Val Thr Ile Ser
                260                 265                 270
Thr Cys Arg Val Ser Ala Lys Val Gly Thr Arg Leu Val Phe Asp His
            275                 280                 285
Tyr Gly Lys Ile Ile Gln Lys Thr Pro Tyr Pro Arg Pro Arg Gly Met
        290                 295                 300
Thr Val Ser Val Lys Gln Leu Phe Ser Thr Leu Pro Val His His Lys
305                 310                 315                 320
Glu Phe Gln Arg Asn Ile Lys Lys Arg Ala Cys Phe Pro Phe Ala
                325                 330                 335
Phe Cys Arg Asp Cys Gln Phe Pro Glu Ala Ser Pro Ala Met Leu Pro
            340                 345                 350
Val Gln Pro Val Glu Leu Thr Pro Arg Ser Thr Pro His Pro Cys
        355                 360                 365
Ser Leu Glu Asp Asn Val Ile Thr Val Phe Ser Ser Val Lys Asn Gly
    370                 375                 380
Pro Gly Ser Ser Arg
385

<210> SEQ ID NO 24
<211> LENGTH: 264
<212> TYPE: PRT
<213> ORGANISM: Homo sapiens

<400> SEQUENCE: 24

Met Cys Pro Trp Arg Pro Arg Leu Gly Arg Arg Cys Met Val Ser Pro
1               5                   10                  15
Arg Glu Ala Asp Leu Gly Pro Gln Lys Asp Thr Arg Leu Asp Leu Pro
                20                  25                  30
Arg Ser Pro Ala Arg Ala Pro Arg Glu Gln Asn Ser Leu Gly Glu Val
            35                  40                  45
Asp Arg Arg Gly Pro Arg Glu Gln Thr Arg Ala Pro Ala Thr Ala Ala
        50                  55                  60
Pro Pro Arg Pro Leu Gly Ser Arg Gly Ala Glu Ala Ala Glu Pro Gln
65                  70                  75                  80
Glu Gly Leu Ser Ala Thr Val Ser Ala Cys Phe Gln Glu Gln Gln Glu
                85                  90                  95
Met Asn Thr Leu Gln Gly Pro Val Ser Phe Lys Asp Val Ala Val Asp
                100                 105                 110
Phe Thr Gln Glu Glu Trp Arg Gln Leu Asp Pro Asp Glu Lys Ile Ala
            115                 120                 125
Tyr Gly Asp Val Met Leu Glu Asn Tyr Ser His Leu Val Ser Val Gly
        130                 135                 140
```

```
Tyr Asp Tyr His Gln Ala Lys His His His Gly Val Glu Val Lys Glu
145                 150                 155                 160

Val Glu Gln Gly Glu Glu Pro Trp Ile Met Glu Gly Glu Phe Pro Cys
                165                 170                 175

Gln His Ser Pro Glu Pro Ala Lys Ala Ile Lys Pro Ile Asp Arg Lys
            180                 185                 190

Ser Val His Gln Ile Cys Ser Gly Pro Val Val Leu Ser Leu Ser Thr
        195                 200                 205

Ala Val Lys Glu Leu Val Glu Asn Ser Leu Asp Ala Gly Ala Thr Asn
    210                 215                 220

Ile Asp Leu Lys Leu Lys Asp Tyr Gly Val Asp Leu Ile Glu Val Ser
225                 230                 235                 240

Asp Asn Gly Cys Gly Val Glu Glu Asn Phe Glu Gly Leu Ile Ser
                245                 250                 255

Phe Ser Ser Glu Thr Ser His Met
                260

<210> SEQ ID NO 25
<211> LENGTH: 264
<212> TYPE: PRT
<213> ORGANISM: Homo sapiens

<400> SEQUENCE: 25

Met Cys Pro Trp Arg Pro Arg Leu Gly Arg Arg Cys Met Val Ser Pro
1               5                   10                  15

Arg Glu Ala Asp Leu Gly Pro Gln Lys Asp Thr Arg Leu Asp Leu Pro
            20                  25                  30

Arg Ser Pro Ala Arg Ala Pro Arg Glu Gln Asn Ser Leu Gly Glu Val
        35                  40                  45

Asp Arg Arg Gly Pro Arg Glu Gln Thr Arg Ala Pro Ala Thr Ala Ala
    50                  55                  60

Pro Pro Arg Pro Leu Gly Ser Arg Gly Ala Glu Ala Ala Glu Pro Gln
65                  70                  75                  80

Glu Gly Leu Ser Ala Thr Val Ser Ala Cys Phe Gln Glu Gln Gln Glu
                85                  90                  95

Met Asn Thr Leu Gln Gly Pro Val Ser Phe Lys Asp Val Ala Val Asp
            100                 105                 110

Phe Thr Gln Glu Glu Trp Arg Gln Leu Asp Pro Asp Glu Lys Ile Ala
        115                 120                 125

Tyr Gly Asp Val Met Leu Glu Asn Tyr Ser His Leu Val Ser Val Gly
    130                 135                 140

Tyr Asp Tyr His Gln Ala Lys His His His Gly Val Glu Val Lys Glu
145                 150                 155                 160

Val Glu Gln Gly Glu Glu Pro Trp Ile Met Glu Gly Glu Phe Pro Cys
                165                 170                 175

Gln His Ser Pro Glu Pro Ala Lys Ala Ile Lys Pro Ile Asp Arg Lys
            180                 185                 190

Ser Val His Gln Ile Cys Ser Gly Pro Val Val Leu Ser Leu Ser Thr
        195                 200                 205

Ala Val Lys Glu Leu Val Glu Asn Ser Leu Asp Ala Gly Ala Thr Asn
    210                 215                 220

Ile Asp Leu Lys Leu Lys Asp Tyr Gly Val Asp Leu Ile Glu Val Ser
225                 230                 235                 240

Asp Asn Gly Cys Gly Val Glu Glu Asn Phe Glu Gly Leu Ile Ser
                245                 250                 255
```

```
Phe Ser Ser Glu Thr Ser His Met
            260

<210> SEQ ID NO 26
<211> LENGTH:
<212> TYPE:
<213> ORGANISM:

<400> SEQUENCE: 26

000
```

METHODS FOR GENERATING HYPERMUTABLE MICROBES

This application claims the benefit of provisional application Ser. No. 60/181,929 filed Feb. 11, 2000.

FIELD OF THE INVENTION

The invention is related to the area of mismatch repair genes. In particular it is related to the field of in situ mutagenesis of single celled organisms.

BACKGROUND OF THE INVENTION

Within the past four years, the genetic cause of the Hereditary Nonpolyposis Colorectal Cancer Syndrome (HNPCC), also known as Lynch syndrome II, has been ascertained for the majority of kindred's affected with the disease (14). The molecular basis of HNPCC involves genetic instability resulting from defective mismatch repair (MMR). Several genes have been identified in humans that encode for proteins and appear to participate in the MMR process, including the mutS homologs GTBP, hMSH2, and hMSH3 and the mutL homologs hMLH1, hMLH3, hPMS1, and hPMS2 (4,9,11,17,19,22,24,38). Germline mutations in four of these genes (hMSH2, hMLH1, hPMS1, and hPMS2) have been identified in HNPCC kindred's (13). Though the mutator defect that arises from the MMR deficiency can affect any DNA sequence, microsatellite sequences are particularly sensitive to MMR abnormalities (14, 25, 27, 29). Microsatellite instability (MI) is therefore a useful indicator of defective MMR. In addition to its occurrence in virtually all tumors arising in HNPCC patients, MI is found in a small fraction of sporadic tumors with distinctive molecular and phenotypic properties (13).

HNPCC is inherited in an autosomal dominant fashion, so that the normal cells of affected family members contain one mutant allele of the relevant MMR gene (inherited from an affected parent) and one wild-type allele (inherited from the unaffected parent). During the early stages of tumor development, however, the wild-type allele is inactivated through a somatic mutation, leaving the cell with no functional MMR gene and resulting in a profound defect in MMR activity. Because a somatic mutation in addition to a germline mutation is required to generate defective MMR in the tumor cells, this mechanism is generally referred to as one involving two hits, analogous to the biallelic inactivation of tumor suppressor genes that initiate other hereditary cancers. In line with this two-hit mechanism, the non-neoplastic cells of HNPCC patients generally retain near normal levels of MMR activity due to the presence of the wild-type allele (11, 13, 24). In addition, similar findings are observed in other diploid organisms (2, 5, 8).

The ability to alter signal transduction pathways by manipulation of a gene product's function, either by overexpression of the wild type protein or a fragment thereof, or by introduction of mutations into specific protein domains of the protein, the so-called dominant-negative inhibitory mutant, were described over a decade ago in the yeast system *Saccharomyces cerevisiae* by Herskowitz (Nature 329:219–222, 1987). It has been demonstrated that overexpression of wild type gene products can result in a similar, dominant-negative inhibitory phenotype due most likely to the "saturating-out" of a factor, such as a protein, that is present at low levels and necessary for activity; removal of the protein by binding to a high level of its cognate partner results in the same net effect, leading to inactivation of the protein and the associated signal transduction pathway.

Recently, work done by Nicolaides et.al. (32) has demonstrated the utility of introducing dominant negative inhibitory mismatch repair mutants into mammalian cells to confer global DNA hypermutability. There is a need in the art for additional techniques for generating mutations in bacteria which can be used to make strains for production, biocatalysis, bioremediation, and drug discovery.

SUMMARY OF THE INVENTION

It is an object of the present invention to provide a method for rendering bacterial cells hypermutable.

It is another object of the present invention to provide genetically altered bacteria.

It is yet another object of the present invention to provide a method to produce bacteria that are hypermutable.

It is an object of the invention to provide a method to inactivate the process that results in hypermutable cells following strain selection.

It is a further object of the invention to provide a method of mutating a gene of interest in a bacterium.

These and other embodiments of the invention are provided by one or more of the embodiments described below. In one embodiment, a method is provided for making a hypermutable bacteria. A polynucleotide comprising a dominant negative allele of a mismatch repair gene is introduced into a bacterium, whereby the cell becomes hypermutable. Preferably the allele is under the control of an inducible transcription regulatory sequence.

According to another aspect of the invention a homogeneous composition of cultured, hypermutable, bacteria is provided. The bacteria comprise a dominant negative allele of a mismatch repair gene. Preferably the allele is under the control of an inducible transcription regulatory sequence.

Another embodiment of the invention provides a method for generating a mutation in a gene of interest. A bacterial culture comprising the gene of interest and a dominant negative allele of a mismatch repair gene is grown. The cell is hypermutable. It is tested to determine whether the gene of interest harbors a mutation. Preferably the allele is under the control of an inducible transcription regulatory sequence.

According to still another aspect of the invention a method for generating a mutation in a gene of interest is provided. A bacterium comprising the gene of interest and a dominant negative allele of a mismatch repair gene is grown to form a population of mutated bacteria. The population of mutated bacteria is cultivated under trait selection conditions. At least one of the cultivated bacteria is tested to determine that the gene of interest harbors a mutation. Preferably the allele is under the control of an inducible transcription regulatory sequence.

Still another aspect of the invention is a method for enhancing the mutation rate of a bacterium. A bacterium comprising a dominant negative allele of an MMR gene is exposed to a mutagen whereby the mutation rate of the bacterium is enhanced in excess of the rate in the absence of mutagen and in excess of the rate in the absence of the dominant negative allele. Preferably the allele is under the control of an inducible transcription regulatory sequence.

Yet another aspect of the invention is a method for generating an MMR-proficient bacterium with a new output trait. A mismatch repair deficient bacterium comprising a gene of interest and a dominant negative allele of a mismatch repair gene is grown to form a population of mutated bacteria. The population of mutated bacteria is cultivated under trait selection conditions. At least one of the cultivated bacteria is tested to determine that the gene of interest harbors a mutation. Mismatch repair activity is restored to the at least one of the cultivated bacteria. Preferably the allele is under the control of an inducible transcription regulatory sequence.

These and other embodiments of the invention provide the art with methods that can generate enhanced mutability in bacteria as well as providing prokaryotic organisms harboring potentially useful mutations to generate novel output traits for commercial applications. The ability to create hypermutable organisms using dominant negative alleles has great commercial value for the generation of innovative bacterial strains that display new output features useful for a variety of applications, including but not limited to the manufacturing industry for the generation of new biochemicals useful for detoxifying noxious chemicals from by-products of manufacturing processes or those used as catalysts, as well as helping in remediation of toxins present in the environment, including but not limited to polychlorobenzenes (PCBs), heavy metals and other environmental hazards for which there is a need to remove them from the environment. In addition to obtaining organisms that are useful for removal of toxins from the environment, novel microbes can be selected for enhanced activity to either produce increased quantity or quality of a protein or non-protein therapeutic molecule by means of biotransformation (3). Biotransformation is the enzymatic conversion, by a microbe or an extract derived from the microbe, of one chemical intermediate to the next product. There are many examples of biotransformation in use for the commercial manufacturing of important biological and chemical products, including Penicillin G, Erythromycin, and Clavulanic Acid as well as organisms that are efficient at conversion of "raw" materials to advanced intermediates and/or final products (Berry, A. Trends Biotechnol. 14(7):250–256). The ability to control DNA hypermutability in host bacterial strains using a dominant negative MMR (as described above) allows for the generation of variant subtypes that can be selected for new phenotypes of commercial interest, including but not limited to organisms that are toxin-resistant, have the capacity to degrade a toxin in situ or the ability to convert a molecule from an intermediate to either an advanced intermediate or a final product. Other applications using dominant negative MMR genes to produce genetic alteration of bacterial hosts for new output traits include but are not limited to recombinant production strains that produce higher quantities of a recombinant polypeptide as well as the use of altered endogenous genes that can transform chemical or catalyze manufacturing downstream processes.

This application teaches of the use of a regulatable dominant negative MMR phenotype to produce a prokaryotic strain with a commercially beneficial output trait. Using this process, microbes expressing a dominant negative MMR can be directly selected for the phenotype of interest. Once a selected bacterium with a specified output trait is isolated, the hypermutable activity of the dominant negative MMR allele can be turned-off by several methods well known to those skilled in the art. For example, if the dominant-negative allele is expressed by an inducible promoter system, including but not limited to promoters such as: TAC-LACI, tryp (Brosius et.al. Gene 27:161–172, 1984), araBAD (Guzman et.al., *J. Bact.* 177:4121–4130, 1995) pLex (La Vallie et.al., Bio.Technology 11:187–193, 1992) pRSET (Schoepfer, R. *Gene* 124:83–85, 1993) , pT7 (Studier *J. Mol. Biol.* 219(1):37–44, 1991) etc., the inducer is removed and the promoter activity is reduced, or a system that excises the MMR gene insert from the host cells harboring the expression vector such as the Cre-lox (Hasan, N. et. al. *Gene* 2:51–56, 1994), as well as methods that can homologously knockout of the expression vector. In addition to the recombinant methods outlined above that have the capacity to eliminate the MMR activity from the microbe, it has been demonstrated that many chemicals have the ability to "cure" microbial cells of plasmids. For example, chemical treatment of cells with drugs including bleomycin (Attfield et al. *Antimicrob. Agents Chemother.* 27:985–988, 1985) or novobiocin, coumermycin, and quinolones (Fu et al. *Chemotherapy* 34:415–418, 1988) have been shown to result in microbial cells that lack endogenous plasmid as evidenced by Southern analysis of cured cells as well as sensitivity to the appropriate antibiotic (1, 41–43). Whether by use of recombinant means or treatment of cells with chemicals, removal of the MMR-expression plasmid results in the re-establishment of a genetically stable microbial cell-line. Therefore, the restoration of MMR allows host bacteria to function normally to repair DNA. The newly generated mutant bacterial strain that exhibits a novel, selected output trait is now suitable for a wide range of commercial processes or for gene/protein discovery to identify new biomolecules that are involved in generating a particular output trait.

While it has been documented that MMR deficiency can lead to as much as a 1000-fold increase in the endogenous DNA mutation rate of a host, there is no assurance that MMR deficiency alone will be sufficient to alter every gene within the DNA of the host bacterium to create altered biochemicals with new activity(s). Therefore, the use of chemical agents and their respective analogues such as ethidium bromide, EMS, MNNG, MNU, Tamoxifen, 8-Hydroxyguanine, as well as others listed but not limited to in publications by: Khromov-Borisov, N. N., et. al. (Mutat. Res. 430:55–74, 1999); Ohe, T., et. al. (Mutat. Res. 429: 189–199, 1999); Hour, T. C. et. al. (Food Chem. Toxicol. 37:569–579, 1999); Hrelia, P., et. al. (Chem. Biol. Interact. 118:99–111, 1999); Garganta, F., et. al. (Environ. Mol. Mutagen. 33:75–85, 1999); Ukawa-Ishikawa S., et. al. (Mutat. Res. 412:99–107, 1998); the website having the URL address: www host server, ehs.utah.edu domain name, ohh directory, mutagens subdirectory, etc. can be used to further enhance the spectrum of mutations and increase the likelihood of obtaining alterations in one or more genes that can in turn generate host bacteria with a desired new output trait(s) (10,39,40). Prior art teaches that mismatch repair deficiency leads to hosts with an increased resistance to toxicity by chemicals with DNA damaging activity. This feature allows for the creation of additional genetically diverse hosts when mismatch defective bacteria are exposed to such agents, which would be otherwise impossible due to the toxic effects of such chemical mutagens [Colella, G., et. al. (Br. J. Cancer 80:338–343, 1999); Moreland, N. J., et. al. (Cancer Res. 59:2102–2106, 1999); Humbert, O., et. al. (Carcinogenesis 20:205–214, 1999); Glaab, W. E., et. al. (Mutat. Res. 398:197–207, 1998)]. Moreover, prior art teaches that mismatch repair is responsible for repairing chemical-induced DNA adducts, so therefore blocking this process could theoretically increase the number, types, mutation rate and genomic alterations of a bacterial host [Rasmussen, L. J. et. al. (Carcinogenesis 17:2085–2088, 1996); Sledziewska-Gojska, E., et. al. (Mutat. Res. 383: 31–37, 1997); and Janion, C. et. al. (Mutat. Res. 210:15–22, 1989)]. In addition to the chemicals listed above, other types of DNA mutagens include ionizing radiation and UV-irradiation, which are known to cause DNA mutagenesis in bacteria can also be used to potentially enhance this process. These agents which are extremely toxic to host cells and therefore result in a decrease in the actual pool size of altered bacterial cells are more tolerated in MMR defective hosts and in turn allow for a enriched spectrum and degree of genomic mutation (7).

This application teaches new uses of MMR deficient bacterial cells to create commercially viable microbes that express novel output traits. Moreover, this application teaches the use of dominant negative MMR genes to decrease the endogenous MMR activity of the host followed by placing the cells under selection to obtain a desired, sought after output trait for commercial applications such as but not limited to recombinant manufacturing, biotransformation and bioremediation. Furthermore, the application teaches the use of restoring MMR activity to the hypermutable bacterial host following strain selection of the variant of interest as a means to genetically "fix" the new mutations in the host genome. The application also teaches the use of enhanced hypermutability in bacteria by using MMR deficiency and chemical or radiation mutagenesis to create variant subtypes of bacteria useful for commercial and other applications. The application describes uses of hypermutable bacteria for producing strains that can be used to generate new output traits for chemical manufacturing, pharmaceutical and other commercially applicable processes.

DETAILED DESCRIPTION OF THE INVENTION

Figure 1:
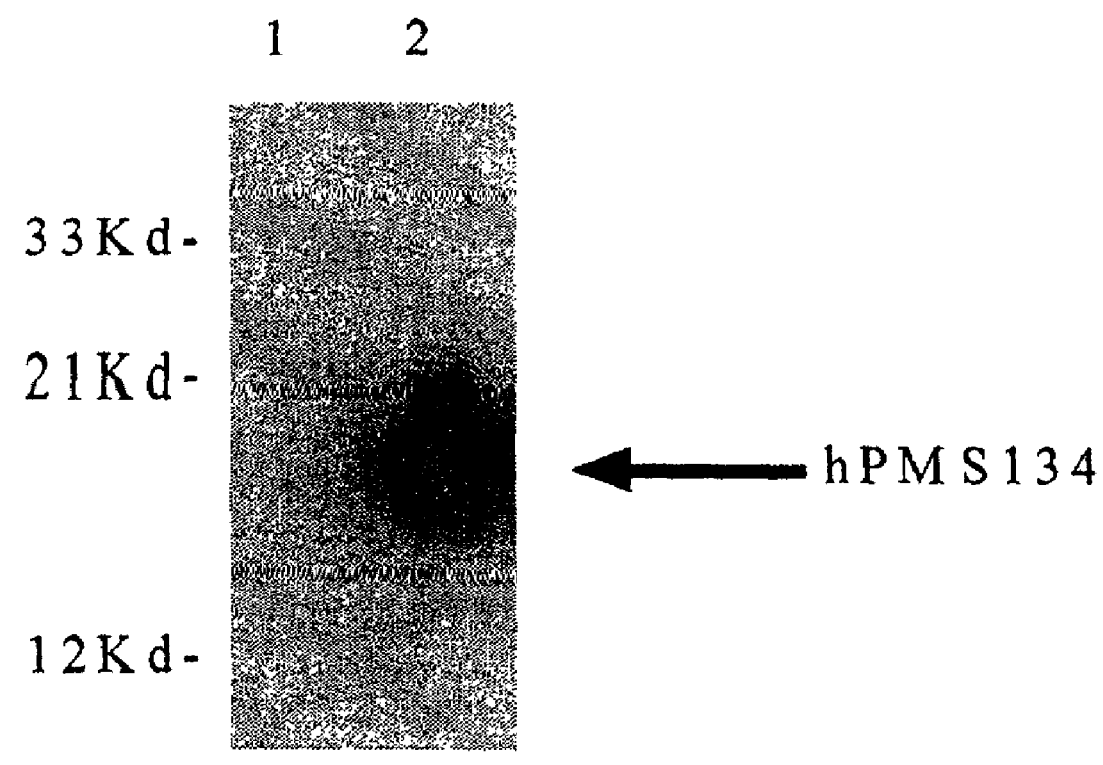
FIG. 1. Western blot of steady-state PMS134 levels in IPTG-treated samples in DH10B strain. Cells containing the pTACPMS134 (lane 2) showed a robust steady state level of protein after induction in contrast to cells expressing empty vector (lane 1). Blots were probed with an anti-human-PMS2 polyclonal antibody.

The inventors present a method for developing hypermutable bacteria by altering the activity of endogenous mismatch repair activity of hosts. Wild type and some dominant negative alleles of mismatch repair genes, when introduced and expressed in bacteria, increase the rate of spontaneous mutations by reducing the effectiveness of the endogenous MMR-mediated DNA repair activity, thereby rendering the bacteria highly susceptible to genetic alterations due to hypermutability. Hypermutable bacteria can then be utilized to screen for novel mutations in a gene or a set of genes that produce variant siblings that exhibit a new output trait(s) not found in the wild type cells.

The process of mismatch repair, also called mismatch proofreading, is an evolutionarily highly conserved process that is carried out by protein complexes described in cells as disparate as prokaryotic cells such as bacteria to more complex mammalian cells (14, 29, 31, 33, 34). A mismatch repair gene is a gene that encodes one of the proteins of such a mismatch repair complex. Although not wanting to be bound by any particular theory of mechanism of action, a mismatch repair complex is believed to detect distortions of the DNA helix resulting from non-complementary pairing of nucleotide bases. The non-complementary base on the newer DNA strand is excised, and the excised base is replaced with the appropriate base that is complementary to the older DNA strand. In this way, cells eliminate many mutations that occur as a result of mistakes in DNA replication, resulting in genetic stability of the sibling cells derived from the parental cell.

Some wild type alleles as well as dominant negative alleles cause a mismatch repair defective phenotype even in the presence of a wild-type allele in the same cell. An example of a dominant negative allele of a mismatch repair gene is the human gene hPMS2-134, which carries a truncation mutation at codon 134 (32). The mutation causes the product of this gene to abnormally terminate at the position of the 134th amino acid, resulting in a shortened polypeptide containing the N-terminal 133 amino acids. Such a mutation causes an increase in the rate of mutations, which accumulate in cells after DNA replication. Expression of a dominant negative allele of a mismatch repair gene results in impairment of mismatch repair activity, even in the presence of the wild-type allele. Any mismatch repair allele, which produces such effect, can be used in this invention. In addition, the use of over-expressed wildtype MMR gene alleles from human, mouse, plants, and yeast in bacteria has been shown to cause a dominant negative effect on the bacterial hosts MMR activity (9, 33, 34, 38).

Dominant negative alleles of a mismatch repair gene can be obtained from the cells of humans, animals, yeast, bacteria, plants or other organisms. Screening cells for defective mismatch repair activity can identify such alleles. Mismatch repair genes may be mutant or wild type. Bacterial host MMR may be mutated or not. The term bacteria used in this application include any organism from the prokaryotic kingdom. These organisms include genera such as but not limited to *Agrobacterium, Anaerobacter, Aquabacterium, Azorhizobium, Bacillus, Bradyrhizobium, Cryobacterium, Escherichia, Enterococcus, Heliobacterium, Klebsiella, Lactobacillus, Methanococcus, Methanothermobacter, Micrococcus, Mycobacterium, Oceanomonas, Pseudomonas, Rhizobium, Staphylococcus, Streptococcus, Streptomyces, Thermusaquaticus, Thermaerobacter, Thermobacillus,* etc. Other procaryotes that can be used for this application are listed at the website having the URL address www.host server, bacterio.cict.fr domain name, validgenericnames directory. Bacteria exposed to chemical mutagens or radiation exposure can be screened for defective mismatch repair. Genomic DNA, cDNA, or mRNA from any cell encoding a mismatch repair protein can be analyzed for variations from the wild type sequence. Dominant negative alleles of a mismatch repair gene can also be created artificially, for example, by producing variants of the hPMS2-134 allele or other mismatch repair genes (32). Various techniques of site-directed mutagenesis can be used. The suitability of such alleles, whether natural or artificial, for use in generating hypermutable bacteria can be evaluated by testing the mismatch repair activity (using methods described in ref 32) caused by the allele in the presence of one or more wild-type alleles, to determine if it is a dominant negative allele.

A bacterium that over-expresses a wild type mismatch repair allele as or a dominant negative allele of a mismatch repair gene will become hypermutable. This means that the spontaneous mutation rate of such bacteria is elevated compared to bacteria without such alleles. The degree of elevation of the spontaneous mutation rate can be at least 2-fold, 5-fold, 10-fold, 20-fold, 50-fold, 100-fold, 200-fold, 500-fold, or 1000-fold that of the normal bacteria as measured as a function of bacterial doubling/minute.

According to one aspect of the invention, a polynucleotide encoding either a wild type or a dominant negative form of a mismatch repair protein is introduced into bacteria. The gene can be any dominant negative allele encoding a protein which is part of a mismatch repair complex, for example, mutS, mutL, mutH, or mutY homologs of the bacterial, yeast, plant or mammalian genes (14, 28). The dominant negative allele can be naturally occurring or made in the laboratory. The polynucleotide can be in the form of genomic DNA, cDNA, RNA, or a chemically synthesized polynucleotide or polypeptide. The molecule can be introduced into the cell by transfection, transformation, conjugation, fusion, or other methods well described in the literature.

Any process can be used whereby a polynucleotide or polypeptide is introduced into a cell. The process of gene transfer can be carried out in a bacterial culture using a suspension culture. The bacteria can be any type classified under the prokaryotes.

In general, gene transfer will be carried out using a suspension of cells but other methods can also be employed as long as a sufficient fraction of the treated cells incorporate the polynucleotide or polypeptide so as to allow recipient cells to be grown and utilized. The protein product of the polynucleotide may be transiently or stably expressed in the cell. Techniques for gene transfer are well known to those skilled in the art. Available techniques to introduce a polynucleotide or polypeptide into a prokaryote include but are not limited to electroporation, transduction, cell fusion, the use of chemically competent cells (e.g. calcium chloride), and packaging of the polynucleotide together with lipid for fusion with the cells of interest. Once a cell has been transformed with the dominant negative mismatch repair gene or protein, the cell can be propagated and manipulated in either liquid culture or on a solid agar matrix, such as a petri dish. If the transfected cell is stable, the gene will be retained and expressed at a consistent level when the promoter is constitutively active, or when in the presence of appropriate inducer molecules when the promoter is inducible, for many cell generations, and a stable, hypermutable bacterial strain results.

An isolated bacterial cell is a clone obtained from a pool of a bacterial culture by chemically selecting out non-recipient strains using, for example, antibiotic selection of an expression vector. If the bacterial cell is derived from a single cell, it is defined as a clone.

A polynucleotide encoding a dominant negative form of a mismatch repair protein can be introduced into the genome of a bacterium or propagated on an extra-chromosomal plasmid. Selection of clones harboring the mismatch repair gene expression vector can be accomplished by addition of any of several different antibiotics, including but not limited to ampicillin, kanamycin, chloramphenicol, zeocin, and tetracycline. The microbe can be any species for which suitable techniques are available to produce transgenic microorganisms, such as but not limited to genera including *Bacillus, Pseudomonas, Staphylococcus, Escherichia* and others.

Any method for making transgenic bacteria known in the art can be used. According to one process of producing a transgenic microorganism, the polynucleotide is transfected into the microbe by one of the methods well known to those in the art. Next, the microbial culture is grown under conditions that select for cells in which the polynucleotide encoding the mismatch repair gene is either incorporated into the host genome as a stable entity or propagated on a self-replicating extra-chromosomal plasmid, and the protein encoded by the polynucleotide fragment transcribed and subsequently translated into a functional protein within the cell. Once transgenic microbe is engineered to harbor the expression construct, it is then propagated to generate and sustain a culture of transgenic microbes indefinitely.

Once a stable, transgenic microorganism has been engineered to express a functional mismatch repair (MMR) protein, the microbe can be exploited to create novel mutations in one or more target gene(s) of interest harbored within the same microorganism. A gene of interest can be any gene naturally possessed by the bacterium or one introduced into the bacterial host by standard recombinant DNA techniques. The target gene(s) may be known prior to the selection or unknown. One advantage of employing such transgenic microbes to induce mutations in resident or extra-chromosomal genes within the microbe is that it is unnecessary to expose the microorganism to mutagenic insult, whether it be chemical or radiation in nature, to produce a series of random gene alterations in the target gene(s). This is due to the highly efficient nature and the spectrum of naturally occurring mutations that result as a consequence of the altered mismatch repair process. However, it is possible to increase the spectrum and frequency of mutations by the concomitant use of either chemicals and/or radiation together with MMR defective cells. These include DNA mutagens, DNA alkylating agents, DNA intercalating agents, DNA oxidizing agents, ionizing radiation, and ultra-violet radiation. The net effect of the combination treatment is the increase in altered gene pool in the genetically altered microbe that result in an increased alteration of an allele(s) that are useful for producing new output traits. Another benefit of using MMR-defective microbes that are taught in this application is that one can perform a genetic screen for the direct selection of variant sub-clones that exhibit new output traits with commercially important applications. This allows one to bypass tedious and time consuming gene identification, isolation and characterization.

Mutations can be detected by analyzing the recombinant microbe for alterations in the genotype and/or phenotype post-activation of the decreased mismatch repair activity of the transgenic microorganism. Novel genes that produce altered phenotypes in MMR-defective microbial cells can be discerned by any variety of molecular techniques well known to those in the art. For example, the microbial genome can be isolated and a library of restriction fragments cloned into a plasmid vector. The library can be introduced into a "normal" cell and the cells exhibiting the novel phenotype screened. A plasmid is isolated from those normal cells that exhibit the novel phenotype and the gene(s) characterized by DNA sequence analysis. Alternatively, differential messenger RNA screen can be employed utilizing driver and tester RNA (derived from wild type and novel mutant respectively) followed by cloning the differential transcripts and characterizing them by standard molecular biology methods well known to those skilled in the art. Furthermore, if the mutant sought is on encoded by an extrachromosomal plasmid, then following co-expression of the dominant negative MMR gene and the gene of interest to be altered and phenotypic selection, the plasmid is isolated from mutant clones and analyzed by DNA sequence analysis by methods well known to those in the art. Phenotypic screening for output traits in MMR-defective mutants can be by biochemical activity and/or a physical phenotype of the altered gene product. A mutant phenotype can also be detected by identifying alterations in electrophoretic mobility, DNA binding in the case of transcription factors, spectroscopic properties such as IR, CD, X-ray crystallography or high field NMR analysis, or other physical or structural characteristics of a protein encoded by a mutant gene. It is also possible to screen for altered novel function of a protein in situ, in isolated form, or in model systems. One can screen for alteration of any property of the microorganism associated with the function of the gene of interest, whether the gene is known prior to the selection or unknown. The aforementioned screening and selection discussion is meant to illustrate the potential means of obtaining novel mutants with commercially valuable output traits.

Plasmid expression vectors that harbor the mismatch repair (MMR) gene inserts can be used in combination with a number of commercially available regulatory sequences to control both the temporal and quantitative biochemical expression level of the dominant negative MMR protein. The regulatory sequences can be comprised of a promoter, enhancer or promoter/enhancer combination and can be inserted either upstream or downstream of the MMR gene to control the expression level. The regulatory promoter sequence can be any of those well known to those in the art, including but not limited to the lac, tetracycline, tryptophan-inducible, phosphate inducible, T7-polymerase-inducible (30), and steroid inducible constructs as well as sequences which can result in the excision of the dominant negative mismatch repair gene such as those of the Cre-Lox system. These types of regulatory systems are familiar to those skilled in the art.

Once a microorganism with a novel, desired output trait of interest is created, the activity of the aberrant MMR activity can be attenuated or eliminated by any of a variety of methods, including removal of the inducer from the culture medium that is responsible for promoter activation, gene disruption of the aberrant MMR gene constructs, electroporation and/or chemical curing of the expression plasmids (Brosius, Biotechnology 10:205–225,1988; Wang et. al., J. of Fujian Agricultural University 28:43–46,1999; Fu et. al., Chem Abstracts 34:415–418, 1988). The resulting microbe is now useful as a stable strain that can be applied to various commercial applications, depending upon the selection process placed upon it.

In cases where genetically deficient mismatch repair bacteria [strains such as but not limited to: M1 (mutS) and in EC2416 (mutS delta umuDC), and mutL or mutY strains] are used to derive new output traits, transgenic constructs can be used that express wild-type mismatch repair genes sufficient to complement the genetic defect and therefore restore mismatch repair activity of the host after trait selection [Grzesiuk, E. et. al. (Mutagenesis 13:127–132, 1998); Bridges, B. A., et. al. (EMBO J. 16:3349–3356, 1997); LeClerc, J. E., Science 15:1208–1211, 1996); Jaworski, A. et. al. (Proc. Natl. Acad. Sci USA 92:11019–11023, 1995)]. The resulting microbe is genetically stable and can be applied to various commercial practices. The use of over expressing foreign mismatch repair genes from human and yeast such as PMS1, MSH2, MLH1, MLH3, etc. have been previously demonstrated to produce a dominant negative mutator phenotype in bacterial hosts (35, 36, 37). In addition, the use of bacterial strains expressing prokaryotic dominant negative MMR genes as well as hosts that have genomic defects in endogenous MMR proteins have also been previously shown to result in a dominant negative mutator phenotype (29,32). However, the findings disclosed here teach the use of MMR genes, including the human PMSR2 and PMSR3 gene (ref 19), the related PMS134 truncated MMR gene (ref 32), the plant mismatch repair genes and those genes that are homologous to the 134 N-terminal amino acids of the PMS2 gene which include the MutL family of MMR proteins and including the PMSR and PMS2L homologs described by Hori et. al. (accession number $NM_{13}$ 005394 and $NM_{13}$ 005395) and Nicolaides (reference 19) to create hypermutable microbes. In addition, this application teaches the use of DNA mutagens in combination with MMR defective microbial hosts to enhance the hypermutable production of genetic alterations. This accentuates MMR activity for generation of microorganisms with commercially relevant output traits such as but not limited to recombinant protein production strains, biotransformation, and bioremediation.

The above disclosure generally describes the present invention. A more complete understanding can be obtained by reference to the following specific examples that will be provided herein for purposes of illustration only, and are not intended to limit the scope of the invention

EXAMPLES

Example 1

Generation of Inducible MMR Dominant Negative Allele Vectors

Bacterial expression constructs were prepared to determine if the human PMS2 related gene (hPMSR3) (19) and the human PMS134 gene (32) are capable of inactivating the bacterial MMR activity and thereby increase the overall frequency of genomic hypermutation, a consequence of which is the generation of variant sib cells with novel output traits following host selection. Moreover, the use of regulatable expression vectors will allow for suppression of dominant negative MMR alleles and restoration of the MMR pathway and genetic stability in hosts cells (43). For these studies, a plasmid encoding the hPMS134 cDNA was altered by polymerase chain reaction (PCR). The 5' oligonucleotide has the following structure: 5'-ACG CAT ATG GAG CGA GCT GAG AGC TCG AGT-3' (SEQ ID NO: 1) that includes the NdeI restriction site CAT ATG. The 3'-oligonucleotide has the following structure: 5'-GAA TTC TTA TCA CGT AGA ATC GAG ACC GAG GAG AGG GTT AGG GAT AGG CTT ACC AGT TCC AAC CTT CGC CGA TGC-3'

(SEQ ID NO: 2) that includes an EcoRI site GAA TTC and the 14 amino acid epitope for the V5 antibody. The oligonucleotides were used for PCR under standard conditions that included 25 cycles of PCR (95° C. for 1 minute, 55° C. for 1 minute, 72° C. for 1.5 minutes for 25 cycles followed by 3 minutes at 72° C). The PCR fragment was purified by gel electrophoresis and cloned into pTA2.1 (InVitrogen) by standard cloning methods (Sambrook et al., Molecular Cloning: A Laboratory Manual, Third Edition, 2001), creating the plasmid pTA2.1-hPMS134. pTA2.1-hPMS134 was digested with the restriction enzyme EcoRI to release the insert (there are two EcoRI restriction sites in the multiple cloning site of pTA2.1 that flank the insert) and the fragment filled in with Klenow fragment and dNTPs. Next, the fragment was gel purified, then digested with NdeI and inserted in pT7-Ea that had been digested with NdeI and BamHI (filled with Klenow) and phosphatase treated. The new plasmid was designated pT7-Ea-hPMS134. The following strategy, similar to that described above to clone human PMS134, was used to construct an expression vector for the human related gene PMSR3. First, the hPMSR3 fragment was amplified by PCR to introduce two restriction sites, an NdeI restriction site at the 5'-end and an Eco RI site at the 3'-end of the fragment. The 5'-oligonucleotide that was used for PCR has the following structure: 5'-ACG CAT ATG TGT CCT TGG CGG CCT AGA-3' (SEQ ID NO: 3) that includes the NdeI restriction site CAT ATG. The 3'-oligonucleotide used for PCR has the following structure: 5'-GAA TTC TTA TTA CGT AGA ATC GAG ACC GAG GAG AGG GTT AGG GAT AGG CTT ACC CAT GTG TGA TGT TTC AGA GCT-3' (SEQ ID NO: 4) that includes an EcoRI site GAA TTC and the V5 epitope to allow for antibody detection. The plasmid that contained human PMSR3 in pBluescript SK (19) was used as the PCR target with the hPMS2-specific oligonucleotides above. Following 25 cycles of PCR (95° C. for 1 minute, 55° C for 1 minute, 72° C. for 1.5 minutes for 25 cycles followed by 3 minutes at 72° C.). The PCR fragment was purified by gel electrophoresis and cloned into pTA2.1 (InVitrogen) by standard cloning methods (Sambrook et al., Molecular Cloning: A Laboratory Manual, Third Edition, 2001), creating the plasmid pTA2.1-hR3. pTA2.1-hR3 was next digested with the restriction enzyme EcoRI to release the insert (there are two EcoRI restriction sites in the multiple cloning site of pTA2.1 that flank the insert) and the fragment filled in with Klenow fragment and dNTPs. Then, the fragment was gel purified, then digested with NdeI and inserted in pT7-Ea that had been digested with NdeI and BamHI (filled with Klenow) and phosphatase treated. The new plasmid was designated pT7-Ea-hR3.

BL21 cells harbor an additional expression vector for the lysozyme protein, which has been demonstrated to bind to the T7 polymerase in situ; this results in a bacterial strain that has very low levels of T7 polymerase expression. However, upon addition of the inducer IPTG, the cells express high-levels of T7 polymerase due to the IPTG-inducible element that drives expression of the polymerase that is resident within the genome of the BL21 cells (30). The BL21 cells are chloramphenicol resistant due to the plasmid that expresses lysozyme within the cell. To introduce the pT7-hPMS134 or the pT7-hPMSR3 genes into BL21 cells, the cells were made competent by incubating the cells in ice cold 50mM $CaCl_2$ for 20 minutes, followed by concentrating the cells and adding super-coiled plasmid DNA as describe (Maniatis, T. et. al. Cold Spring Harbor Laboratory Press, Third Edition, 2001). Ampicillin resistant BL21 were selected on LB-agar plates [5% yeast extract, 10% bactotryptone, 5% NaCl, 1.5% bactoagar, pH 7.0 (Difco)] plates containing 25 µg/ml chloramphenicol and 100 µg/ml ampicillin. The next day, bacterial colonies were picked and analyzed for vectors containing an intact pTACPMS134 or pTAC empty vector by restriction endonuclease digestion and sequence analysis.

In addition to constructing a V5-epitope tagged PMS134 construct we also constructed and tested a non-epitope tagged version. This was prepared to demonstrate that the simple fact of epitope tagging the construct did not result in alteration of the dominant-negative phenotype that PMS134 has on mismatch repair activity. For these studies, a BamHI restriction fragment containing the hPMS134 cDNA was filled-in with Klenow fragment and then sub-cloned into a Klenow-filled blunt-ended NdeI-XhoI site of the pTACLAC expression vector, which contains the isopropylthio-β-galactosidase (IPTG)-inducible bacterial TAC promoter and ampicillin resistance gene as selectable marker. The NdeI-XhoI cloning site is flanked by the TACLAC promoter that contains the LacI repressor site followed by a Shine Dalgarno ribosome-binding site at the 5' flanking region and the T1 T2 ribosomal RNA terminator in the 3' flanking region. The TACLAC vector also contains the LacI gene, which is constitutively expressed by the TAC promoter.

DH10B bacterial cells containing the pBCSK vector (Stratagene), which constitutively expresses the β-galactosidase gene and contains the chloramphenicol resistance marker for selection, were made competent via the $CaCl_2$ method (Maniatis, T. et. al. Cold Spring Harbor Laboratory Press, 1982). This vector turns bacterial cells blue when grown in the presence of IPTG and X-gal that aids in the detection of bacterial colonies. Competent cells were transfected with the pTAC empty vector or the pTACPMS134 vector following the heat-shock protocol. Transfected cultures were plated onto LB-agar [5% yeast extract, 10% bactotryptone, 5% NaCl, 1.5% bactoagar, pH 7.0 (Difco)] plates containing 25 µg/ml chloramphenicol and 100 µ/ml ampicillin. The next day, bacterial colonies were picked and analyzed for vectors containing an intact pTACPMS134 or pTAC empty vector by restriction endonuclease digestion and sequence analysis. Ten clones of each bacteria containing correct empty or PMS134 inserts were then grown to confluence overnight in LB media (5% yeast extract, 10% bactotryptone, 5% NaCl, pH 7.0) containing 10 µg/ml chloramphenicol and 50 µg/ml ampicillin. The next day TAC empty or pTACPMS134 cultures were diluted 1:4 in LB medium plus 50 µM IPTG (Gold Biotechnology) and cultures were grown for 12 and 24 hours at 37° C. After incubation, 50 µl aliquots were taken from each culture and added to 150 µls of 2×SDS buffer and cultures were analyzed for PMS134 protein expression by western blot.

Western blots were carried out as follows. 50 µls of each PMS134 or empty vector culture was directly lysed in 2×lysis buffer (60 mM Tris, pH 6.8, 2% SDS, 10% glycerol, 0.1 M 2-mercaptoethanol, 0.001% bromophenol blue) and samples were boiled for 5 minutes. Lysate proteins were separated by electrophoresis on 4–20% Tris glycine gels (Novex). Gels were electroblotted onto Immobilon-P (Millipore) in 48 mM Tris base, 40 mM glycine, 0.0375% SDS, 20% methanol and blocked overnight at 4° C. in Tris-buffered saline plus 0.05% Tween-20 and 5% condensed milk. Filters were probed with a rabbit polyclonal antibody generated against the N-terminus of the human PMS2 polypeptide (Santa Cruz), which is able to recognize the PMS134 polypeptide (31), followed by a secondary goat anti-rabbit horseradish peroxidase-conjugated antibody. After incubation with the secondary antibody, blots are developed using chemiluminescence (Pierce) and exposed to film to measure PMS134 expression.

As shown in FIG. 1, a robust expression of PMS134 could be detected in bacterial cells containing pTACPMS134 (lane 2) in contrast to cells expressing empty vector (lane 1), which had no signal.

Figure 2:
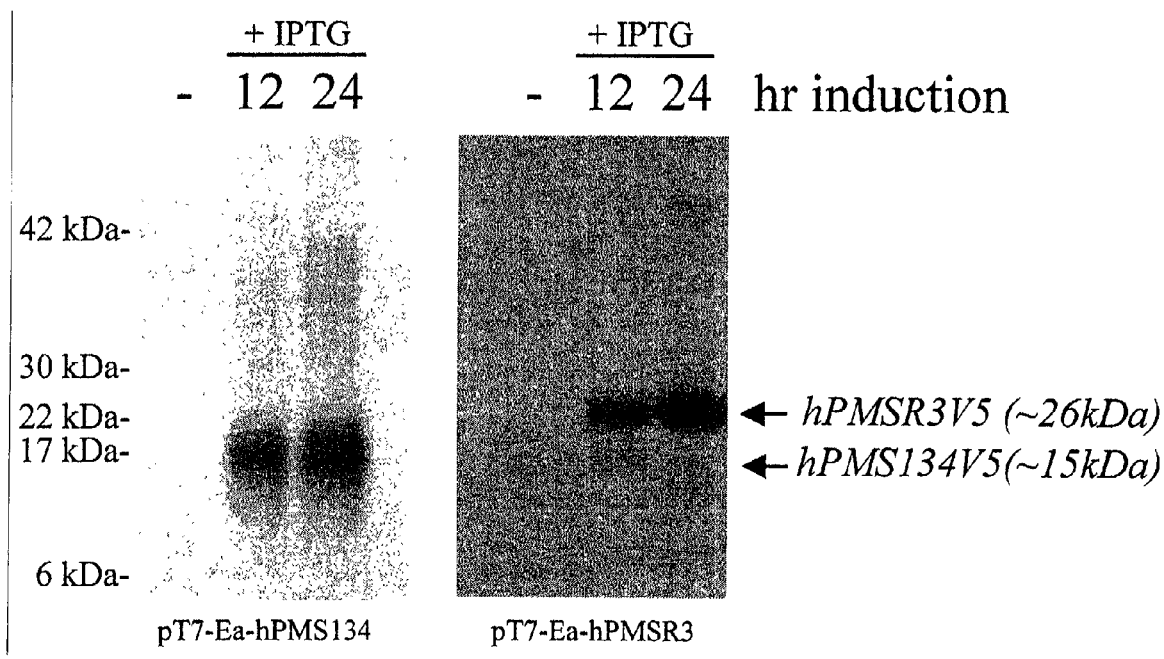
FIG. 2. Western blot of PMS134V5 and PMSR3V5 in IPTG-treated (+) and untreated (−) samples in BL21 strain. Blots were probed with an anti-V5 antibody, which is directed to the C-terminal tag of each protein.

For induction of PMS134 and PMSR3 in BL21 cells, the pT7-Ea-hPMS134 or the pT7-Ea-hPMSR3 cells were induced with 50 μM IPTG for 12 and 24 hours. Cell lysates were prepared and analyzed by western blot listed above using either the N-terminal PMS2 antibody to detect the PMS134 containing cells or the antiV5-horseradish peroxidase conjugated monoclonal antibody (InVitrogen) to detect the PMS134V5 and PMSR3V5 polypeptides. FIG. 2 shows the expression of PMS134V5 and PMSR3V5 before (−) lanes and after IPTG (+) lanes induction.

Example 2

Figure 3:
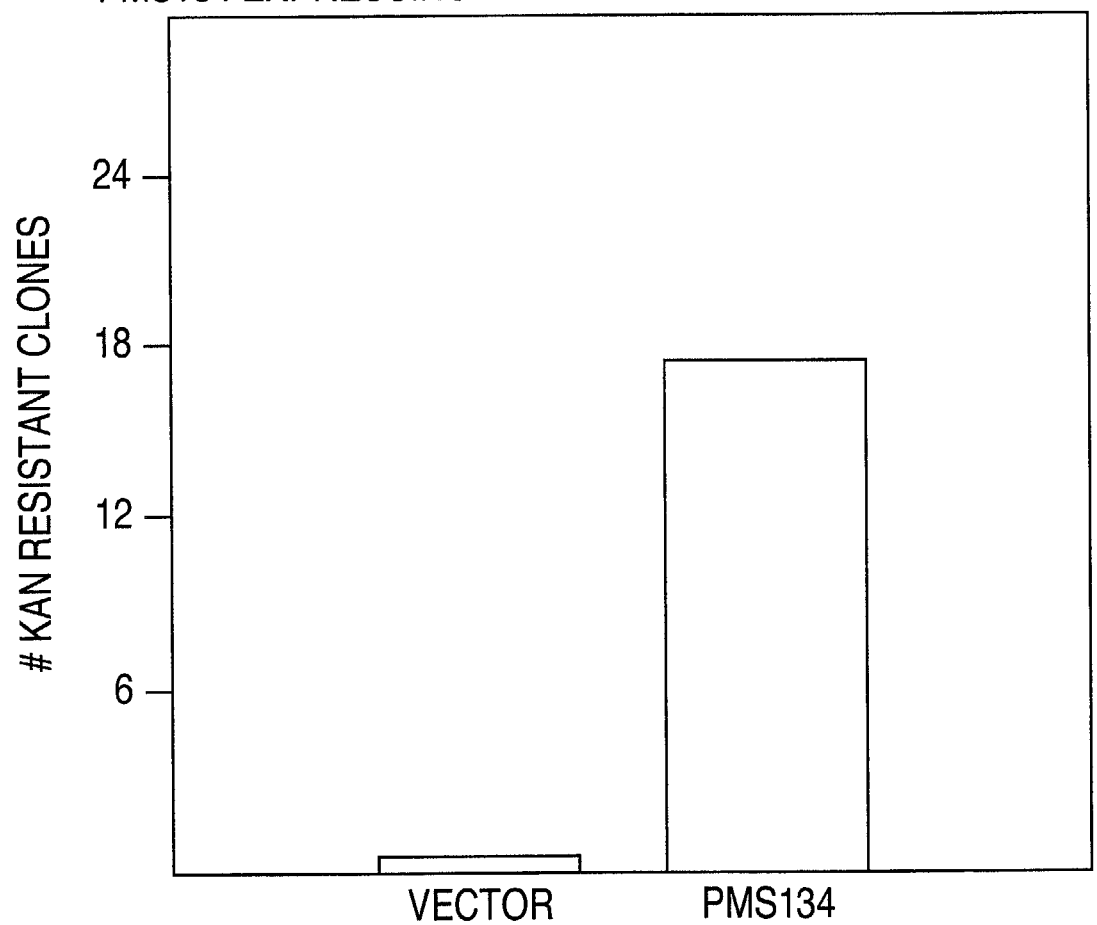
FIG. 3. Number of Kanamycin resistant PMS134 and vector control DH10B clones. IPTG-induced strains were grown and plated onto KAN plates and grown for 18 hours at 37° C. to identify number of KAN resistant clones due to genetic alteration.

Generation of Hypermutable Bacteria with Inducible Dominant Negative Alleles of Mismatch Repair Genes Bacterial clones expressing the PMS134 or the empty vector were grown in liquid culture for 24 hr at 37° C. in the presence of 10 μg/ml chloramphenicol and 50 μg/ml ampicillin plus 50 μM IPTG. The next day, cultures were diluted 1:10 in medium containing 50 μM IPTG plus ampicillin/chloramphenicol (AC) or ampicillin/chloramphenicol plus 25 μg/ml kanamycin (ACK) and cultures were grown for 18 hr at 37° C. The following day, a 0.1 μl aliquot (2 μl diluted in 1000 μl of LB medium and used 50 μl for plating) of cells grown in AC medium were plated on LB-agar plates containing 40 μg/ml of 5-bromo-4-chloro-3-indolyl-B-D-galactoside (X-gal) plus 100 μg/ml ampicillin (AMP), while a 1 μl aliquot (1 μl diluted in 100 μl of LB medium and used 100 μl for plating) of cells grown in ACK medium were plated on LB-agar plates containing X-gal and 50 μg/ml kanamycin (KAN). Plates were incubated for 18 hours at 37° C. The results from these studies show that cells expressing the PMS134 were able to increase hypermutation in the genome of the DH10B bacterial strain which resulted in the production of siblings that exhibit new biological traits such as KAN resistance (FIG. 3).

Figure 4:
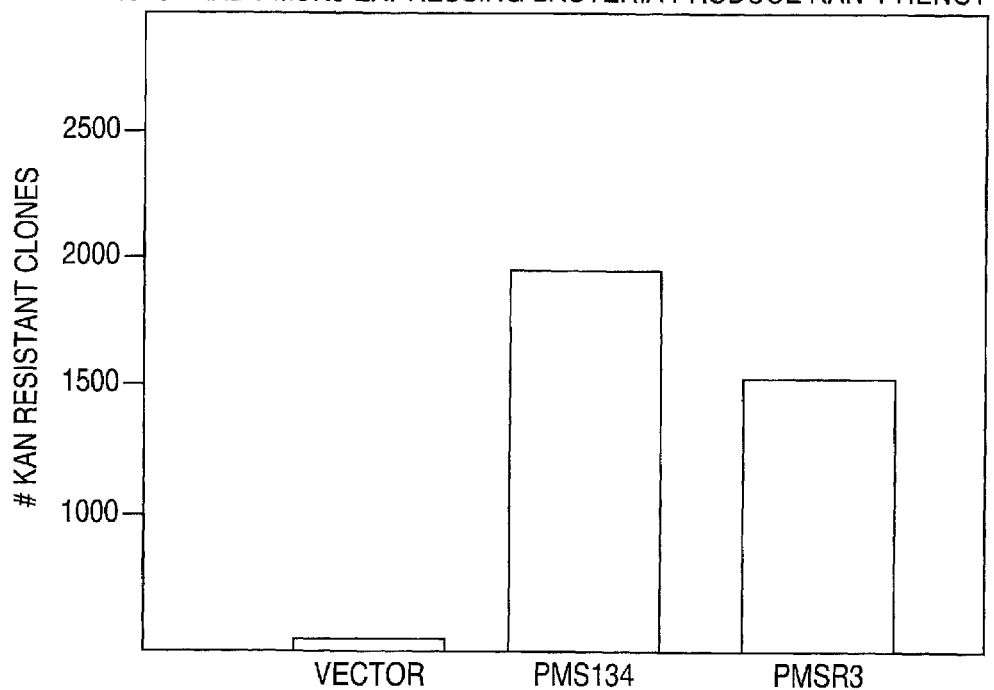
FIG. 4. Number of Kanamycin Resistant PMS134, PMSR3 and vector control BL21 clones. IPTG-induced strains were grown and plated onto AMP and KAN plates and grown for 18 hours at 37° C. to identify number of KAN resistant clones due to genetic alteration.

Kanamycin-resistant assays using BL21 cells expressing the V5-tagged or untagged PMS134 or PMSR3 polypeptides were carried out as described above. BL21 bacterial cells that harbor the empty vector, pT7-PMS134 or pT7-PMSR3 were grown overnight in LB supplemented with 100 μg/ml ampicillin. The overnight cultures were diluted 1:100 into fresh ampicillin containing medium and grown for 2.5 hours at 37° C. with continuous shaking. When the cells reached an optical density (OD) of 0.6, measured at 600 nm, IPTG was added to each culture to a final concentration of 0.5 mM. Cells were incubated for 24, and 48 hours; at those time points cells were removed for SDS-PAGE analysis and plating (see above). BL21/pT7 (empty vector), BL21/pT7-PMS134, and BL21/pT7-R3 cells were plated onto LB plates, LB plates that contained 100 μg/ml ampicillin, and plates that contain 50 μg/ml Kanamycin. The equivalent of 1×10⁷ cells/plate were spread onto the plates. BL21 cells that harbor the empty vector are capable of growth on LB plates as well as LB plates that contain 10 μg/ml ampicillin; that is as expected since the pT7 expression vector renders the cells ampicillin resistant. The vector only control is not capable of growth on Kanamycin. After 24 hr IPTG-induction PMS134 or PMSR3 cells had a significant number of KAN resistant cells while none were observed in BL21 parental cells grown under similar conditions (FIG. 4). Moreover, BL21 cells containing the PMS134 or PMSR3 genes under non-IPTG-induced conditions failed to produce any KAN resistant clones demonstrating the need for expression of the PMS polypeptides for hypermutability. A summary outlining the data and number of Kanamycin resistant bacterial clones is provided in TABLE 1.

TABLE 1

Generation of Kanamycin resistant clones via MMR deficiency

| STRAIN | # CELLS SEEDED | AMP$^R$ colonies | KAN$^R$ colonies | FREQUENCY |
|---|---|---|---|---|
| DH10B VEC | 50,000 | 62,000 | 0 | 0 |
| DH10B PMS134 | 50,000 | 43,146 | 23 | $53 \times 10^{-4}$ |
| BL21 VEC | 500,000 | 520,800 | 0 | 0 |
| BL21 T7-Ea-PMS134V5 | 500,000 | 450,000 | 2,245 | $4.9 \times 10^{-3}$ |
| BL21 T7-Ea-PMSR3V5 | 500,000 | 500,000 | 1,535 | $3.1 \times 10^{-3}$ |

These data demonstrate and enable the proof-of-concept that the use of the dominant negative MMR genes is a viable approach to creating hypermutable bacteria that can lead to the generation of phenotypically diverse offspring when put under selective conditions.

Figure 5A:
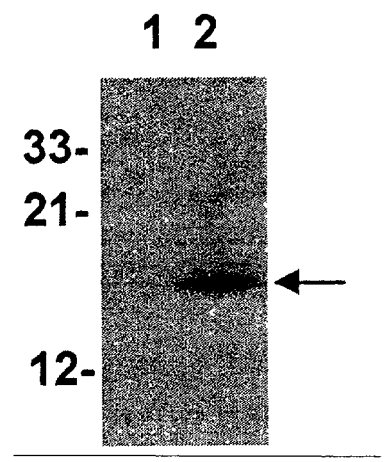
FIG. 5. (A) Western blot of steady-state ATPMS134flag in IPTG-treated samples in DH10B. Lysates from untransfected cells (lane 1) and a bacterial clone expressing the Arabidopsis thaliana PMS134 truncated protein with a FLAG epitope fused to the C-terminus (ATPMS134flag) (lane 2) were electrophoresed on SDS-PAGE gels. Blots were probed with an anti-FLAG monoclonal antibody directed to the FLAG epitope. (B) Number of Kanamycin Resistant ATPMS134flag and vector control DH10B clones. IPTG-induced strains were grown and plated onto AMP and KAN plates and grown for an additional 18 hours at 37° C. to identify number of KAN resistant clones due to genetic alteration.
Figure 5B:
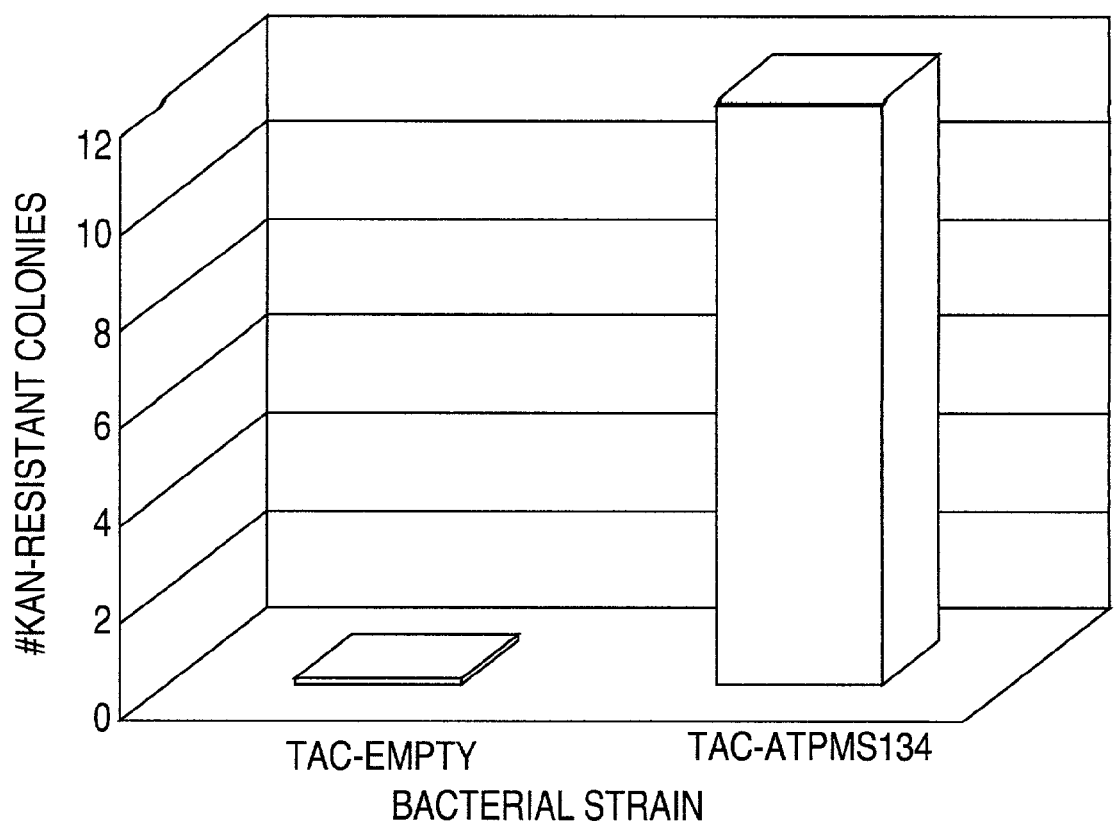

Using the same protocol as listed above and the same cloning strategy, a truncated PMS2 homolog from the *Arabidopsis thaliana* plant, which was cloned by degenerate PCR from an *Arabidopsis thaliana* cDNA library (Strategene), was found to give a similar enhancement of genetic hypermutability in DH5alpha bacteria FIG. 5. For detection purposes, we fused a FLAG epitope to the C-terminus of the PMS134 polypeptide using PCR and an antisense primer directed to the 134 codon region of the *Arabidopsis* PMS2 homolog followed by a FLAG epitope and 2 termination codons. The resultant fusion was termed ATPMS134-flag. The AT PMS134-flag gene was then cloned into the IPTG-inducible TACLAC expression vector and transfected into DH5alpha cells. Western blot of bacteria transfected with an IPTG-inducible expression vector carrying a truncated version (codons 1–134) of the Arabidopsis thaliana PMS2 homolog using the anti-FLAG antibody demonstrated the inducibility and steady-state protein levels of the chimeric gene. FIG. 5A shows the western blot containing protein from an untransfected cell (lane 1) and a bacterial clone expressing the Arabidopsis PMS2-134 truncated protein (lane 2). Following the mutagenesis protocol described above, bacterial cells expressing the ATPMS134 protein were found to have an increase in the number of KAN resistant cells (12 clones) in contrast to cells expressing the empty vector that yielded no KAN resistant clone.

Bacterial cells such as the pT7-PMS134 and pT7-R3 harboring BL21 cells; the TACLACPMS134 DH10B; the TACLACMLH1 DH10B cells; or the TACLAC-ATPMS134flag DH5alpha cells are capable of growth on LB, LB/ampicillin and LB/KAN plates because the cells have acquired mutations within their genome that render the cell drug resistant. Cells that express dominant negative MMR genes have altered the mismatch control pathway of the microbe, presumably altering a gene or a set of genes that control resistance to kanamycin. A new output trait, Kanamycin-resistance, is generated by expression of the dominant negative MMR gene in these cells. These data demonstrate the ability of dominant negative MMR genes to produce hypermutability across a wide array of bacterial strains to produce new output traits such as Kanamycin resistance.

EXAMPLE 3

Dominant Negative MMR Genes Can Produce New Genetic Variants and Commercially Viable Output Traits in Prokaryotic Organisms The data presented in EXAMPLE 2 show the ability to generate genetic alterations and new phenotypes in bacterial strains expressing dominant negative MMR genes. In this EXAMPLE we teach the utility of this method to create prokaryotic strains with commercially relevant output traits.

Generation of Heat-resistant Producer Strains

One example of commercial utility is the generation of heat-resistant recombinant protein producer strains. In the scalable process of recombinant manufacturing, large-scale fermentation of prokaryotes results in the generation of heat, which leads to suboptimal growth conditions for the producer strain and thus resulting in lower recombinant protein yields. In order to circumvent this problem, we employed the use of DH10B bacteria containing the inducible TACLACPMS134 gene. Briefly, cells were grown in 5 ml LB shake flasks containing ampicillin and IPTG-induced for 0, 24 and 48 hrs at 37C. Cultures were harvested and then incubated at 100C. for 0, 1 or 10 minutes (times at which 100% of the wild-type strain perishes) and 100 μl aliquots (equivalent to 250,000 cells) were plated onto LB agar plates containing ampicillin to identify heat resistant clones. Table 2 shows a typical experiment whereby cells containing the TACLACPMS134 gene generated a significant number of heat-resistant clones after 48 hours of PMS134 induction and hypermutation via MMR blockade. No or a few clones were observed in the uninduced or 24 hr induced conditions respectively suggesting the needs for multiple rounds of genetic mutation to produce genes that are capable of allowing bacteria to survive under harsh conditions. Similar results were observed with other dominant negative mutants such as the PMSR2, PMSR3, and the human MLH1 proteins (not shown).

TABLE 2

Generation of heat-resistant clones via MMR deficiency

| Treatment | Heated 0 min | Heated 1 min | Heated 10 min |
|---|---|---|---|
| TACLACVEC 0 hr IPTG | 250,000 +/− 7,500 | 0 | 0 |
| TACLACPMS134 0 hr IPTG | 265,000 +/− 2,000 | 0 | |
| TACLACVEC 24 hr IPTG | 274,000 +/− 12,000 | 1 +/− 0 | 0 |
| TACLACPMS134 24 hr IPTG | 240,000 +/− 9,400 | 5 +/− 2 | 0 |
| TACLACVEC 48 hr IPTG | 256,000 +/− 12,000 | 0 | 0 |
| TACLACPMS134 48 hr IPTG | 252,000 +/− 14,000 | 65 +/− 8 | 3 +− 1 |

Generation of High Recombinant Protein Producer Strains.

Figure 6:
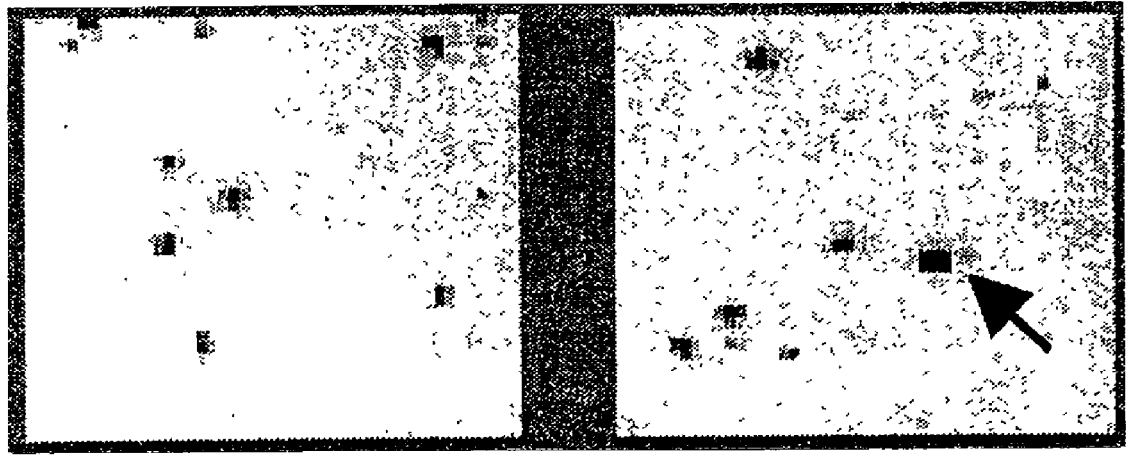
FIG. 6. Generation of high recombinant producer BGAL-MOR lines in PMS134 expressing DH5alpha host strains.

Next, we tested the ability of bacteria expressing dominant negative MMR genes to produce subclones with enhanced recombinant protein production. In these experiments again we employed the DH10B cells containing the TACLACPMS134 inducible vector plus the pTLACZ vector, which constitutively expresses the β-galactosidase gene. Analysis of individual clones containing the TACLACPMS134 and pTLACZ vector typically produces 10–20 μg/ml of LACZ protein via shake flask fermentation after IPTG induction for 24 hours. To test the hypothesis that high recombinant producer strains can be generated by decreased MMR in bacterial strains, we induced the TACLACPMS134-pTLACZ cells for 48 hours with IPTG as described above. We then diluted the culture 1:50 in LB medium, grew the strain for 24 hours, and plated 10 μls of culture (diluted in 300 μls of LB) onto LB amp-XGAL plates to identify candidate clones that produce robust levels of recombinant LACZ protein. As a control, uninduced cells were treated similarly and plated onto LB amp-XGAL plates. Analysis of the plates revealed a number of bacterial colonies exhibiting a number of clones with an intense BLUE staining in the TACLACPMS134/pTLACZ cells induced with IPTG but none were observed in uninduced clones (FIG. 6). To confirm that these clones produced an enhanced level of LACZ, we expanded 2 clones with an average BLUE stain (BGAL-C1 and BGAL-C2) and 10 clones with a robust BLUE staining (BGAL-MOR1 to BGAL-MOR10). We grew all clones in LB AMP for 24 hours without IPTG and replated the clones. Six out of ten BGAL-MOR clones resulted in a more robust β-gal stain in situ as compared to control "average" cells (BGALC1 and C2). We next performed a more quantitative assay using a β-gal ELISA assay. Briefly, 2 mls of cell centrifuged at 10,000 gs for 10 minutes and resuspended in 0.5 mls of 0.25M Tris, pH 7.5 plus 0.0001% Tween-20. Cells were freeze-thawed 4×'s and vortexed for 4 minutes at room temperature. Lysates were cleared of debris by centrifugation and supernatants were collected. Protein extracts were quantified for total protein using the Bradford assay (Bio-Rad) as described by the manufacturer. Plate ELISAs were carried out by coating 96 well maxisorb (NUNC) plates with 0.1 mls of a 1 μg/ml (diluted in PBS pH7.0) bacterial extract solution and a dose range of recombinant β-GAL (Sigma) from 0.001 to 10 mg/ml. All samples were plated in triplicates. Plates were coated for 2 hours, washed 2 times with PBS and blocked with 0.2 mls of PBS plus 5% powdered milk for 30 minutes. Next, plates were washed once with PBS and incubated with an anti-β3-galactosidase monoclonal antibody that recognizes both native and denatured forms (Sigma) for 2 hours. Plates were then washed 3 times with PBS and incubated with 0.1 mls of an anti-mouse horseradish peroxidase conjugated antibody for 1 hour at room temperature. Plates were washed 3 times with PBS and incubated with TMB ELISA substrate (BioRad) for 15 to 30 minutes. Reactions were stopped with 0. IN $H_2SO_4$ and read on a BioRAD plate reader at 415 nm. The control clones produced roughly 9 and 13 μgs /ml of β-gal while BGAL-MOR clones 2, 3 and 9 produced 106, 82 and 143 μgs /ml of β-gal. To determine if reason that these clones produced more β-gal was due to mutations in the plasmid promoter elements, we isolated the pTLACZ plasmid and retransfected it into DH10B cells as described above. In situ analysis found the resultant clones to produce similar amount of β-gal as that of the control. These data suggest that the BGAL-MOR 2, 3, and 9 hosts had alterations, which results in elevated expression and/or stability of recombinant proteins.

To determine if the enhanced in situ β-gal expression that was observed in BGAL-MOR clones 1, 5, and 6, which did not appear to have enhanced β-gal protein levels (had less than 15 μg/ml as determined by ELISA) was authentic, we performed a more quantitative assay on these lines plus the BGAL-MOR 9, the BGALC1 and C2 lines as control. Cells containing an empty vector (without a LACZ gene) were used as negative control. To measure β-gal activity, we employed a calorimetric β-gal substrate assay using CPRG (Roche) as described (31). Briefly, 5 μgs of protein extract isolated for ELISA analysis (described above) were analyzed using a plate assay. Protein was added to buffer containing 45 mM 2-mercaptoethanol, 1 mM $MgCl_2$, 0.1 M $NaPO_4$ and 0.6 mg/ml Chlorophenol red-β-D-galactopyranoside (CPRG, Roche). Reactions were incubated for 1 hour, terminated by the addition of 0.5 M $Na_2CO_3$, and analyzed by spectrophotometry at 576 nm in a BioRad plate reader. Analysis of these extracts confirmed our in situ data that these cells did have increased β-gal activity (TABLE 3).

TABLE 3

Generation of bacterial clones with increased β-gal enzymatic activity via MMR deficiency.

| Clone | β-gal protein (μg/ml) | β-gal activity (O.D. 576) |
|---|---|---|
| BGAL-C1 | 9 | 0.413 +/− .092 |
| BGAL-C2 | 13 | 0.393 +/− .105 |
| BGAL-MOR1 | 14 | 0.899 +/− .134 |
| BGAL-MOR5 | 13 | 0.952 +/− .133 |
| BGAL-MOR6 | 15 | 0.923 +/− .100 |
| BGAL-MOR9 | 143 | 0.987 +/− .106 |
| Empty vector | — | 0.132 +/− .036 |

Because there was no observable increase in the amount of β-gal protein one likely hypothesis is that the β-gal gene structure was mutated during the hypermutability growth stage and now produces a more active enzyme. Sequence analysis confirms that this may be the reason for enhanced activity in a subset of clones.

Together, these data demonstrate the ability to produce genetically altered prokaryotic host strains using dominant negative MMR genes to generate commercially valuable output traits such as high recombinant protein producer lines and structurally altered enzymes with enhanced activities.

EXAMPLE 4

Mutations in the Host Genome Generated by Defective MMR are Genetically Stable

As described in EXAMPLE 2 and 3, manipulation of the MMR pathway in microbes results in alterations within the host genome and the ability to select for a novel output traits. It is important that the mutations introduced as a result of defective MMR is genetically stable and passed on to daughter cells once a desired output pathway is established. To determine the genetic stability of mutations introduced into the microbial genome the following experiment was performed. Five independent colonies from pT7-PMS 134 and pT7-PMSR3 that are kanamycin resistance were grown overnight from an isolated colony in 5 ml of LB. Next, 1 μL of the overnight culture from these cultures were inoculated into another 5 mL of LB and grown overnight to saturation. Under these growth conditions the microbial cells have divided over 20 generations. Therefore, if the new output trait generated by alteration of MMR is unstable, the cells should "revert" back from kanamycin resistance to kanamycin sensitivity. Cells were plated onto LB plates and incubated overnight at 37° C. Next, the colonies (about 1,000/plate) were replica plated to LB, $LB^{amp100}$, and $LB^{kan50}$ plates and incubated at 37° C. overnight. Analysis of clones from these studies reveal that a strict correlation occurs with loss of dominant negative MMR expression and phenotype stability. No loss of KAN resistant clones generated in Example 3 were observed when cells were grown in the absence of IPTG (not expressing PMS134), while 5 revertants out of 1200 were observed in clones the were continually grown in IPTG (express PMS134). Extended culturing of cells and replica plating found no reversions of KAN resistance in cultures grown in the absence of IPTG, which produce no PMS134 as determined by western blot (data not shown).

These data demonstrate the utility of employing inducible expression systems and dominant negative MMR genes in prokaryotes to generate genetically altered strains for commercial applications such as but not limited to enhanced recombinant manufacturing and biotransformation that can then in turn be restored to a genetically stable host with a "fixed" new genotype that is suitable for commercial processes.

EXAMPLE 5

Enhanced Generation of MMR-Defective Bacteria and Chemical Mutagens for the Generation of New Output Traits It has been previously documented that MMR deficiency yields to increased mutation frequency and increased resistance to toxic effects of chemical mutagens (CM) and their respective analogues such as but not limited to those as: ethidium bromide, EMS, MNNG, MNU, Tamoxifen, 8-Hydroxyguanine, as well as others listed but not limited to in publications by: Khromov-Borisov, N. N., et. al. (Mutat. Res. 430:55–74, 1999); Ohe, T., et. al. (Mutat. Res. 429: 189–199, 1999); Hour, T. C. et. al. (Food Chem. Toxicol. 37:569–579, 1999); Hrelia, P., et. al. (Chem. Biol. Interact. 118:99–111, 1999); Garganta, F., et. al. (Environ. Mol. Mutagen. 33:75–85, 1999); Ukawa-Ishikawa S., et. al. (Mutat. Res. 412:99–107, 1998); the website having the URL address: www. host server, ehs.utah.edu domain name, ohh directory, mutagens subdirectory, etc. To demonstrate the ability of CMs to increase the mutation frequency in MMR defective bacterial cells, we exposed T7-PMS134 BL21 cells to CMs.

T7-PMS134 cells and empty vector control cells were grown with IPTG for 48 hours and then diluted 1:50 in LB plus IPTG and increasing amounts of ethyl methane sulfonate (EMS) from 0, 1, 10, 50, 100, and 200 μM. 10 μL aliquots of culture (diluted in 300 μl LB) were plated out on LB agar plus ampicillin plates and grown overnight at 37C. The next day plates were analyzed for cell viability as determined by colony formation. Analysis found that while no significant difference in colony number was observed between the pT7-PMS134 and control at the 0, 1 , or 10 μM concentrations (all had >1000 colonies), the number of control cells were reduced to 30 and 0 at the 50 and 100 μM concentrations, respectively. No difference was observed in the pT7-PMS134 cells treated with 0, 1, 10 or 50 μM, while a 3 fold reduction was observed in cultures treated with 100 μM EMS. The 200 μM treatment was toxic for both lines. These data demonstrate the ability of MMR deficiency to protect prokaryotes against the toxic effects of DNA akylating agents and provides a means to generate a wider range of mutations that can lead to an increased number of genetic variations and an increase in the number of new biochemical activities within host proteins to produce new output traits for commercial applications.

To confirm that MMR deficient bacterial cells treated with CM can result in an increased mutation rate and produce a greater number of variants, we cultured pT7-PMS134 cells and empty vector controls in the presence of IPTG for 48 hours, followed by dilution and regrowth in 25 µM EMS for 24 hours as described above. Cells were plated out on 100 mM petri dishes containing amplicillin or KAN and scored for KAN resistance. Analysis revealed that an 11-fold increase in the generation of KAN resistant cells were found in pT7-Ea-PMS134V5 cells in contrast to control cells.

These data demonstrate the use of employing a regulated dominant negative MMR system plus chemical mutagens to produce enhanced numbers of genetically altered prokaryotic strains that can be selected for new output traits. This methods is now useful generating such organisms for commercial applications such as but not limited to recombinant manufacturing, biotransformation, and altered biochemicals (biotransformation) with enhanced activities for manufacturing purposes and gene discovery for pharmaceutical compound development.

EXAMPLE 6

Alternative Methods to Inhibition of Bacterial MMR Activity

The inhibition of MMR activity in a host organism can be achieved by introducing a dominant negative allele as shown in EXAMPLES 2 and 3. This application also teaches us the use of using regulated systems to control MMR in prokaryotes to generate genetic diversity and output traits for commercial applications. Other ways to regulate the suppression of MMR activity of a host is by using genetic recombination to knock out alleles of a MMR gene that can be spliced out such after selection using a system such as the CRE-Lox system; 2) blocking MMR protein dimerization with other subunits (which is required for activity) by the introduction of polypeptides or antibodies into the host via transfection methods routinely used by those skilled in the art; or 3) decreasing the expression of a MMR gene using anti-sense oligonucleotides.

MMR gene knockouts. We intend to generate disrupted targeting vectors of a particular MMR gene and introduce it into the genome of bacteria using methods standard in the art. Bacteria exhibiting hypermutability will be useful to produce genetically diverse offspring for commercial applications. Bacteria will be confirmed to have lost the expression of the MMR gene using standard northern and biochemical techniques (as described in reference 32). MMR gene loci can be knocked out, strains selected for new output traits and MMR restored by introducing a wildtype MMR gene to complement the KO locus. Other strategies include using KO vectors that can target a MMR gene locus, select for host output traits and then have the KO vector "spliced" from the genome after strain generation. This process could be performed using systems such as but not limited to CRE-Lox.

Blocking peptides. MMR subunits (MutS and MutL proteins) interact to form active MMR complexes. Peptides are able to specifically inhibit the binding of two proteins by competitive inhibition. The use of peptides or antibodies to conserved domains of a particular MMR gene can be introduced into prokaryotic cells using lipid transfer methods that are standard in the art. Bacteria will be confirmed to have lost the expression of the MMR gene using standard northern and biochemical techniques (as described in reference 32). Bacteria exhibiting hypermutability will be useful to produce genetically diverse sibs for commercial applications.

Discussion

The results described above will lead to several conclusions. The expression of dominant negative MMR proteins results in an increase in hypermutability in bacteria. This activity is due to the inhibition of MMR biochemical activity in these hosts. This method provides a claim for use of dominant negative MMR genes and their encoded products for the creation of hypermutable bacteria to produce new output traits for commercial applications.

Examples of MMR Genes and Encoded Polypeptides

```
Yeast MLH1 cDNA (accession number U07187) (SEQ ID NO: 5)

1     aaataggaat gtgatacctt ctattgcatg caaagatagt gtaggaggcg ctgctattgc 61    caaagacttt tgagaccgct tgctgtttca ttatagttga ggagttctcg aagacgagaa 121   attagcagtt ttcggtgttt agtaatcgcg ctagcatgct aggacaattt aactgcaaaa 181   ttttgatacg atagtgatag taaatggaag gtaaaaataa catagaccta tcaataagca 241   atgtctctca gaataaaagc acttgatgca tcagtggtta acaaaattgc tgcaggtgag 301   atcataatat cccccgtaaa tgctctcaaa gaaatgatgg agaattccat cgatgcgaat 361   gctacaatga ttgatattct agtcaaggaa ggaggaatta aggtacttca aataacagat 421   aacggatctg gaattaataa agcagacctg ccaatcttat gtgagcgatt cacgacgtcc 481   aaattacaaa aattcgaaga tttgagtcag attcaaacgt atggattccg aggagaagct 541   ttagccagta tctcacatgt ggcaagagtc acagtaacga caaaagttaa agatgacaga 601   tgtgcatgga gagtttcata tgcagaaggt aagatgttgg aaagccccaa acctgttgct 661   ggaaaagacg gtaccacgat cctagttgaa gaccttttt tcaatattcc ttctagatta 721   agggccttga ggtcccataa tgatgaatac tctaaaatat tagatgttgt cgggcgatac
```

-continued

```
 781 gccattcatt ccaaggacat tggctttct tgtaaaagt tcggagactc taattattct
 841 ttatcagtta aaccttcata tacagtccag gataggatta ggactgtgtt caataaatct
 901 gtggcttcga atttaattac ttttcatatc agcaaagtag aagatttaaa cctggaaagc
 961 gttgatggaa aggtgtgtaa tttgaatttc atatccaaaa agtccatttc attaattttt
1021 ttcattaata atagactagt gacatgtgat cttctaagaa gagctttgaa cagcgtttac
1081 tccaattatc tgccaaaggg cttcagacct tttatttatt tgggaattgt tatagatccg
1141 gcggctgttg atgttaacgt tcacccgaca agagagagg ttcgtttcct gagccaagat
1201 gagatcacag agaaaatcgc caatcaattg cacgccgaat tatctgccat tgatacttca
1261 cgtactttca aggcttcttc aatttcaaca aacaagccag agtcattgat accatttaat
1321 gacaccatag aaagtgatag gaataggaag agtctccgac aagcccaagt ggtagagaat
1381 tcatatacga cagccaatag tcaactaagg aaagcgaaaa gacaagagaa taaactagtc
1441 agaatagatg cttcacaagc taaaattacg tcattttat cctcaagtca acagttcaac
1501 tttgaaggat cgtctacaaa gcgacaactg agtgaaccca aggtaacaaa tgtaagccac
1561 tcccaagagg cagaaaagct gacactaaat gaaagcgaac aaccgcgtga tgccaataca
1621 atcaatgata atgatttgaa ggaccaacct aagaagaaac aaaagttggg ggattataaa
1681 gttccaagca ttgccgatga cgaaaagaat gcactcccga tttcaaaaga cgggtatatt
1741 agagtaccta aggagcgagt taatgttaat cttacgagta tcaagaaatt gcgtgaaaaa
1801 gtagatgatt cgatacatcg agaactaaca gacattttg caaatttgaa ttacgttggg
1861 gttgtagatg aggaaagaag attagccgct attcagcatg acttaaagct tttttaata
1921 gattacggat ctgtgtgcta tgagctattc tatcagattg gtttgacaga cttcgcaaac
1981 tttggtaaga taaacctaca gagtacaaat gtgtcagatg atatagtttt gtataatctc
2041 ctatcagaat ttgacgagtt aaatgacgat gcttccaaag aaaaaataat tagtaaaata
2101 tgggacatga gcagtatgct aaatgagtac tattccatag aattggtgaa cgatggtcta
2161 gataatgact aaagtctgt gaagctaaaa tctctaccac tacttttaaa aggctacatt
2221 ccatctctgg tcaagttacc atttttata tatcgcctgg gtaaagaagt tgattgggag
2281 gatgaacaag agtgtctaga tggtatttta agagagattg cattactcta tatacctgat
2341 atggttccga aagtcgatac actcgatgca tcgttgtcag aagacgaaaa agcccagttt
2401 ataaatagaa aggaacacat atcctcatta ctagaacacg ttctcttccc ttgtatcaaa
2461 cgaaggttcc tggcccctag acacattctc aaggatgtcg tggaaatagc caaccttcca
2521 gatctataca agttttga gaggtgttaa ctttaaaacg ttttggctgt aataccaaag
2581 tttttgttta tttcctgagt gtgattgtgt tcatttgaa agtgtatgcc ctttccttta
2641 acgattcatc cgcgagattt caaggatat gaaatatggt tgcagttagg aaagtatgtc
2701 agaaatgtat attcggattg aaactcttct aatagttctg aagtcacttg gttccgtatt
2761 gttttcgtcc tcttcctcaa gcaacgattc ttgtctaagc ttattcaacg gtaccaaaga
2821 cccgagtcct tttatgagag aaaacatttc atcatttttc aactcaatta tcttaatatc
2881 atttttgtagt attttgaaaa caggatggta aaacgaatca cctgaatcta gaagctgtac
2941 cttgtcccat aaaagtttta atttactgag cctttcggtc aagtaaacta gtttatctag
3001 ttttgaaccg aatattgtgg gcagatttgc agtaagttca gttagatcta ctaaaagttg
3061 tttgacagca gccgattcca caaaaatttg gtaaaggag atgaaagaga cctcgcgcgt
3121 aatggtttgc atcaccatcg gatgtctgtt gaaaaactca cttttgcat ggaagttatt
```

-continued 3181 aacaataaga ctaacgatta ccttagaata atgtataa

Yeast MLH1 protein (accession number U07187) (SEQ ID NO: 15)

MSLRIKALDASVVNKIAAGEIIISPVNALKEMMENSIDANATMI

DILVKEGGIKVLQITDNGSGINKADLPILCERFTTSKLQKFEDLSQIQTYGFRGEALA

SISHVARVTVTTKVKEDRCAWRVSYAEGKMLESPKPVAGKDGTTILVEDLFFNIPSRL

RALRSHNDEYSKILDVVGRYAIHSKDIGFSCKKFGDSNYSLSVKPSYTVQDRIRTVFN

KSVASNLITFHISKVEDLNLESVDGKVCNLNFISKKSISLIFFINNRLVTCDLLRRAL

NSVYSNYLPKGFRPFIYLGIVIDPAAVDVNVHPTKREVRFLSQDEIIEKIANQLHAEL

SAIDTSRTFKASSISTNKPESLIPFNDTIESDRNRKSLRQAQVVENSYTTANSQLRKA

KRQENKLVRIDASQAKITSFLSSSQQFNFEGSSTKRQLSEPKVTNVSHSQEAEKLTLN

ESEQPRDANTINDNDLKDQPKKKQKLGDYKVPSIADDEKNALPISKDGYIRVPKERVN

VNLTSIKKLREKVDDSIHRELTDIFANLNYVGVVDEERRLAAIQHDLKLFLIDYGSVC

YELFYQIGLTDFANFGKINLQSTNVSDDIVLYNLLSEFDELNDDASKEKIISKIWDMS

SMLNEYYSIELVNDGLDNDLKSVKLKSLPLLLKGYIPSLVKLPFFIYRLGKEVDWEDE

QECLDGILREIALLYIPDMVPKVDTLDASLSEDEKAQFINRKEHISSLLEHVLFPCIK

RRFLAPRHILKDVVEIANLPDLYKVFERC

Mouse PMS2 protein (SEQ ID NO: 16)

MEQTEGVSTE CAKAIKPIDG KSVHQICSGQ VILSLSTAVK ELIENSVDAG ATTIDLRLKD  60

YGVDLIEVSD NGCGVEEENF EGLALKHHTS KIQEFADLTQ VETFGFRGEA LSSLCALSDV 120

TISTCHGSAS VGTRLVFDHN GKITQKTPYP RPKGTTVSVQ HLFYTLPVRY KEFQRNIKKE 180

YSKMVQVLQA YCIISAGVRV SCTNQLGQGK RHAVVCTSGT SCMKENIGSV FGQKQLQSLI 240

PFVQLPPSDA VCEEYGLSTS GRHKTFSTFR ASFHSARTAP GGVQQTGSFS SSIRGPVTQQ 300

RSLSLSMRFY HMYNRHQYPF VVLNVSVDSE CVDINVTPDK RQILLQEEKL LLAVLKTSLI 360

GMFDSDANKL NVNQQPLLDV EGNLVKLHTA ELEKPVPGKQ DNSPSLKSTA DEKRVASISR 420

LREAFSLHPT KEIKSRGPET AELTRSFPSE KRGVLSSYPS DVISYRGLKG SQDKLVSPTD 480

SPGDCMDREK IEKDSGLSST SAGSEEEFST PEVASSFSSD YNVSSLEDRP SQETINCGDL 540

DCRPPGTGQS LKPEDHGYQC KALPLARLSP TNAKRFKTEE RPSNVNISQR LPGPQSTSAA 600

EVDVAIKMNK RIVLLEFSLS SLAKRMKQLQ HLKAQNKHEL SYRKFRAKIC PGENQAAEDE 660

LRKEISKSMF AEMEILGQFN LGFIVTKLKE DLFLVDQHAA DEKYNFEMLQ QHTVLQAQRL 720

ITPQTLNLTA VNEAVLIENL EIFRKNGFDF VIDEDAPVTE RAKLISLPTS KNWTFGPQDI 780

DELIFMLSDS PGVMCRPSRV RQMFASRACR KSVMIGTALN ASEMKKLITM MGEMDHPWNC 840

PHGRPTMRHV ANLDVISQN                                                859

Mouse PMS2 cDNA (SEQ ID NO: 6)

gaattccggt gaaggtcctg aagaatttcc agattcctga gtatcattgg aggagacaga  60
taacctgtcg tcaggtaacg atggtgtata tgcaacagaa atgggtgttc ctggagacgc 120
gtcttttccc gagagcggca ccgcaactct cccgcggtga ctgtgactgg aggagtcctg 180
catccatgga gcaaaccgaa ggcgtgagta cagaatgtgc taaggccatc aagcctattg 240
atgggaagtc agtccatcaa atttgttctg gcaggtgat actcagttta agcaccgctg 300
tgaaggagtt gatagaaaat agtgtagatg ctggtgctac tactattgat ctaaggctta 360
aagactatgg ggtggacctc attgaagttt cagacaatgg atgtgggta gaagaagaaa 420

-continued

```
actttgaagg tctagctctg aaacatcaca catctaagat tcaagagttt gccgacctca    480
cgcaggttga aactttcggc tttcgggggg aagctctgag ctctctgtgt gcactaagtg    540
atgtcactat atctacctgc cacgggtctg caagcgttgg gactcgactg gtgtttgacc    600
ataatgggaa aatcacccag aaaactccct accccgacc taaaggaacc acagtcagtg     660
tgcagcactt attttataca ctacccgtgc gttacaaaga gtttcagagg aacattaaaa    720
aggagtattc caaaatggtg caggtcttac aggcgtactg tatcatctca gcaggcgtcc    780
gtgtaagctg cactaatcag ctcggacagg ggaagcggca cgctgtggtg tgcacaagcg    840
gcacgtctgg catgaaggaa aatatcgggt ctgtgtttgg ccagaagcag ttgcaaagcc    900
tcattccttt tgttcagctg cccctagtg acgctgtgtg tgaagagtac ggcctgagca      960
cttcaggacg ccacaaaacc ttttctacgt ttcgggcttc atttcacagt gcacgcacgg   1020
cgccgggagg agtgcaacag acaggcagtt tttcttcatc aatcagaggc cctgtgaccc    1080
agcaaaggtc tccaagcttg tctatgaggt tttatcacat gtataaccgg catcagtacc    1140
catttgtcgt ccttaacgtt tccgttgact cagaatgtgt ggatattaat gtaactccag    1200
ataaaaggca aattctacta caagaagaga agctattgct ggccgtttta aagacctcct    1260
tgataggaat gtttgacagt gacgcaaaca agcttaatgt caaccagcag ccactgctag    1320
atgttgaagg taacttagta aagctgcata ctgcagaact agaaaagcct gtgccaggaa    1380
agcaagataa ctctccttca ctgaagagca cagcagacga gaaaagggta gcatccatct    1440
ccaggctgag agaggccttt tctcttcatc ctactaaaga gatcaagtct aggggtccag    1500
agactgctga actgacacgg agttttccaa gtgagaaaag gggcgtgtta tcctcttatc    1560
cttcagacgt catctcttac agaggcctcc gtggctcgca ggacaaattg gtgagtccca    1620
cggacagccc tggtgactgt atggacagag agaaaataga aaaagactta gggctcagca    1680
gcacctcagc tggctctgag gaagagttca gcaccccaga agtggccagt agctttagca    1740
gtgactataa cgtgagctcc ctagaagaca gaccttctca ggaaaccata aactgtggtg    1800
acctggactg ccgtcctcca ggtacaggac agtccttgaa gccagaagac catggatatc    1860
aatgcaaagc tctacctcta gctcgtctgt caccacaaa tgccaagcgc ttcaagacga    1920
aggaaagacc ctcaaatgtc aacattcctc aaagattgcc tggtcctcag agcacctcag    1980
cagctgaggt cgatgtagcc ataaaaatga ataagagaat cgtgctcctc gagttctctc    2040
tgagttctct agctaagcga atgaagcagt tacagcacct aaaggcgcag aacaaacatg    2100
aactgagtta cagaaaattt agggccaaga tttgccctgg agaaaaccaa gcagcagaag    2160
atgaactcag aaaagagatt agtaaatcga tgtttgcaga gatggagatc ttgggtcagt    2220
ttaacctggg atttatagta accaaactga agaggacct cttcctggtg gaccagcatg    2280
ctgcggatga aagtacaac tttgagatgc tgcagcagca cacggtgctc caggcgcaga    2340
ggctcatcac accccagact ctgaacttaa ctgctgtcaa tgaagctgta ctgatagaaa    2400
atctggaaat attcagaaag aatggctttg actttgtcat tgatgaggat gctccagtca    2460
ctgaaagggc taaattgatt tccttaccaa ctagtaaaaa ctggaccttt ggaccccaag    2520
atatagatga actgatcttt atgttaagtg acagccctgg ggtcatgtgc cggccctcac    2580
gagtcagaca gatgtttgct tccagagcct gtcggaagtc agtgatgatt ggaacgcgc     2640 tcaatgcgag cgagatgaag aagctcatca cccacatggg tgagatggac cacccctgga    2700 actgcccca cggcaggcca accatgaggc acgttgccaa tctggatgtc atctctcaga    2760
actgacacac cccttgtagc atagagttta ttacagattg ttcggtttgc aaagagaagg    2820
```

-continued

```
ttttaagtaa tctgattatc gttgtacaaa aattagcatg ctgctttaat gtactggatc 2880
catttaaaag cagtgttaag gcaggcatga tggagtgttc ctctagctca gctacttggg 2940
tgatccggtg ggagctcatg tgagcccagg actttgagac cactccgagc cacattcatg 3000
agactcaatt caaggacaaa aaaaaaaaga tattttttgaa gccttttaaa aaaaaa 3056
``` human PMS2 protein (SEQ ID NO: 17)

```
MKQLPAATVR LLSSSQIITS VVSVVKELIE NSLDAGATSV DVKLENYGFD KIEVRDNGEG   60

IKAVDAPVMA MKYYTSKINS HEDLENLTTY GFRGEALGSI CCIAEVLITT RTAADNFSTQ  120

YVLDGSGHIL SQKPSHLGQG TTVTALRLFK NLPVRKQFYS TAKKCKDEIK KIQDLLMSFG  180

ILKPDLRIVF VHNKAVIWQK SRVSDHKMAL MSVLGTAVMN NMESFQYHSE ESQIYLSGFL  240

PKCDADHSFT SLSTPERSFI FINSRPVHQK DILKLIRHHY NLKCLKESTR LYPVFFLKID  300

VPTADVDVNL TPDKSQVLLQ NKESVLIALE NLMTTCYGPL PSTNSYENNK TDVSAADIVL  360

SKTAETDVLF NKVESSGKNY SNVDTSVIPF QNDMHNDESG KNTDDCLNHQ ISIGDFGYGH  420

CSSEISNIDK NTKNAFQDIS MSNVSWENSQ TEYSKTCFIS SVKHTQSENG NKDHIDESGE  480

NEEEAGLENS SEISADEWSR GNILKNSVGE NIEPVKILVP EKSLPCKVSN NNYPIPEQMN  540

LNEDSCNKKS NVIDNKSGKV TAYDLLSNRV IKKPMSASAL FVQDHRPQFL IENPKTSLED  600

ATLQIEELWK TLSEEEKLKY EEKATKDLER YNSQMKRAIE QESQMSLKDG RKKIKPTSAW  660

NLAQKHKLKT SLSNQPKLDE LLQSQIEKRR SQNIKMVQIP FSMKNLKINF KKQNKVDLEE  720

KDEPCLIHNL RFPDAWLMTS KTEVMLLNPY RVEEALLFKR LLENHKLPAE PLEKPIMLTE  780

SLFNGSHYLD VLYKMTADDQ RYSGSTYLSD PRLTANGFKI KLIPGVSITE NYLEIEGMAN  840

CLPFYGVADL KEILNAILNR NAKEVYECRP RKVISYLEGE AVRLSRQLPM YLSKEDIQDI  900

IYRMKHQFGN EIKECVHGRP FFHHLTYLPE TT                                932
```

Human PMS2 cDNA (SEQ ID NO: 7)

```
cgaggcggat cgggtgttgc atccatggag cgagctgaga gctcgagtac agaacctgct   60
aaggccatca aacctattga tcggaagtca gtccatcaga tttgctctgg gcaggtggta  120
ctgagtctaa gcactgcggt aaaggagtta gtagaaaaca gtctggatgc tggtgccact  180
aatattgatc taaagcttaa ggactatgga gtggatctta ttgaagtttc agacaatgga  240 tgtgggtag aagaagaaaa cttcgaaggc ttaactctga acatcacac atctaagatt  300 caagagtttg ccgacctaac tcaggttgaa acttttggct tcggggggga agctctgagc  360
tcactttgtg cactgagcga tgtcaccatt tctacctgcc acgcatcggc gaaggttgga  420
actcgactga tgtttgatca caatgggaaa attatccaga aaccccccta ccccgcccc  480 agagggacca cagtcagcgt gcagcagtta tttcccacac tacctgtgcg ccataaggaa  540
tttcaaagga atattaagaa ggagtatgcc aaaatggtcc aggtcttaca tgcatactgt  600
atcatttcag caggcatccg tgtaagttgc accaatcagc ttggacaagg aaaacgacag  660
cctgtggtac gcacaggtgg aagccccagc ataaaggaaa atatcggctc tgtgtttggg  720
cagaagcagt gcaaagcct cattcctttt gttcagctgc ccctagtga ctccgtgtgt  780 gaagagtacg gtttgagctg tcggatgct ctgcataatc tttttacat ctcaggtttc  840 atttcacaat gcacgcatgg agttggaagg agttcaacag acagacagtt tttcttatc  900 aaccggcggc cttgtgaccc agcaaggtc tgcagactcg tgaatgaggt ctaccacatg  960
tataatcgac accagtatcc atttgttgtt cttaacattt ctgttgattc agaatgcgtt 1020
gatatcaatg ttactccaga taaaaggcaa attttgctac aagaggaaaa gcttttgttg 1080
```

```
                                                      -continued
gcagttttaa agacctcttt gataggaatg tttgatagtg atgtcaacaa gctaaatgtc  1140
agtcagcagc cactgctgga tgttgaaggt aacttaataa aaatgcatgc agcggatttg  1200
gaaaagccca tggtagaaaa gcaggatcaa tccccttcat taaggactgg agaagaaaaa  1260
aaagacgtgt ccatttccag actgcgagag gccttttctc ttcgtcacac aacagagaac  1320
aagcctcaca gcccaaagac tccagaacca agaaggagcc ctctaggaca gaaaagggt   1380 atgctgtctt ctagcacttc aggtgccatc tctgacaaag gcgtcctgag acctcagaaa  1440
gaggcagtga gttccagtca cggacccagt gaccctacgg acagagcgga ggtggagaag  1500
gactcggggc acggcagcac ttccgtggat tctgagggt tcagcatccc agacacgggc   1560
agtcactgca gcagcgagta tgcggccagc tccccagggg cagggggctc gcaggaacat  1620
gtggactctc aggagaaagc gcctgaaact gacgactctt tttcagatgt ggactgccat  1680
tcaaaccagg aagataccgg atgtaaattt cgagttttgc ctcagccaac taatctcgca  1740
accccaaaca caaagcgttt taaaaaagaa gaaattcttt ccagttctga catttgtcaa  1800
aagttagtaa atactcagga catgtcagcc tctcaggttg atgtagctgt gaaaattaat  1860
aagaaagttg tgcccctgga ctttttctatg agttctttag ctaaacgaat aaagcagtta  1920
catcatgaag cacagcaaag tgaaggggaa cagaattaca ggaagtttag ggcaaagatt  1980
tgtcctggag aaaatcaagc agccgaagat gaactaagaa aagagataag taaaacgatg  2040
tttgcagaaa tggaaatcat tggtcagttt aacctgggat ttataataac caaactgaat  2100
gaggatatct tcatagtgga ccagcatgcc acggacgaga gtataacttc gagatgctg   2160 cagcagcaca ccgtgctcca ggggcagagg ctcatagcac ctcagactct caacttaact  2220
gctgttaatg aagctgttct gatagaaaat ctggaaatat ttagaagaa tggctttgat   2280 tttgttatcg atgaaaatgc tccagtcact gaaagggcta aactgatttc cttgccaact  2340
agtaaaaact ggaccttcgg accccaggac gtcgatgaac tgatcttcat gctgagcgac  2400
agccctgggg tcatgtgccg gccttcccga gtcaagcaga tgtttgcctc cagagcctgc  2460
cggaagtcgg tgatgattgg gactgctctt aacacaagcg agatgaagaa actgatcacc  2520 cacatgggg agatggacca ccctggaac tgtccccatg gaaggccaac catgagacac    2580
atcgccaacc tgggtgtcat ttctcagaac tgaccgtagt cactgtatgg aataattggt  2640
tttatcgcag attttttatgt tttgaaagac agagtcttca ctaaccttt ttgttttaaa   2700 atgaaacctg ctacttaaaa aaaatacaca tcacacccat ttaaaagtga tcttgagaac  2760
cttttcaaac c                                                      2771
``` human PMS1 protein (SEQ ID NO: 18)

```
MKQLPAATVR LLSSSQIITS VVSVVKELIE NSLDAGATSV DVKLENYGFD KIEVRDNGEG   60

IKAVDAPVMA MKYYTSKINS HEDLENLTTY GFRGEALGSI CCIAEVLITT RTAADNFSTQ  120

YVLDGSGHIL SQKPSHLGQG TTVTALRLFK NLPVRKQFYS TAKKCKDEIK KIQDLLMSFG  180

ILKPDLRIVF VHNKAVIWQK SRVSDHKMAL MSVLGTAVMN NMESFQYHSE ESQIYLSGFL  240

PKCDADHSFT SLSTPERSFI FTNSRPVHQK DILKLIRHHY NLKCLKESTR LYPVFFLKID  300

VPTADVDVNL TPDKSQVLLQ NKESVLIALE NLMTTCYGPL PSTNSYENNK TDVSAADIVL  360

SKTAETDVLF NKVESSGKNY SNVDTSVIPF QNDMHNDESG KNTDDCLNHQ ISIGDFGYGH  420

CSSEISNIDK NTKNAFQDIS MSNVSWENSQ TEYSKTCFIS SVKHTQSENG NKDHIDESGE  480

NEESAGLENS SEISADEWSR GNILKNSVGE NIEPVKILVP EKSLPCKVSN NNYPIPEQMN  540

LNEDSCNKKS NVIDNKSGKV TAYDLLSNRV IKKPMSASAL FVQDHRPQFL IENPKTSLED  600
```

-continued

```
ATLQIEELWK TLSEEEKLKY EEKATKDLER YNSQMKRAIE QESQMSLKDG RKKIKPTSAW   660
NLAQKHKLKT SLSNQPKLDE LLQSQIEKRR SQNIKMVQIP FSMKNLKINF KKQNKVDLEE   720
KDEPCLIHNL RFPDAWLMTS KTEVMLLNPY RVEEALLFKR LLENHKLPAE PLEKPIMLTE   780
SLFNGSHYLD VLYKMTADDQ RYSGSTYLSD PRLTANGFKI KLIPGVSITE NYLEIEGNAN   840
CLPFYGVADL KEILNAILNR NAKEVYECRP RKVISYLEGE AVRLSRQLPN YLSKEDIQDT   900
IYRMKHQFGN EIKECVHGRP FFHHLTYLPE TT                                932
```

Human PMS1 cDNA (SEQ ID NO: 8)

```
ggcacgagtg gctgcttgcg gctagtggat ggtaattgcc tgcctcgcgc tagcagcaag    60
ctgctctgtt aaaagcgaaa tgaaacaat tgcctgcggc aacaptccga ctccttttcaa  120
gttctcagat catcacttcg gtggtcagtg ttgtaaaaga gcttattgaa aactccttgg  180
atgctggtgc cacaagcgta gatgttaaac tggagaacta tggattgat aaaattgagg   240
tgcgagataa cggggagggt atcaaggctg ttgatgcacc tgtaatggca atgaagtact  300
acacctcaaa ataaatagt catgaagatc ttgaaaattt gacaacttac ggttttcgtg   360
gagaagcctt ggggtcaatt tgttgtatag ctgaggtttt aattacaaca gaacggctg   420
ctgataattt tagcacccag tatgttttag atggcagtgg ccacatactt tctcagaaac  480
cttcacatct tggtcaaggt acaactgtaa ctgctttaag attatttaag aatctacctg  540
taagaaagca gttttactca actgcaaaaa atgtaaaga tgaaataaaa aagatccaag   600
atctcctcat gagctttggt atccttaaac ctgacttaag gattgtcttt gtacataaca  660
aggcagttat ttgcagaaa agcagagtat cagatcacaa gatggctctc atgtcagttc  720
tggggactgc tgttatgaac aatatggaat cctttcagta ccactctgaa gaatctcaga  780
tttatctcag tggatttctt ccaaagtgtg atgcagacca ctctttcact agtctttcaa  840
caccagaaag aagtttcatc ttcataaaca gtcgaccagt acatcaaaaa gatatcttaa  900
agttaatccg acatcattac aatctgaaat gcctaaagga atctactcgt ttgtatcctg  960
tttttttttct gaaaatcgat gttcctacag ctgatgttga tgtaaattta acaccagata 1020
aaagccaagt attattacaa ataaggaat ctgttttaat tgctcttgaa atctgatga   1080
cgacttgtta tggaccatta cctagtacaa attcttatga aaataataaa acagatgttt  1140
ccgcagctga catcgttctt agtaaaacag cagaaacaga tgtgcttttt aataaagtgg  1200
aatcatctgg aaagaattat tcaaatgttg atacttcagt cattccattc caaaatgata  1260
tgcataatga tgaatctgga aaaaacactg atgattgttt aaatcaccag ataagtattg  1320
gtgactttgg ttatggtcat tgtagtagtg aaatttctaa cattgataaa aacactaaga  1380
atgcatttca ggacatttca atgagtaatg tatcatggga gaactctcag acggaatata  1440
gtaaaacttg ttttataagt tccgttaagc acacccagtc agaaaatggc aataaagacc  1500
atatagatga gagtgggaa atgaggaag aagcaggtct tgaaaactct tcggaaattt   1560
ctgcagatga gtggagcagg ggaaatatac ttaaaaattc agtgggagag atattgaac   1620
ctgtgaaaat tttagtgcct gaaaaaagtt taccatgtaa agtaagtaat aataattatc  1680
caatccctga acaaatgaat cttaatgaag attcatgtaa caaaaaatca aatgtaatag  1740
ataataaatc tggaaaagtt acagcttatg atttacttag caatcgagta atcaagaaac  1800
ccatgtcagc aagtgctctt tttgttcaag atcatcgtcc tcagtttctc atagaaaatc  1860
ctaagactag tttagaggat gcaacactac aaattgaaga actgtggaag acattgagtg  1920
aagaggaaaa actgaaatat gaagagaagg ctactaaaga cttggaacga tacaatagtc  1980
```

-continued

```
aaatgaagag agccattgaa caggagtcac aaatgtcact aaaagatggc agaaaaaaga   2040
taaaacccac cagcgcatgg aatttggccc agaagcacaa gttaaaaacc tcattatcta   2100
atcaaccaaa acttgatgaa ctccttcagt cccaaattga aaaagaagg agtcaaaata    2160 ttaaaatggt acagatcccc ttttctatga aaaacttaaa aataaatttt aagaaacaaa   2220
acaaagttga cttagaagag aaggatgaac cttgcttgat ccacaatctc aggtttcctg   2280
atgcatggct aatgacatcc aaaacagagg taatgttatt aaatccatat agagtagaag   2340
aagccctgct atttaaaaga cttcttgaga atcataaact tcctgcagag ccactggaaa   2400
agccaattat gttaacagag agtctttttta tggatctca ttatttagac gttttatata    2460
aaatgacagc agatgaccaa agatacagtg gatcaactta cctgtctgat cctcgtctta   2520
cagcgaatgg tttcaagata aaattgatac caggagtttc aattactgaa aattacttgg   2580
aaatagaagg aatggctaat tgtctcccat tctatggagt agcagattta aaagaaattc   2640
ttaatgctat attaaacaga aatgcaaagg aagtttatga atgtagacct cgcaaagtga   2700
taagttattt agagggagaa gcagtgcgtc tatccagaca attacccatg tacttatcaa   2760
aagaggacat ccaagacatt atctacagaa tgaagcacca gtttggaaat gaaattaaag   2820
agtgtgttca tggtcgccca ttttttcatc atttaaccta tcttccagaa actacatgat   2880
taaatatgtt taagaagatt agttaccatt gaaattggtt ctgtcataaa acagcatgag   2940 tctggttttta aattatcttt gtattatgtg tcacatggtt atttttaaa tgaggattca   3000 ctgacttgtt tttatattga aaaagttcc acgtattgta gaaaacgtaa ataaactaat    3060
aac                                                                3063
``` human MSH2 protein (SEQ ID NO: 19)

```
NAVQPKETLQ LESAAEVGFV RFFQGMPEKP TTTVRLFDRG DFYTAHDEDA LLAAREVFKT    60

QGVIKYMGPA GAKNLQSVVL SKMNFESFVK DLLLVRQYRV EVYKNRAGNK ASKENDWYLA   120

YKASPGNLSQ FEDILFGNND MSASIGVVGV KMSAVDGQRQ VGVGYVDSIQ RKLGLCEFPD   180

NDQFSNLEAL LIQIGPKECV LPGGETAGDM GKLRQIIQRG GILITERKKA DFSTKDIYQD   240

LNRLLKGKKG EQMNSAVLPE MENQVAVSSL SAVIKFLELL SDDSNFGQFE LTTFDFSQYM   300

KLDIAAVRAL NLFQGSVEDT TGSQSLAALL NKCKTPQGQR LVNQWIKQPL MDKNRIEERL   360

NLVEAFVEDA ELRQTLQEDL LRRFPDLNRL AKKFQRQAAN LQDCYRLYQG INQLPNVIQA   420

LEKHEGKHQK LLLAVFVTPL TDLRSDFSKF QEMIETTLDM DQVENHEFLV KPSFDPNLSE   480

LREIMNDLEK KMQSTLISAA RDLGLDPGKQ IKLDSSAQFG YYFRVTCKEE KVLRNNKNFS   540

TVDIQKNGVK FTNSKLTSLN EEYTKNKTEY EEAQDAIVKE IVNISSGYVE PMQTLNDVLA   600

QLDAVVSFAH VSNGAPVPYV RPAILEKGQG RIILKASRHA CVEVQDEIAF IPNDVYFEKD   660

KQMFHIITGP NMGGKSTYIR QTGVIVLMAQ IGCFVPCESA EVSIVDCILA RVGAGDSQLK   720

GVSTFMAEML ETASILRSAT KDSLIIIDEL GRGTSTYDGF GLAWAISEYI ATKIGAFCMF   780

ATHFHELTAL ANQIPTVNNL HVTALTTEET LTMLYQVKKG VCDQSEGIHV AELANFPKHV   840

IECAKQKALE LEEFQYIGES QGYDIMEPAA KKCYLEREQG EKIIQEFLSK VKQMPFTEMS   900

EENITIKLKQ LKAEVIAKNN SFVNEIISRI KVTT                               934
```

Human MSH2 cDNA (SEQ ID NO: 9)

```
ggcgggaaac agcttagtgg gtgtggggtc gcgcattttc ttcaaccagg aggtgaggag    60
gtttcgacat ggcggtgcag ccgaaggaga cgctgcagtt ggagagcgcg gccgaggtcg   120
gcttcgtgcg cttctttcag ggcatgccgg agaagccgac caccacagtg cgccttttcg   180
```

-continued

```
accgggcga cttctatacg gcgcacggcg aggacgcgct gctggccgcc cgggaggtgt    240
tcaagaccca gggggtgatc aagtacatgg ggccggcagg agcaaagaat ctgcagagtg   300
ttgtgcttag taaaatgaat tttgaatctt ttgtaaaaga tcttcttctg gttcgtcagt   360
atagagttga agtttataag aatagagctg gaaataaggc atccaaggag aatgattggt   420
atttggcata taaggcttct cctggcaatc tctctcagtt tgaagacatt ctctttggta   480
acaatgatat gtcagcttcc attggtgttg tgggtgttaa aatgtccgca gttgatggcc   540
agagacaggt tggagttggg tatgtggatt ccatacagag gaaactagga ctgtgtgaat   600
tccctgataa tgatcagttc tccaatcttg aggctctcct catccagatt ggaccaaagg   660
aatgtgtttt acccggagga gagactgctg gagacatggg gaaactgaga cagataattc   720
aaagaggagg aattctgatc acagaaagaa aaaagctga cttttccaca aaagacattt   780
atcaggacct caaccggttg ttgaaaggca aaagggaga gcagatgaat agtgctgtat   840
tgccagaaat ggagaatcag gttgcagttt catcactgtc tgcggtaatc aagtttttag   900
aactcttatc agatgattcc aactttggac agtttgaact gactactttt gacttcagcc   960
agtatatgaa attggatatt gcagcagtca gagcccttaa ccttttttcag ggttctgttg  1020 aagataccac tggctctcag tctctggctg ccttgctgaa taagtgtaaa accctcaag   1080 gacaaagact tgttaaccag tggattaagc agcctctcat ggataagaac agaatagagg  1140
agagattgaa tttagtggaa gcttttgtag aagatgcaga attgaggcag actttacaag  1200
aagatttact tcgtcgattc ccagatctta accgacttgc caagaagttt caaagacaag  1260
cagcaaactt acaagattgt taccgactct atcagggtat aaatcaacta cctaatgtta  1320
tacaggctct ggaaaaacat gaaggaaaac accagaaatt attgttggca gttttttgtga 1380 ctcctcttac tgatcttcgt tctgacttct ccaagtttca ggaaatgata gaaacaactt  1440
tagatatgga tcaggtggaa aaccatgaat tccttgtaaa accttcattt gatcctaatc  1500
tcagtgaatt aagagaaata atgaatgact tggaaaagaa gatgcagtca acattaataa  1560
gtgcagccag agatcttggc ttggaccctg gcaaacagat taaactggat tccagtgcac  1620
agtttggata ttactttcgt gtaacctgta aggaagaaaa agtccttcgt aacaataaaa  1680
actttagtac tgtagatatc cagaagaatg gtgttaaatt taccaacagc aaattgactt  1740
cttaaaatga agagtatacc aaaaataaaa cagaatatga agaagcccag gatgccattg  1800
ttaaagaaat tgtcaatatt tcttcaggct atgtagaacc aatgcagaca ctcaatgatg  1860
tgttagctca gctagatgct gttgtcagct ttgctcacgt gtcaaatgga gcacctgttc  1920
catatgtacg accagccatt ttggagaaag gacaaggaag aattatatta aaagcatcca  1980
ggcatgcttg tgttgaagtt caagatgaaa ttgcatttat tcctaatgac gtatactttg  2040
aaaaagataa acagatgttc cacatcatta ctggccccaa tatgggaggt aaatcaacat  2100
atattcgaca aactggggtg atagtactca tggcccaaat tgggtgtttt gtgccatgtg  2160
agtcagcaga agtgtccatt gtggactgca tcttagcccg agtagggcct ggtgacagtc  2220
aattgaaagg agtctccacg ttcatggctg aaatgttgga aactgcttct atcctcaggt  2280
ctgcaaccaa agattcatta ataatcatag atgaattggg aagaggaact tctacctacg  2340
atggatttgg gttagcatgg gctatatcag aatacattgc aacaaagatt ggtgcttttt  2400
gcatgtttgc aacccatttt catgaactta ctgccttggc caatcagata ccaactgtta  2460
ataatctaca tgtcacagca ctcaccactg aagagacctt aactatgctt tatcaggtga  2520
agaaaggtgt ctgtgatcaa agttttggga ttcatgttgc agagcttgct aatttcccta  2580
```

-continued

```
agcatgtaat agagtgtgct aaacagaaag ccctggaact tgaggagttt cagtatattg   2640
gagaatcgca aggatatgat atcatggaac cagcagcaaa gaagtgctat ctggaaagag   2700
agcaaggtga aaaaattatt caggagttcc tgtccaaggt gaaacaaatg ccctttactg   2760
aaatgtcaga agaaaacatc acaataaagt taaaacagct aaaagctgaa gtaatagcaa   2820
agaataatag ctttgtaaat gaaatcattt cacgaataaa agttactacg tgaaaaatcc   2880
cagtaatgga atgaaggtaa tattgataag ctattgtctg taatagtttt atattgtttt   2940
atattaaccc tttttccata gtgttaactg tcagtgccca tgggctatca acttaataag   3000
atatttagta atattttact ttgaggacat tttcaaagat ttttattttg aaaaatgaga   3060
gctgtaactg aggactgttt gcaattgaca taggcaataa taagtgatgt gctgaatttt   3120
ataaataaaa tcatgtagtt tgtgg                                         3145
``` human MLH1 protein (SEQ ID NO: 20)

```
MSFVAGVIRR LDETVVNRIA AGEVIQRPAN AIKEMIENCL DAKSTSIQVI VKEGGLKLIQ    60

IQDNGTGIRK EDLDIVCERF TTSKLQSFED LASISTYGFR GEALASISHV AHVTITTKTA   120

DGKCAYRASY SDGKLKAPPK PCAGNQGTQI TVEDLFYNIA TRRKALKNPS EEYGKILEVV   180

GRYSVHNAGI SFSVKKQGET VADVRTLDNA STVDNIRSIF GNAVSRELIE IGCEDKTLAF   240

KMNGYISNAN YSVKKCIFLL FINHRLVEST SLRKAIETVY AAYLPKNTHP FLYLSLEISP   300

QNVDVNVHPT KHEVHFLHEE SILERVQQHI ESKLLGSNSS RMYFTQTLLP GLAGPSGEMV   360

KSTTSLTSSS TSGSSDKVYA NQMVRTDSRE QKLDAFLQPL SKPLSSQPQA IVTEDKTDIS   420

SGRARQQDEE MLELPAPAEV AAKNQSLEGD TTKGTSEMSE KRGPTSSNPR KRHREDSDVE   480

MVEDDSRKEM TAACTPRRRI INLTSVLSLQ EEINEQGHEV LREMLHNHSF VGCVNPQWAL   540

AQHQTKLYLL NTTKLSEELF YQILIYDFAN FGVLRLSEPA PLFDLAMLAL DSPESGWTEE   600

DGPKEGLAEY IVEFLKKKAE MLADYFSLEI DEEGNLIGLP LLIDNYVPPL EGLPIFTLRL   660

ATEVNWDEEK ECFESLSKEC AMFYSIRKQY ISEESTLSGQ QSEVPGSIPN SWKWTVEHIV   720

YKALRSHILP PKHFTEDGNI LQLANLPDLY KVFERC                            756
```

Human MLH1 cDNA (SEQ ID NO: 10)

```
cttggctctt ctggcgccaa aatgtcgttc gtggcagggg ttattcggcg gctggacgag    60
acagtggtga accgcatcgc ggcgggggaa gttatccagc ggccagctaa tgctatcaaa   120
gagatgattg agaactgttt agatgcaaaa tccacaagta ttcaagtgat tgttaaagag   180
ggaggcctga gttgattca gatccaagac aatggcaccg ggatcaggaa agaagatctg   240
gatattgtat gtgaaaggtt cactactagt aaactgcagt cctttgagga tttagccagt   300
atttctacct atggctttcg aggtgaggct ttggccagca taagccatgt ggctcatgtt   360
actattacaa cgaaaacagc tgatggaaag tgtgcataca gagcaagtta ctcagatgga   420
aaactgaaag cccctcctaa accatgtgct ggcaatcaag ggacccagat cacggtggag   480
gacctttttt acaacatagc cacgaggaga aaagctttaa aaaatccaag tgaagaatat   540
gggaaaattt tggaagttgt tggcaggtat tcagtacaca atgtaggcat tagtttctca   600
gttaaaaaac aaggagagac agtagctgat gttaggacac acccaatgc ctcaaccgtg   660 gacaatattc gctccatctt tggaaatgct gttagtcgag aactgataga aattggatgt   720
gaggataaaa ccctagcctt caaatgaat ggttacatat ccaatgcaaa ctactcagtg   780
aagaagtgca tcttcttact cttcatcaac catcgtctgg tagaatcaac ttccttgaga   840
aaagccatag aaacagtgta tgcagcctat ttgcccaaaa acacacaccc attcctgtac   900
```

-continued

```
ctcagtttag aaatcagtcc ccagaatgtg gatgttaatg tgcaccccac aaagcatgaa    960
gttcacttcc tgcacgagga gagcatcctg gagcgggtgc agcagcacat cgagagcaag   1020
ctcctgggct ccaattcctc caggatgtac ttcacccaga ctttgctacc aggacttgct   1080
ggcccctctg gggagatggt taaatccaca acaagtctga cctcgtcttc tacttctgga   1140
agtagtgata aggtctatgc ccaccagatg gttcgtacag attcccggga acagaagctt   1200
gatgcatttc tgcagcctct gagcaaaccc ctgtccagtc agccccaggc cattgtcaca   1260
gaggataaga cagatatttc tagtggcagg gctaggcagc aagatgagga gatgcttgaa   1320
ctcccagccc ctgctgaagt ggctgccaaa atcagagct tggaggggga tacaacaaag   1380
gggacttcag aaatgtcaga agagagga cctacttcca gcaaccccag aaagagacat   1440
cgggaagatt ctgatgtgga aatggtggaa gatgattccc gaaaggaaat gactgcagct   1500 tgtaccccc ggagaaggat cattaacctc actagtgttt tgagtctcca ggaagaaatt   1560
aatgagcagg gacatgaggt tctccgggag atgttgcata accactcctt cgtgggctgt   1620
gtgaatcctc agtgggcctt ggcacagcat caaaccaagt tataccttct caacaccacc   1680
aagcttagtg aagaactgtt ctaccagata ctcatttatg attttgccaa ttttggtgtt   1740
ctcaggttat cggagccagc accgctcttt gaccttgcca tgcttgcctt agatagtcca   1800
gagagtggct ggacagagga agatggtccc aaagaaggac ttgctgaata cattgttgag   1860
tttctgaaga gaaggctga gatgcttgca gactatttct ctttggaaat tgatgaggaa   1920
gggaacctga ttggattacc ccttctgatt gacaactatg tgcccccttt ggagggactg   1980
cctatcttca ttcttcgact agccactgag gtgaattggg acgaagaaaa ggaatgtttt   2040
gaaagcctca gtaaagaatg cgctatgttc tattccatcc ggaagcagta catatctgag   2100
gagtcgaccc tctcaggcca gcagagtgaa gtgcctggct ccattccaaa ctcctggaag   2160
tggactgtgg aacacattgt ctataaagcc ttgcgctcac acattctgcc tcctaaacat   2220
ttcacagaag atggaaatat cctgcagctt gctaacctgc ctgatctata caaagtcttt   2280
gagaggtgtt aaatatggtt atttatgcac tgtgggatgt gttcttcttt ctctgtattc   2340
cgatacaaag tgttgtatca aagtgtgata tacaaagtgt accaacataa gtgttggtag   2400
cacttaagac ttatacttgc cttctgatag tattcccttta tacacagtgg attgattata   2460
aataaataga tgtgtcttaa cata                                          2484
``` hPMS2-134 protein (SEQ ID NO: 21)

```
MKQLPAATVR LLSSSQIITS VVSVVKELIE NSLDAGATSV DVKLENYGFD KIEVRDNGEG    60

IKAVDAPVMA MKYYTSKINS HEDLENLTTY GFRGEALGSI CCIAEVLITT RTAADNFSTQ   120

YVLDGSGHIL SQK                                                     133
``` hPMS2-134 cDNA (SEQ ID NO: 11)

```
cgaggcggat cgggtgttgc atccatggag cgagctgaga gctcgagtac agaacctgct    60
aaggccatca aacctattga tcggaagtca gtccatcaga tttgctctgg gcaggtggta   120
ctgagtctaa gcactgcggt aaaggagtta gtagaaaaca gtctggatgc tggtgccact   180
aatattgatc taaagcttaa ggactatgga gtggatctta ttgaagtttc agacaatgga   240 tgtgggggtag aagaagaaaa cttcgaaggc ttaactctga acatcacac atctaagatt   300 caagagtttg ccgacctaac tcaggttgaa acttttggct tcgggggga agctctgagc   360 tcactttgtg cactgagcga tgtcaccatt tctacctgcc acgcatcggc gaaggttgga   420
acttga                                                              426
``` hMSH6 (human cDNA) ACCESSION U28946 (SEQ ID NO: 22)

MSRQSTLYSFFPKSPALSDANKASARASREGGRAAAAPGASPSP
GGDAAWSEAGPGPRPLARSASPPKAKNLNGGLRRSVAPAAPTSCDFSPGDLVWAKMEG
YPWWPCLVYNHPFDGTFIREKGKSVRVHVQFFDDSPTRGWVSKRLLKPYTGSKSKEAQ
KGGHFYSAKPEILRAMQRADEALNKDKIKRLELAVCDEPSEPEEEEMEVGTTYVTDK
SEEDNEIESEEEVQPKTQGSRRSSRQIKKRRVISDSESDIGGSDVEFKPDTKEEGSSD
EISSGVGDSESEGLNSPVKVARKRKRMVTGNGSLRKSSRKETPSATKQATSISSETK
NTLRAFSAPQNSESQAHVSGGGDDSSRPTVWYHETLEWLKEEKRRDEHRRRPDHPDFD
ASTLYVPEDFLNSCTPGMRKWWQIKSQNFDLVICYKVGKFYELYHNDALIGVSELGLV
FMKGNWAHSGFPEIAFGRYSDSLVQKGYKVARVEQTETPEMMEARCRKMAHISKYDRV
VRREICRIITKGTQTYSVLEGDPSENYSKYLLSLEKKEEDSSGHTRAYGVCFVDTSLG
KFFIGQFSDDRNCSRFRTLVAHYPPVQVLFEKGNLSKETKTILKSSLSCSLQEGLIPG
SQFWDASKTLRTLLEEEYFREKLSDGIGVMLPQVLKGMTSESDSIGLTPGEKSELALS
ALGGCVFYLKKCLIDQELLSMANFEEYIPLDSDTVSTTRSGAIFTKAYQRMVLDAVTL
NNLEIFLNGTNGSTEGTLLERVDTCHTPFGKRLLKQWLCAPLCNHYAINDRLDAIEDL
MVVPDKISEVVELLKKLPDLERLLSKIHNVGSPLKSQNHPDSRAIMYEETTYSKKKII
DFLSALEGFKVMCKIIGIMEEVADGFKSKILKQVISLQTKNPEGRFPDLTVELNRWDT
AFDHEKARKTGLITPKAGFDSDYDQALADIRENEQSLLEYLEKQRNRIGCRTIVYWGI
GRNRYQLEIPENFTTRNLPEEYELKSTKKGCKRYWTKTIEKKLANLTNAEERRDVSLK
DCMRRLEYNFDKNYKDWQSAVECIAVLDVLLCLANYSRGGDGPMCRPVILLPEDTPPF
LELKGSRHPCITKTFFGDDFIPNDILIGCEEEEQENGKAYCVLVTGPNMGGKSTLMRQ
AGLLAVMAQMGCYVPAEVCRLTPIDRVFTRLGASDRIMSGESTFFVELSETASILMHA
TAHSLVLVDELGRGTATFDGTAIANAVVKELAETIKCRTLFSTHYHSLVEDYSQNVAV
RLGHMACMVENECEDPSQETITFLYKFIKGACPKSYGFNAARLANLPEEVIQKGHRKA
REFEKMNQSLRLFREVCLASERSTVDAEAVHKLLTLIKEL"

hPMSR2 (human cDNA) ACCESSION U38964 (SEQ ID NO: 12)

```
1    ggcgctccta cctgcaagtg ctagtgcca agtgctgggc cgccgctcct gccgtgcatg
61   ttggggagcc agtacatgca ggtgggctcc acacggagag gggcgcagac ccggtgacag
121  ggctttacct ggtacatcgg catggcgcaa ccaaagcaag agagggtggc gcgtgccaga
181  caccaacggt cggaaaccgc cagacaccaa cggtcggaaa ccgccaagac accaacgctc
241  ggaaaccgcc agacaccaac gctcggaaac cgccagacac caaggctcgg aatccacgcc
301  aggccacgac ggagggcgac tacctcccct ctgaccctgc tgctggcgtt cggaaaaaac
361  gcagtccggt gtgctctgat tggtccaggc tctttgacgt cacggactcg acctttgaca
421  gagccactag gcgaaaagga gagacgggaa gtattttttc cgccccgccc ggaaagggtg
481  gagcacaacg tcgaaagcag ccgttgggag cccaggaggc ggggcgcctg tgggagccgt
541  ggagggaact ttcccagtcc ccgaggcgga tccggtgttg catccttgga gcgagctgag
601  aactcgagta cagaacctgc taaggccatc aaacctattg atcggaagtc agtccatcag
661  atttgctctg ggccggtggt accgagtcta aggccgaatg cggtgaagga gttagtagaa
721  aacagtctgg atgctggtgc cactaatgtt gatctaaagc ttaaggacta tggagtggat
781  ctcattgaag tttcaggcaa tggatgtggg gtagaagaag aaaacttcga aggctttact
```

-continued

```
 841 ctgaaacatc acacatgtaa gattcaagag tttgccgacc taactcaggt ggaaactttt
 901 ggctttcggg gggaagctct gagctcactt tgtgcactga gtgatgtcac catttctacc
 961 tgccgtgtat cagcgaaggt tgggactcga ctggtgtttg atcactatgg gaaaatcatc
1021 cagaaaaccc cctaccccg ccccagaggg atgacagtca gcgtgaagca gttattttct
1081 acgctacctg tgcaccataa agaatttcaa aggaatatta agaagaaacg tgcctgcttc
1141 cccttcgcct tctgccgtga ttgtcagttt cctgaggcct ccccagccat gcttcctgta
1201 cagcctgtag aactgactcc tagaagtacc ccaccccacc cctgctcctt ggaggacaac
1261 gtgatcactg tattcagctc tgtcaagaat ggtccaggtt cttctagatg atctgcacaa
1321 atggttcctc tcctccttcc tgatgtctgc cattagcatt ggaataaagt tcctgctgaa
1381 aatccaaaaa aaaaaaaaaa aaaaaaaa
``` hPMSR2 (human protein) ACCESSION U38964 (SEQ ID NO: 23)

MAQPKQERVARARHQRSETARHQRSETAKTPTLGNRQTPTLGNR
QTPRLGIHARPRRRATTSLLTLLLAFGKNAVRCALIGPGSLTSRTRPLTEPLGEKERR
EVFFPPRPERVEHNVESSRWEPRRRGACGSRGGNFPSPRGGSGVASLERAENSSTEPA
KAIKPIDRKSVHQICSGPVVPSLRPNAVKELVENSLDAGATNVDLKLKDYGVDLIEVS
GNGCGVEEENFEGFTLKHHTCKIQEFADLTQVETFGFRGEALSSLCALSDVTISTCRV
SAKVGTRLVFDHYGKIIQKTPYPRPRGMTVSVKQLFSTLPVHHKEFQRNIKKKRACFP
FAFCRDCQFPEASPAMLPVQPVELTPRSTPPHPCSLEDNVITVFSSVKNGPGSSR

HPMSR3 (human cDNA) ACCESSION U38979 (SEQ ID NO: 13)

```
   1 tttttagaaa ctgatgttta ttttccatca accatttttc catgctgctt aagagaatat
  61 gcaagaacag cttaagacca gtcagtggtt gctcctaccc attcagtggc ctgagcagtg
 121 gggagctgca gaccagtctt ccgtggcagg ctgagcgctc cagtcttcag tagggaattg
 181 ctgaataggc acagagggca cctgtacacc ttcagaccag tctgcaacct caggctgagt
 241 agcagtgaac tcaggagcgg gagcagtcca ttcaccctga aattcctcct tggtcactgc
 301 cttctcagca gcagcctgct cttcttttc aatctcttca ggatctctgt agaagtacag
 361 atcaggcatg acctcccatg ggtgttcacg ggaaatggtg ccacgcatgc gcagaacttc
 421 ccgagccagc atccaccaca ttaaacccac tgagtgagct cccttgttgt tgcatgggat
 481 ggcaatgtcc acatagcgca gaggagaatc tgtgttacac agcgcaatgg taggtaggtt
 541 aacataagat gcctccgtga gaggcgaagg gcggcgggga cccgggcctg gcccgtatgt
 601 gtccttggcg gcctagacta ggccgtcgct gtatggtgag ccccagggag gcggatctgg
 661 gcccccagaa ggacacccgc ctggatttgc ccgtagccc ggcccgggcc ctcgggagc
 721 agaacagcct tggtgaggtg acaggagggg acctcgcga gcagacgcgc gcgccagcga
 781 cagcagcccc gccccggcct ctcgggagcc gggggggcaga ggctgcggag ccccaggagg
 841 gtctatcagc cacagtctct gcatgtttcc aagagcaaca ggaaatgaac acattgcagg
 901 ggccagtgtc attcaaagat gtggctgtgg atttcaccca ggaggagtgg cggcaactgg
 961 accctgatga agatagca tacggggatg tgatgttgga gaactacagc catctagttt
1021 ctgtggggta tgattatcac caagccaaac atcatcatgg agtggaggtg aaggaagtgg
1081 agcagggaga ggagccgtgg ataatggaag gtgaatttcc atgtcaacat agtccagaac
1141 ctgctaaggc catcaaacct attgatcgga agtcagtcca tcagatttgc tctgggccag
1201 tggtactgag tctaagcact gcagtgaagg agttagtaga aacagtctg gatgctggtg
```

-continued

```
1261 ccactaatat tgatctaaag cttaaggact atggagtgga tctcattgaa gtttcagaca
1321 atggatgtgg ggtagaagaa gaaaactttg aaggcttaat ctctttcagc tctgaaacat
1381 cacacatgta agattcaaga gtttgccgac ctaactgaag ttgaaacttt cggttttcag
1441 ggggaagctc tgagctcact gtgtgcactg agcgatgtca ccatttctac ctgccacgcg
1501 ttggtgaagg ttgggactcg actggtgttt gatcacgatg ggaaaatcat ccaggaaacc
1561 ccctacccccc accccagagg gaccacagtc agcgtgaagc agttattttc tacgctacct
1621 gtgcgccata aggaatttca aggaatatt aagaagacgt gcctgcttcc ccttcgcctt
1681 ctgccgtgat tgtcagtttc ctgaggcctc cccagccatg cttcctgtac agcctgcaga
1741 actgtgagtc aattaaacct cttttcttca taaattaaaa aaaaa
``` hPMSR3 (human protein) ACCESSION U38979 (SEQ ID NO: 24)

MCPWRPRLGRRCMVSPREADLGPQKDTRLDLPRSPARAPREQNS

LGEVDRRGPREQTRAPATAAPDRPLGSRGAEAAEPQEGLSATVSACFQEQQENNTLQG

PVSFKDVAVDFTQEEWRQLDPDSKIAYGDVMLENYSHLVSVGYDYHQAKHHHGVEVKE

VEQGEEPWIMEGEFPCQHSPEPAKAIKPIDRKSVHQICSGPVVLSLSTAVKELVENSL

DAGATNIDLKLKDYGVDLIEVSDNGCGVEEENFEGLISFSSETSHM"

hPMSL9 (human cDNA) ACCESSION NM_005395 (SEQ ID NO: 14)

```
  1 atgtgtcctt ggcggcctag actaggccgt cgctgtatgg tgagccccag ggaggcggat
 61 ctgggccccc agaaggacac ccgcctggat ttgccccgta gcccggcccg ggcccctcgg
121 gagcagaaca gccttggtga ggtggacagg aggggacctc gcgagcagac gcgcgcgcca
181 gcgacagcag ccccgccccg gcctctcggg agccgggggg cagaggctgc ggagccccag
241 gagggtctat cagccacagt ctctgcatgt ttccaagagc aacaggaaat gaacacattg
301 cagggggcca gtgtcattca agatgtggct gtggatttca cccaggagga gtggcggcaa
361 ctggaccctg atgagaagat agcatacggg gatgtgatgt tggagaacta cagccatcta
421 gtttctgtgg ggtatgatta tcaccaagcc aaacatcatc atggagtgga ggtgaaggaa
481 gtggagcagg gagaggagcc gtggataatg gaaggtgaat tccatgtca acatagtcca
541 gaacctgcta aggccatcaa acctattgat cggaagtcag tccatcagat ttgctctggg
601 ccagtggtac tgagtctaag cactgcagtg aaggagttag tagaaaacag tctggatgct
661 ggtgccacta atattgatct aaagcttaag gactatggag tggatctcat tgaagtttca
721 gacaatggat gtgggtaga agaagaaaac tttgaaggct taatctcttt cagctctgaa
781 acatcacaca tgtaa
``` hPMSL (human protein) ACCESSION NM_005395 (SEQ ID NO: 25)

MCPWRPRLGRRCMVSPREADLGPQKDTRLDLPRSPARAPREQNS

LGEVDRRGPREQTRAPATAAPPRPLGSRGAEAAEPQEGLSATVSACFQEQQEMNTLQG

PVSFKDVAVDFTQEEWRQLDPDEKIAYGDVMLENYSHLVSVGYDYHQAKHHHGVEVKE

VEQGEEPWIMEGEFPCQHSPEPAKAINPIDRKSVHQICSGPVVLSLSTAVKELVENSL

DAGATNIDLKLKDYGVDLIEVSDNGCGVEEENFEGLISFSSETSHM"

REFERENCES

1. Attfield, P. V. and Pinney, R. J. 985. Elimination of multicopy plasmid R6K by bleomycin. Antimicrob. Agents Chemother. 27(6):985–988.
2. Baker S. M., Bronner, C. E., Zhang, L., Plug, A. W., Robatez, M., Warren, G., Elliott, E. A., Yu, J., Ashley, T., Arnheim, N., Bradley, N., Flavell, R. A., and Liskay, R. M. 1995. Male defective in the DNA mismatch repair gene PMS2 exhibit abnormal chromosome synapsis in meiosis. Cell 82:309–319.
3. Berry, A. 1996. Improving production of aromatic compounds in *Escherichia coli* by metabolic engineering. Trends Biotechnol. 14(7):250–256.
4. Bronner, C. E., Baker, S. M., Morrison, P. T., Warren, G., Smith, L. G., Lescoe, M. K., Kane, M., Earabino, C., Lipford, J., Lindblom, A., Tannergard, P., Bollag, R. J., Godwin, A., R., Ward, D. C., Nordenskjold, M., Fishel, R., Kolodner, R., and Liskay, R. M. 1994. Mutation in the DNA mismatch repair gene homologue hMLH1 is associated with hereditary non-polyposis colon cancer. Nature 368:258–261.
5. de Wind N., Dekker, M., Berns, A., Radman, M., and Riele, H. T. 1995. Inactivation of the mouse Msh2 gene results in mismatch repair deficiency, methylation tolerance, hyperrecombination, and predisposition to cancer. Cell 82:321–300.
6. Drummond, J. T., Li, G. M., Longley, M. J., and Modrich, P. 1995. Isolation of an hMSH2-p160 heterodimer that restores mismatch repair to tumor cells. Science 268: 1909–1912.
7. Drummond, J. T., Anthoney, A., Brown, R., and Modrich, P. 1996. Cisplatin and adriamycin resistance are associated with MutLa and mismatch repair deficiency in an ovarian tumor cell line. J. Biol. Chem. 271:9645–19648.
8. Edelmann, W., Cohen, P. E., Kane, M., Lau, K., Morrow, B., Bennett, S., Umar, A., Kunkel, T., Cattoretti, G., Chagnatti, R., Pollard, J. W., Kolodner, R. D., and Kucherlapati, R. 1996. Meiotic pachytene arrest in MLH1-deficient mice. Cell 85:1125–1134.
9. Fishel, R., Lescoe, M., Rao, M. R. S., Copeland, N. J., Jenkins, N. A., Garber, J., Kane, M., and Kolodner, R. 1993. The human mutator gene homolog MSH2 and its association with hereditary nonpolyposis colon cancer. Cell 7:1027–1038.
10. Fu, K. P., Grace, M. E., Hsiao, C. L., and Hung, P. P. 1988. Elimination of antibiotic-resistant plasmids by quinolone antibiotics. Chemotherapy 34(5):415–418.
11. Leach, F. S., Nicolaides, N. C, Papadopoulos, N., Liu, B., Jen, J., Parsons, R., Peltomaki, P., Sistonen, P., Aaltonen, L. A., Nystrom-Lahti, M., Guan, X. Y., Zhang, J., Meltzer, P. S., Yu, J. W., Kao, F. T., Chen, D. J., Cerosaletti, K. M., Fournier, R. E. K., Todd, S., Lewis, T., Leach R. J., Naylor, S. L., Weissenbach, J., Mecklin, J. P., Jarvinen, J. A., Petersen, G. M., Hamilton, S. R., Green, J., Jass, J., Watson, P., Lynch, H. T., Trent, J. M., de la Chapelle, A., Kinzler, K. W., and Vogelstein, B. 1993. Mutations of a mutS homolog in hereditary non-polyposis colorectal cancer. Cell 75:1215–1225.
12. Li, G.-M., and Modrich, P. 1995. Restoration of mismatch repair to nuclear extracts of H6 colorectal tumor cells by a heterodimer of human mutL homologs. Proc. Natl. Acad. Sci. USA 92:1950–1954.
13. Liu, B., Parsons, R., Papadopoulos, N., Nicolaides, N. C., Lynch, H. T., Watson, P., Jass, J. R., Dunlop, M., Wyllie, A., Peltomaki, P., de la Chapelle, A., Hamilton, S. R., Vogelstein, B., and Kinzler, K. W. 1996. Analysis of mismatch repair genes in hereditary non-polyposis colorectal cancer patients. Nat. Med. 2:169–174.
14. Modrich, P. 1994. Mismatch repair, genetic stability, and cancer. Science 266:1959–1960.
15. Nicolaides, N. C., Gualdi, R., Casadevall, C., Manzella, L., and Calabretta, B. 1991. Positive autoregulation of c-myb expression via MYB binding in the 5' flanking region of the human c-myb gene. Mol. Cell. Biol. 11:6166–6176.
16. Nicolaides, N. C., Correa, I., Casadevall, C., Travali, S., Soprano, K. J., and Calabretta, B. 1992. The Jun family members, c-JUN and JUND, transactivate the human c-myb promoter via an Ap1 like element. J. Biol. Chem. 267, 19665–19672.
17. Nicolaides, N. C., Papadopoulos, N., Liu, B., Wei, Y. F., Carter, K. C., Ruben, S. M., Rosen, C. A., Haseltine, W. A., Fleischmann, R. D., Fraser, C. M., Adams, M. D., Venter, C. J., Dunlop, M. G., Hamilton, S. R., Petersen, G. M., de la Chapelle, A., Vogelstein, B., and kinzler, K. W. 1994. Mutations of two PMS homologs in hereditary nonpolyposis colon cancer. Nature 371: 75–80.
18. Nicolaides N. C., Kinzler, K. W., and Vogelstein, B. 1995. Analysis of the 5' region of PMS2 reveals heterogenous transcripts and a novel overlapping gene. Genomics 29:329–334.
19. Nicolaides, N. C., Carter, K. C., Shell, B. K., Papadopoulos, N., Vogelstein, B., and Kinzler, K. W. 1995. Genomic organization of the human PMS2 gene family. Genomics 30:195–206.
20. Nicolaides, N. C., Palombo, F., Kinzler, K. W., Vogelstein, B., and Jiricny, J. 1996. Molecular cloning of the N-terminus of GTBP. Genomics 31:395–397.
21. Palombo, F., Hughes, M., Jiricny, J., Truong, O., Hsuan, J. 1994. Mismatch repair and cancer. Nature 36:417.
22. Palombo, F., Gallinari, P., Iaccarino, I., Lettieri, T., Hughes, M. A., Truong, O., Hsuan, J. J., and Jiricny, J. 1995. GTBP, a 160-kilodalton protein essential for mismatch-binding activity in human cells. Science 268:1912–1914.
23. Pang, Q., Prolla, T. A., and Liskay, R. M. 1997. Functional domains of the *Saccharomyces cerevisiae* Mlh1p and Pms 1p DNA mismatch repair proteins and their relevance to human hereditary nonpolyposis colorectal cancer-associated mutations. Mol. Cell. Biol. 17:4465–4473.
24. Papadopoulos, N., Nicolaides, N. C., Wei, Y. F., Carter, K. C., Ruben, S. M., Rosen, C. A., Haseltine, W. A., Fleischmann, R. D., Fraser, C. M., Adams, M. D., Venter, C. J., Dunlop, M. G., Hamilton, S. R., Petersen, G. M., de la Chapelle, A., Vogelstein, B., and kinzler, K. W. 1994. Mutation of a mutL homolog is associated with hereditary colon cancer. Science 263:1625–1629.
25. Parsons, R., Li, G. M., Longley, M. J., Fang, W. H., Papadopolous, N., Jen, J., de la Chapelle, A., Kinzler, K. W., Vogelstein, B., and Modrich, P. 1993. Hypermutability and mismatch repair deficiency in RER+ tumor cells. Cell 75:1227–1236.
26. Parsons, R., Li, G. M., Longley, M., Modrich, P., Liu, B., Berk, T., Hamilton, S. R., Kinzler, K. W., and Vogelstein, B. 1995. Mismatch repair deficiency in phenotypically normal human cells. Science 268:738–740.
27. Perucho, M. 1996. Cancer of the microsattelite mutator phenotype. Biol Chem. 377:675–684.
28. Prolla, T. A, Pang, Q., Alani, E., Kolodner, R. A., and Liskay, R. M. 1994. MLH1, PMS1, and MSH2 Interaction during the initiation of DNA mismatch repair in yeast. Science 264:1091–1093.

29. Strand, M., Prolla, T. A., Liskay, R. M., and Petes, T. D. Destabilization of tracts of simple repetitive DNA in yeast by mutations affecting DNA mismatch repair. 1993. Nature 365:274–276.
30. Studier, F. W. Use of bacteriophage T7 lysozyme to improve an inducible T7 expression system. 1991. J. Mol. Biol. 219(1):37–44.
31. Su, S. S., Lahue, R. S., Au, K. G., and Modrich, P. 1988. Mispair specificity of methyl directed DNA mismatch corrections in vitro. J. Biol. Chem. 263:6829–6835.
32. Nicolaides N C, Littman S J, Modrich P, Kinzler K W, Vogelstein B 1998. A naturally occurring hPMS2 mutation can confer a dominant negative mutator phenotype. Mol Cell Biol 18:1635–1641.
33. Aronshtam A, Marinus M G. 1996. Dominant negative mutator mutations in the mutL gene of *Escherichia coli*. Nucleic Acids Res 24:2498–2504.
34. Wu TH, Marinus M G. 1994. Dominant negative mutator mutations in the mutS gene of *Escherichia coli*. J Bacteriol 176:5393–400.
35. Brosh R M Jr, Matson S W. 1995. Mutations in motif II of *Escherichia coli* DNA helicase II render the enzyme nonfunctional in both mismatch repair and excision repair with differential effects on the unwinding reaction. J Bacteriol 177:5612–5621.
36. Studamire B, Quach T, Alani, E. 1998. Saccharomyces cerevisiae Msh2p and Msh6p ATPase activities are both required during mismatch repair. Mol Cell Biol 18:7590–7601.
37. Alani E, Sokolsky T, Studamire B, Miret J J, Lahue R S. 1997. Genetic and biochemical analysis of Msh2p-Msh6p: role of ATP hydrolysis and Msh2p-Msh6p subunit interactions in mismatch base pair recognition. Mol Cell Biol 17:2436–2447.
38. Lipkin S M, Wang V, Jacoby R, Banerjee-Basu S, Baxevanis A D, Lynch H T, Elliott R M, and Collins F S. 2000. MLH3: a DNA mismatch repair gene associated with mammalian microsatellite instability. Nat Genet 24:27–35.
39. Lee C C, Lin H K, Lin J K. 1994. A reverse mutagenicity assay for alkylating agents based on a point mutation in the beta-lactamase gene at the active site serine codon. Mutagenesis 9:401–405.
40. Vidal A, Abril N, Pueyo C. 1995. DNA repair by Ogt alkyltransferase influences EMS mutational specificity. Carcinogenesis 16:817–821.
41. Fu, K. P., Grace, M. E., Hsiao, C. L., and Hung, P. P. 1988. Elimination of antibiotic-resistant plasmids by quinolone antibiotics. Chem. Abstracts 34(5):415–418.
42. BiWang, H., ZhiPeng, H., and Xiong, G. 1999. Transformation of *Escherichia coli* and Bacillus thuringiensis and their plasmid curing by electroporation. J. of Fujian Agricultural University 28(1):43–46.
43. Brosius, J. 1988. Expression vectors employing lambda-, trp-, lac-, and lpp-derived promoters. Biotechnology 10:205–225.

We claim:

1. A method for making a hypermutable bacterium comprising the steps of:

introducing into a bacterium a polynucleotide encoding a dominant negative PMS2 mismatch repair protein, wherein the dominant negative PMS2 protein consists of the first 133 amino acids of PMS2, under the control of an inducible transcription regulatory sequence; and inducing said inducible transcription regulatory sequence in said bacterium; whereby said bacterium becomes hypermutable.

2. The method of claim 1 wherein the dominant negative PMS2 mismatch repair protein is a dominant negative human PMS2 protein consisting of the first 133 amino acids of human PMS2.

3. The method of claim 1 wherein the dominant negative PMS2 mismatch repair protein is a dominant negative plant PMS2 protein consisting of the first 133 amino acids of a plant PMS2.

4. The method of claim 3 wherein said polynucleotide encoding a dominant negative PMS2 mismatch repair protein comprises a truncation mutation at codon 134.

5. The method of claim 2 wherein said polynucleotide encoding a dominant negative PMS2 mismatch repair protein comprises a truncation mutation at codon 134.

6. A homogeneous composition of induced, cultured, hypermutable bacteria which comprise a polynucleotide encoding a dominant negative mismatch repair protein under the control of an inducible transcription regulatory sequence, wherein said dominant negative mismatch repair protein consists of the first 133 amino acids of PMS2, wherein said dominant negative mismatch repair protein exerts a dominant negative effect when expressed in said bacteria.

7. The homogeneous composition of claim 6 wherein the dominant negative mismatch repair protein consists of the first 133 amino acids of human PMS2.

8. The method of claim 1 wherein the polynucleotide encoding a dominant negative PMS2 mismatch repair protein comprises a truncation mutation at codon 134.

9. A method for making a hypermutable bacterium comprising the steps of:

introducing into a bacterium a polynucleotide encoding a dominant negative mismatch repair protein under the control of an inducible transcription regulatory sequence, wherein said dominant negative mismatch repair protein is a dominant negative PMSR3 mismatch repair protein; and inducing said bacterium; wherein said dominant negative PMSR3 mismatch repair protein exerts a dominant negative effect on mismatch repair when expressed in said bacterium, whereby said bacterium becomes hypermutable.

10. A homogeneous composition of induced, cultured, hypermutable bacteria which comprise a polynucleotide encoding a dominant negative PMSR3 mismatch repair protein under the control of an inducible transcription regulatory sequence, wherein said dominant negative PMSR3 mismatch repair protein exerts a dominant negative effect when expressed in said bacteria.

11. The composition of claim 6 wherein the dominant negative mismatch repair protein consists of the first 133 amino acids of plant PMS2.

12. The composition of 11 wherein the dominant negative plant mismatch repair protein is an *Arabidopsis thaliana* mismatch repair protein consisting of the first 133 amino acids of *Arabidopsis thaliana* PMS2.

13. The method of claim 3 wherein the dominant negative plant PMS2 mismatch repair protein consists of the first 133 amino acids of *Arabidopsis thaliana* PMS2.

14. The method of claim 4 wherein the dominant negative plant PMS2 mismatch repair protein consists of the first 133 amino acids of *Arabidopsis thaliana* PMS2.

15. The homogeneous composition of claim 6 wherein the dominant negative mismatch repair protein is a dominant negative *Arabidopsis thaliana* mismatch repair protein which consists of the first 133 amino acids of *Arabidopsis thaliana* PMS2.

* * * * *